(12) United States Patent
Stoessel et al.

(10) Patent No.: US 9,416,310 B2
(45) Date of Patent: Aug. 16, 2016

(54) MATERIALS FOR ELECTRONIC DEVICES

(75) Inventors: Philipp Stoessel, Frankfurt (DE);
Holger Heil, Frankfurt am Main (DE);
Dominik Joosten, Frankfurt (DE);
Christof Pflumm, Frankfurt (DE); Anja Gerhard, Egelsbach (DE)

(73) Assignee: Merck Patent GmbH, Darmstadt (DE)

( * ) Notice: Subject to any disclaimer, the term of this patent is extended or adjusted under 35 U.S.C. 154(b) by 1149 days.

(21) Appl. No.: 13/497,654

(22) PCT Filed: Aug. 25, 2010

(86) PCT No.: PCT/EP2010/005221
§ 371 (c)(1),
(2), (4) Date: Mar. 22, 2012

(87) PCT Pub. No.: WO2011/035836
PCT Pub. Date: Mar. 31, 2011

(65) Prior Publication Data
US 2012/0187349 A1    Jul. 26, 2012

(30) Foreign Application Priority Data
Sep. 23, 2009  (DE) .................. 10 2009 042 693

(51) Int. Cl.
| | |
|---|---|
| *H01L 51/54* | (2006.01) |
| *C07F 15/00* | (2006.01) |
| *C09K 11/06* | (2006.01) |
| *C07F 15/02* | (2006.01) |
| *H01L 51/00* | (2006.01) |
| *C09B 57/00* | (2006.01) |
| *C09B 57/10* | (2006.01) |
| *H01L 51/50* | (2006.01) |

(52) U.S. Cl.
CPC ............. *C09K 11/06* (2013.01); *C07F 15/0086* (2013.01); *C07F 15/02* (2013.01); *C09B 57/00* (2013.01); *C09B 57/10* (2013.01); *H01L 51/0087* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/5016* (2013.01); *H01L 51/5048* (2013.01); *Y02E 10/549* (2013.01)

(58) Field of Classification Search
CPC . C07F 15/02; C07F 15/0086; H01L 51/0084; H01L 51/0087; H01L 51/0083; H01L 51/0091; H01L 51/0092; H01L 51/50; H01L 51/5016; C09K 11/06; C09K 2211/1029; C09K 2211/1044; C09K 2211/1088; C09K 2211/1092; C09K 2211/185
See application file for complete search history.

(56) References Cited

U.S. PATENT DOCUMENTS

| | | | |
|---|---|---|---|
| 2005/0260444 A1 | 11/2005 | Forrest et al. | |
| 2006/0172146 A1* | 8/2006 | Igarashi | C07D 471/22 428/690 |
| 2006/0204787 A1* | 9/2006 | Sano | H01L 51/0087 428/690 |
| 2009/0079340 A1 | 3/2009 | Kinoshita et al. | |

FOREIGN PATENT DOCUMENTS

| | | |
|---|---|---|
| CN | 101307065 | 11/2008 |
| CN | 101307065 A | 11/2008 |
| JP | 2006148012 A | 6/2006 |
| JP | 2007/161886 A * | 6/2007 |

OTHER PUBLICATIONS

Clerici et al. "Internal metalation of N- or P-donor ligands to give multidentate organometallic compounds." Journal of the Chemical Society, Chemical Communications. 1973. vol. 15, pp. 516-517.*
Küpper, "Iron Diaryls with Metal-Carbon σBonds", J. Organometal. Chem., vol. 13, pp. 219-225 (1968).
Küpper et al., Zeitschrifft für Naturforschung, vol. 23, No. 4, pp. 613-614 (1968).
Lipshutz et al., "Cyanocuprate-mediated intramolecular biaryl couplings applied to an ellagitannin. Synthesis of (+)-O-permethyltellimagrandin II", TetrahedronLetters, vol. 35, No. 31, pp. 5567-5570, (1994).
Baltensperger, et al., Organometallics, vol. 2, No. 5, (1983), pp. 571-578.(XP002965263).
International Search Report for PCT/EP2010/005221 mailed Jan. 21, 2011.

* cited by examiner

*Primary Examiner* — Andrew K Bohaty
(74) *Attorney, Agent, or Firm* — Drinker Biddle & Reath LLP

(57) ABSTRACT

The present invention relates to compounds of the formula (I) and to the use thereof in electronic devices, in particular organic electroluminescent devices. Furthermore, the present invention relates to electronic devices comprising at least one compound according to the invention, preferably as emitter material or as charge-transport material.

7 Claims, No Drawings

MATERIALS FOR ELECTRONIC DEVICES

CROSS-REFERENCE TO RELATED APPLICATIONS

This application is a national stage application (under 35 U.S.C. §371) of PCT/EP2010/005221, filed Aug. 25, 2010, which claims benefit of German application 10 2009 042 693.0, filed Sep. 23, 2009.

The present invention relates to transition-metal complexes of the formula (I), to the use thereof in electronic devices, preferably as emitter materials, to ligands of the formula (Ia), to the use of the ligands for the preparation of metal complexes, to electronic devices comprising at least one compound of the formula (I), and to a process for the preparation of the compounds according to the invention.

Chelate complexes and organometallic compounds are used as functional materials in a number of different applications which can be ascribed to the electronics industry in the broadest sense. In the case of organic electroluminescent devices (OLEDs, general description of the structure cf. U.S. Pat. No. 4,539,507 and U.S. Pat. No. 5,151,629), which are based on organic components, there is still a further need for improvement, in spite of the success that has already been achieved.

In recent years, organometallic complexes, which exhibit phosphorescence instead of fluorescence, have increased in importance (cf. M. A. Baldo, S. Lamansky, P. E. Burrows, M. E. Thompson, S. R. Forrest, Appl. Phys. Lett., 1999, 75, 4-6). For theoretical spin-statistical reasons, an up to four-fold increase in the energy and power efficiency is possible using organometallic compounds as phosphorescent emitters. Essential conditions for practical application which may be mentioned are a long operating lifetime, high stability to heating, a low use and operating voltage in order to facilitate mobile applications, and high colour purity.

Metal complexes of the transition metals from group 10 (Ni, Pd, Pt) in which the central metal is bonded via two aromatic N atoms and two C atoms (WO 2004/108857, WO 2005/042550, WO 2005/042444, US 2006/0134461 A1) or two imine-like N atoms in combination with two phenolic O atoms (WO 2004/108857) or via two aromatic N atoms and two basic N atoms (WO 2004/108857) are known in OLED technology. The known compounds have, inter alia, electroluminescence in the blue, red and green region of the electromagnetic spectrum.

Furthermore, the literature (U. Fekl et al., Organometallics 2008, 27, 1765-1779) describes luminescent coordination compounds containing a bidentate diphenylmethylene ligand and a further bidentate ligand which is bonded to the metal atom via nitrogen atoms. However, the literature discloses neither linking of the aromatic ring to the heteroatom-based ligand nor data on the use of the compounds in electronic devices.

However, the advantages offered by the use of triplet emission in the area of organic electroluminescent devices are countered by a number of problems and difficulties. Some particularly relevant areas with a need for improvement will be mentioned below:

1) Many of the known metal complexes have low thermal stability. This results in liberation of organic pyrolysis products during vacuum deposition, which in some cases, even in small amounts, reduce the operating lifetime of the OLED.
2) Likewise, the strong interaction of the complex units in the solid, in particular in the case of planar complexes of $d^8$ metals, such as platinum(II), causes aggregation of the complex units in the emitter layer if the degree of doping exceeds about 0.1%, which is the case in accordance with the current state of the art. This aggregation results in the formation of so-called excimers or exciplexes on excitation (optical or electrical). These aggregates frequently have an unstructured, broad emission band, which makes the generation of pure primary colours (RGB) considerably more difficult. In general, the efficiency for this transition also drops. The emission colour is thus dependent on the degree of doping, a parameter which can only be controlled precisely with considerable technical effort, in particular in large production plants.
3) No blue-emitting triplet emitters which meet the technical requirements made of high-quality display or lighting devices are known to date.

In summary, there is a demand for novel functional compounds for organic electroluminescent devices which do not have one or more of the above-mentioned disadvantages or are accompanied by improvements in these areas and which preferably exhibit electroluminescence in the blue, red and green region of the electromagnetic spectrum.

SUMMARY OF THE INVENTION

The object of the present invention is therefore to provide novel metal complexes which are suitable as emitters for use in OLEDs.

It has now been found that compounds of the formula (I) are suitable for use as functional materials in organic electroluminescent devices, preferably as emitter materials for blue-phosphorescent OLEDs, but also as emitter materials for other emission colours.

The invention thus relates to a compound of the formula (I),

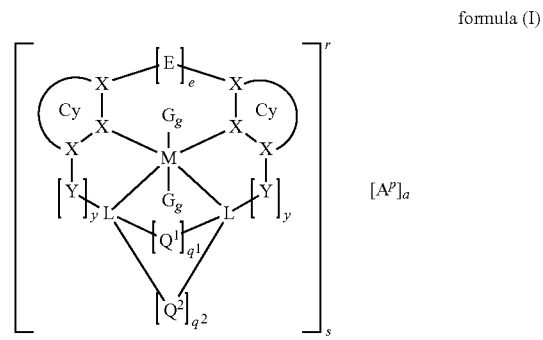

formula (I)

where the following applies to the symbols and indices used:

M is a metal,

Cy is on each occurrence, identically or differently, an aryl or heteroaryl group having 5 to 60 ring atoms, which may in each case be substituted by one or more radicals $R^C$, with the proviso that the groups denoted by X are constituents of the group Cy, E is on each occurrence, identically or differently, $C(R^B)_2$, $-CR^B=CR^B-$, 1,2-, 1,3- or 1,4-phenylene which is optionally substituted by one or more radicals $R^B$, or $C=O, C=S, C=C(R^B)_2, C=NR^B, O, S, Se, PR^B$ or $P(R^B)=O$, G is on each occurrence, identically or differently, a neutral, cationic or anionic ligand, which may also be bonded to one or more of the groups Cy, E, Y, L or $Q^1$ or $Q^2$, $Q^2$ are on each occurrence, identically or differently, $C(R^B)_2$, $-(R^B)C=C(R^B)-$, a phenylene group or an arylene or heteroarylene group having 5 to 60 ring atoms, each of which may be substituted by one or more radicals $R^B$, or C=O, C=S, C=C($R^B$)$_2$, C=N$R^B$, O, S, Se, P$R^B$ or P($R^B$)=O, with the proviso that one or more substituents $Q^1$ may be linked to one or more substituents $Q^2$, X is on each occurrence, identically or differently, C, N, P, O or S, where the groups X bonded to Y or E are selected on each occurrence, identically or differently, from C and N and where at least one of the two groups X bonded to M represents a carbon atom, Y is on each occurrence, identically or differently, C($R^B$)$_2$, C=O, C=S, C=C($R^B$)$_2$, C=N$R^B$, N$R^B$, O, S, Se, P$R^B$ or P($R^B$)=O, where one or more substituents $R^B$ on Y may form an aliphatic, aromatic or heteroaromatic fused ring with the adjacent ring Cy, L is on each occurrence, identically or differently, C, N, P, O, S or Se, A is on each occurrence, identically or differently, any desired counterion, e is 0, 1, 2, 3 or 4, where, for e=0, the respective free bonding site on X is saturated by a substituent $R^C$, and where the sum of the values of the indices e, $q^1$ and $q^2$ is greater than or equal to one, g is on each occurrence, identically or differently, 0 or 1, $q^1$, $q^2$ are on each occurrence, identically or differently, 0, 1, 2, 3 or 4, where the substituents $Q^1$ and $Q^2$ may only occur to the extent of the free bonding sites on L, and, in the case of $q^1$=0 or $q^2$=0, free bonding sites occurring on L may be saturated by substituents $R^B$, and where the sum of the values of the indices e, $q^1$ and $q^2$ is greater than or equal to one, y is on each occurrence, identically or differently, 1 or 2, a is 0, 1, 2, 3 or 4, p is −4, −3, −2, −1, 0, 1, 2, 3 or 4 and represents the charge number of the group A, r is −4, −3, −2, −1, 0, 1, 2, 3 or 4 and represents the charge number of the complex in square brackets in formula (I), s is 1, 2, 3 or 4, $R^B$, $R^C$ are on each occurrence, identically or differently, H, D, F, Cl, Br, I, CHO, N($R^1$)$_2$, C(=O)$R^1$, P(=O)($R^1$)$_2$, S(=O)$R^1$, S(=O)$_2$$R^1$, C$R^1$=C($R^1$)$_2$, CN, NO$_2$, Si($R^1$)$_3$, B(O$R^1$)$_2$, OSO$_2$$R^1$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals $R^1$ and where furthermore one or more non-adjacent CH$_2$ groups may be replaced by $R^1$C=C$R^1$, C≡C, Si($R^1$)$_2$, Ge($R^1$)$_2$, Sn($R^1$)$_2$, C=O, C=S, C=Se, C=N$R^1$, P(=O)($R^1$), SO, SO$_2$, N$R^1$, O, S or CON$R^1$ and where furthermore one or more H atoms may be replaced by D, F, Cl, Br, I, CN or NO$_2$, or a mono- or polycyclic aromatic or heteroaromatic ring system having 5 to 60 aromatic ring atoms, which may in each case be substituted by one or more non-aromatic radicals $R^1$, or an aryloxy or heteroaryloxy group having 5 to 60 aromatic ring atoms, which may be substituted by one or more non-aromatic radicals $R^1$, or a combination of these systems; in addition, two or more identical or different radicals $R^B$ and $R^C$ may be linked to one another and form a mono- or polycyclic, aliphatic or aromatic ring system, and furthermore one or more radicals $R^B$ may optionally also additionally be bonded to the group Cy, and furthermore one or more radicals $R^C$ may optionally also additionally be bonded to the group E or Y, $R^1$ is on each occurrence, identically or differently, H, D, F, Cl, Br, I, CHO, N($R^2$)$_2$, C(=O)$R^2$, P(=O)($R^2$)$_2$, S(=O)$R^2$, S(=O)$_2$$R^2$, C$R^2$=C($R^2$)$_2$, CN, NO$_2$, Si($R^2$)$_3$, B(O$R^2$)$_2$, OSO$_2$$R^2$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent CH$_2$ groups may be replaced by $R^2$C=C$R^2$, C≡C, Si($R^2$)$_2$, Ge($R^2$)$_2$, Sn($R^2$)$_2$, C=O, C=S, C=Se, C=N$R^2$, P(=O)($R^2$), SO, SO$_2$, N$R^2$, O, S or CON$R^2$ and where one or more H atoms may be replaced by D, F, Cl, Br, I, CN or NO$_2$, or a mono- or polycyclic aromatic or heteroaromatic ring system having 5 to 60 aromatic ring atoms, which may in each case be substituted by one or more non-aromatic radicals $R^2$, or an aryloxy or heteroaryloxy group having 5 to 60 aromatic ring atoms, which may be substituted by one or more non-aromatic radicals $R^2$, or a combination of these systems, where two or more radicals $R^1$ may be linked to one another and may form a mono- or polycyclic, aliphatic or aromatic ring system, $R^2$ is on each occurrence, identically or differently, H, D, F or an aliphatic, aromatic and/or heteroaromatic organic radical having 1 to 20 C atoms, in which, in addition, one or more H atoms may be replaced by F; two or more identical or different substituents $R^2$ here may also be linked to one another and form a mono- or polycyclic, aliphatic or aromatic ring system, and the stoichiometric indices s and a are selected, depending on the charge numbers r and p present in the complex in square brackets in formula (I) or in the counterion A, in such a way that overall a charge-neutral compound results, and, for r=0, a=0, i.e. no counterion A is present, and where the following compounds are not covered by the claim:

CAS 84393-87-3

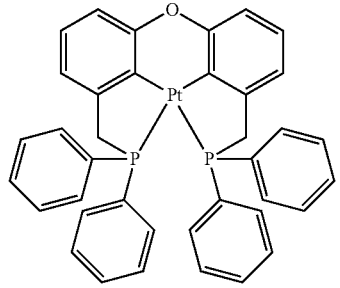

CAS 84393-88-4

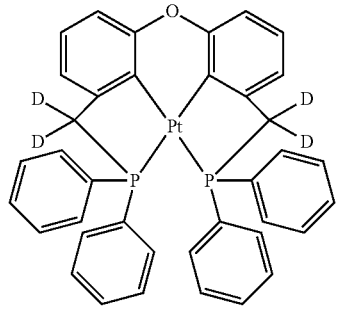

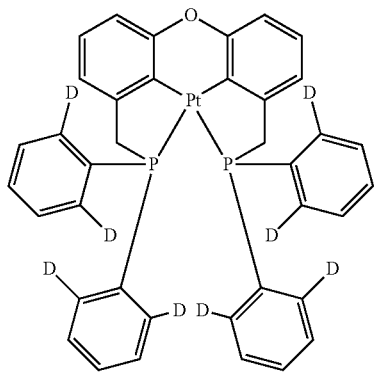
CAS 84393-89-5

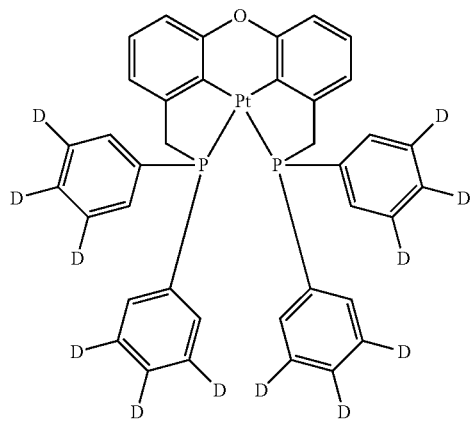
CAS 84393-90-8

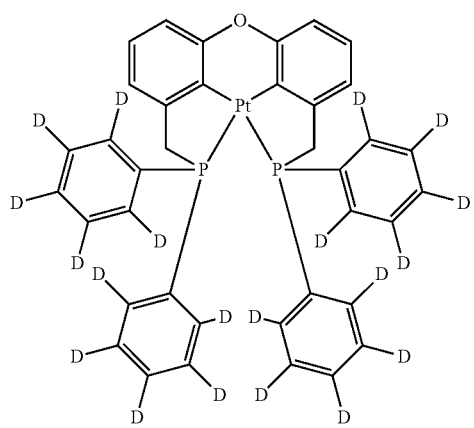
CAS 84393-91-9

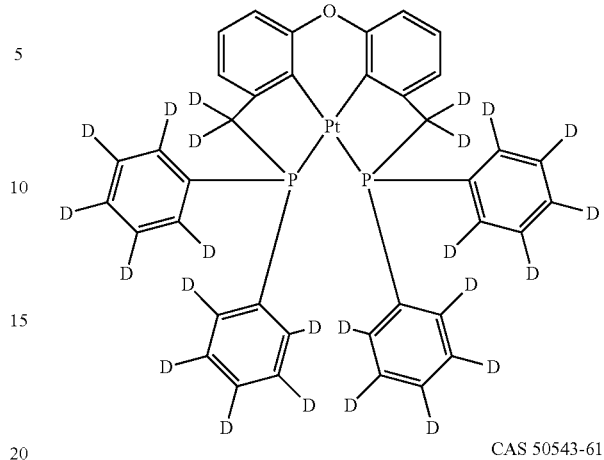
CAS 84393-92-0

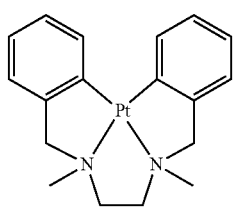
CAS 50543-61-8

CAS 20573-74-4

A DETAILED DESCRIPTION OF THE INVENTION

For compounds of the formula (I) and for all other formulae indicated below, it is stipulated that the individual moieties E, Y, $Q^1$ and $Q^2$ in the groups $(E)_e$, $(Y)_y$, $(Q^1)_{q1}$ and $(Q^2)_{q2}$ do not have to be of the same type, but may also represent different chemical radicals in accordance with their definitions indicated above.

For example, a group $(E)_e$ for the purposes of the present application is taken to mean a group in which e groups of the formula E are arranged one after the other. The groups E here may be identical or different. For the specific case in which E represents a group of the formula $C(R^B)_2$ and e is equal to 2, $(E)_e$ thus stands for a group of the formula —$C(R^B)_2$—$C(R^B)_2$—.

The following general definitions are used in the description of the present invention:

An aryl group in the sense of this invention contains 6 to 60 C atoms, preferably 6 to 30 C atoms and particularly preferably 6-20 C atoms; a heteroaryl group in the sense of this invention contains 2 to 60 C atoms and at least 1 heteroatom, preferably 3 to 30 C atoms and at least 1 heteroatom and particularly preferably 3 to 20 C atoms and at least 1 heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, etc.

An aromatic ring system in the sense of this invention contains 6 to 60 carbon atoms, preferably 6 to 30 carbon atoms, particularly preferably 6 to 20 carbon atoms. An aromatic ring system in the sense of the present invention is intended to be taken to mean a system which does not necessarily contain only aromatic groups, but instead in which, in addition, a plurality of aromatic groups may be connected by a short non-aromatic unit (preferably less than 10% of the atoms other than H), such as, for example, $sp^3$-hybridised C, O, N, etc. These aromatic ring systems can be monocyclic or polycyclic, i.e. they can contain one ring (for example phenyl) or two or more rings, which may also be condensed (for example naphthyl) or covalently bonded (for example biphenyl), or contain a combination of condensed and linked rings.

Preferred aromatic ring systems are, for example, benzene, biphenyl, terphenyl, naphthalene, anthracene, binaphthyl, phenanthrene, benzanthracene, dihydrophenanthrene, pyrene, dihydropyrene, chrysene, perylene, tetracene, pentacene, benzopyrene, fluorene and indene.

A heteroaromatic ring system in the sense of this invention contains 5 to 60 aromatic ring atoms, preferably 5 to 30 aromatic ring atoms, particularly preferably 5 to 20 aromatic ring atoms. The heteroaromatic ring system furthermore contains at least one heteroatom selected from N, O and S. A heteroaromatic ring system is in addition intended to be taken to mean a system which does not necessarily contain only aromatic or heteroaromatic groups, but instead in which, in addition, a plurality of aromatic or heteroaromatic groups may be connected by a short non-aromatic unit (preferably less than 10% of the atoms other than H), such as, for example, $sp^a$-hybridised C, O, N, etc. These heteroaromatic ring systems can be monocyclic or polycyclic, i.e. they can contain one ring (for example pyridyl) or two or more rings, which may also be condensed or covalently bonded, or contain a combination of condensed and linked rings.

Preferred heteroaromatic ring systems are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals $R^B$, $R^C$ and $R^1$, is preferably taken to mean the radicals methyl, ethyl, n-propyl, i-propyl, n-butyl, i-butyl, s-butyl, t-butyl, 2-methylbutyl, n-pentyl, s-pentyl, cyclo pentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

In accordance with the invention, A represents any desired counterion, which may be positively or negatively charged. A preferably has the opposite charge to the chelate complex according to the invention, i.e. is positively charged if the complex has a negative charge and negatively charged if the complex has a positive charge.

A can represent a simple ion, such as, for example, $Na^+$, $Ca^{2+}$ or $Cr$, or a multiatom ion, such as, for example, $NH_4^+$, $SO_4^{2-}$, $PF_6^-$, or an ion of an organic compound, such as, for example, acetate, oxalate or triethyl-ammonium, or a complex ion, such as, for example, $Fe(CN)_6^{4-}$ or $Cu(Cl_4)^{2-}$. In one possible embodiment of the invention, A represents a chelate complex of the metal M.

In a preferred embodiment of the invention, the complexes according to the invention represent electrically neutral compounds, i.e. the charge r is equal to zero and no counterion A is present.

In a further preferred embodiment, the ligand G is selected, identically or differently on each occurrence, from the group comprising carbon monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, $F^-$, $Cl^-$, $Br^-$ and $I^-$, alkyl acetylides, aryl acetylides, cyanide, cyanate, isocyanate, thiocyanate, isothiocyanate, aliphatic or aromatic alcoholates, aliphatic or aromatic thio alcoholates, amides, carboxylates, aryl groups, nitrogen-containing heterocycles, $O^{2-}$, $S^{2-}$, carbides, nitrenes, diamines, imines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, dithiolates derived from dithiols, borates of nitrogen-containing heterocycles, $\eta^5$-cyclopentadienyl, $\eta^5$-pentamethylcyclopentadienyl, $\eta^6$-benzene or $\eta^7$-cycloheptatrienyl, each of which may be substituted by one or more radicals $R^B$, where the ligand G may also be bonded to the groups Cy, E, Y, L, $Q^1$ or $Q^2$.

Preference is furthermore given to compounds of the formula (I), characterised in that the sum of the valence electrons of the metal atom is 16 in tetracoordinated complexes and 16 or 18 in pentacoordinated complexes and 18 in hexacoordinated complexes. This preference is due to the particular stability of these metal complexes (see, for example, Elschenbroich, Salzer, *Organometallchemie* [Organometallic Chemistry], Teubner Studienbücher, Stuttgart 1993).

In a preferred embodiment of the invention, the metal M represents a transition metal from one of groups 3-13 of the Periodic Table. M is particularly preferably equal to Cr, Mo, W, Mn, Re, Ru, Os, Rh, Ir, Ni, Pd, Pt, Cu, Ag or Au; the metal M is very particularly preferably equal to Ir, Pt, Cu or Au.

At least one of the two groups X bonded to the metal M represents a carbon atom. In a preferred embodiment of the invention, both of the two groups X bonded to the metal M represent carbon atoms.

In a preferred embodiment of the invention, one or both of the two groups Y in compounds of the formula (I) form a fused ring with the respective adjacent group Cy. Compounds in accordance with this preferred embodiment represent, for example, the compounds of the formulae (VIII) to (XVII) indicated in a following section.

In a further preferred embodiment, the two substituents $R^B$ are linked in one or more groups $C(R^B)_2$ which stand for E, $Q^1$, $Q^2$ or Y. It is very particularly preferred here for the divalent group —$C(R^B)_2$— to have a chemical structure of one of the formulae (A1) to (A3) mentioned below, where the structures may be substituted, identically or differently, at any desired positions by one or more radicals $R^1$, $R^1$ defined as indicated above, and Z is selected, identically or differently, from O, S, $C(R^1)_2$ and $NR^1$:

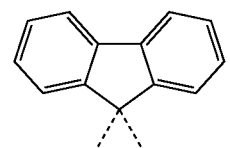

formula (A1)

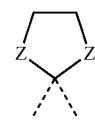

formula (A2)

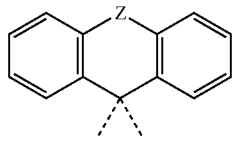

formula (A3)

In the compounds according to the invention, the sum of the values of the indices e, $q^1$ and $q^2$ is at least equal to 1. In all compounds according to the invention, a chelating, tetradentate ligand is thus present which coordinates to the metal M and may either be open-chain or forms a closed ring.

In a preferred embodiment, the value of the index e is at least equal to 1.

In a further preferred embodiment, the sum of the values of the indices $q^1$ and $q^2$ is at least equal to 1.

In a further preferred embodiment, both the value of the index e is at least equal to 1 and the sum of the values of the indices $q^1$ and $q^2$ is at least equal to 1, so that the compound of the formula (I) according to the invention contains a macrocyclic, chelating ligand.

If a macrocyclic ligand is present, this preferably has 12 to 20 members, particularly preferably 14 to 16 members and very particularly preferably 15 members.

A 15-membered macrocyclic ligand contains, for example, the following compound; the atoms forming the chelate ring are numbered in order to illustrate the numbering system.

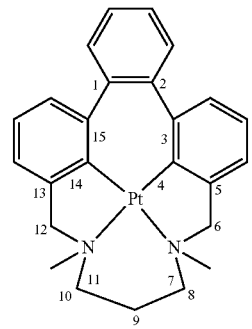

In a preferred embodiment of the invention, the index e furthermore has a value of 1, 2 or 3, particularly preferably a value of 1 or 2.

The indices $q^1$ and $q^2$ particularly preferably each adopt, identically or differently, the values 1, 2, 3 or 4.

In addition, one or more of the substituents $Q^1$ are furthermore particularly preferably linked to one or more of the substituents $Q^2$. In these cases, the group shown below

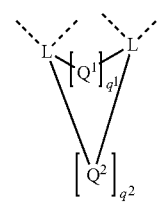

preferably represents, as a moiety of the formula (I), a chemical structure selected from the following formulae (B) and (C), where E is as defined above, and the structures of the formulae (B) and (C) may be substituted by one or more radicals $R^B$:

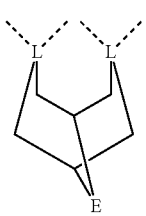

formula (B)

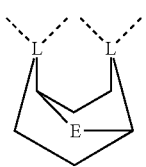

formula (C)

Particular preference is given here to the embodiments of the formulae (B) and (C) indicated below of the formulae (a) to (h), where the structures may be substituted by one or more radicals $R^B$:

formula (a)

[Structure: bicyclic diamine]

formula (b)

[Structure: bicyclic diamine with =O]

formula (c)

[Structure: bicyclic diamine]

formula (d)

[Structure: bicyclic diamine with O]

formula (e)

[Structure: bicyclic diphosphine]

formula (f)

[Structure: bicyclic diphosphine with =O]

formula (g)

[Structure: bicyclic diphosphine]

formula (h)

[Structure: bicyclic diphosphine with O]

For preferred embodiments of the compounds of the formula (I), the following furthermore applies, independently of one another:

E is on each occurrence, identically or differently, $C(R^B)_2$, $-CR^B=CR^B-$, 1,2-phenylene which is optionally substituted by one or more radicals $R^B$, or CO, $NR^B$, O or S;

L is on each occurrence, identically or differently, N or P;

$Q^1$, $Q^2$ are on each occurrence, identically or differently, $C(R^B)_2$, C=O, C=S, $C=C(R^B)_2$, $C=NR^B$, O, S, Se, $-CR^B=CR^B-$, $PR^B$ or $P(R^B)=O$, or phenylene, naphthylene or phenanthrenylene, each of which is optionally substituted by one or more radicals $R^B$, where one or more substituents $Q^1$ may be linked to one or more substituents $Q^2$;

X is on each occurrence, identically or differently, C, N or S, where the groups X bonded to Y or E are selected on each occurrence, identically or differently, from C and N, and where at least one of the two groups X bonded to the metal M represents a carbon atom;

Y is on each occurrence, identically or differently, $C(R^B)_2$;

e is equal to 0, 1, 2 or 3;

$q^1$, $q^2$ are on each occurrence, identically or differently, 0, 1, 2, 3 or 4;

y is equal to 1;

and the sum of the values of the indices e, $q^1$ and $q^2$ is greater than or equal to one.

E is very particularly preferably, identically or differently on each occurrence, $C(R^B)_2$.

$Q^1$ and $Q^2$ are very particularly preferably, identically or differently on each occurrence, $C(R^B)_2$, $-CR^B=CR^B-$, or 1,2-phenylene, 1,2-naphthylene, 2,3-naphthylene, 1,8-naphthylene or 9,10-phenanthrenylene, each of which is optionally substituted by one or more radicals $R^B$.

X is very particularly preferably, identically or differently on each occurrence, C or N.

Furthermore, the above-mentioned preferred embodiments very particularly preferably occur in combination with one another.

Further preferred embodiments of the compounds according to the invention are compounds of the formulae (II) to (VII), formula (II)

[Structure: metal complex with X, E, G, M, L, Y, Q¹, Q², A^p groups]

-continued

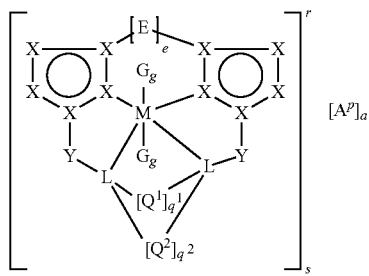
formula (III)

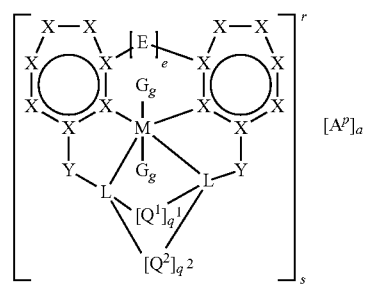
formula (IV)

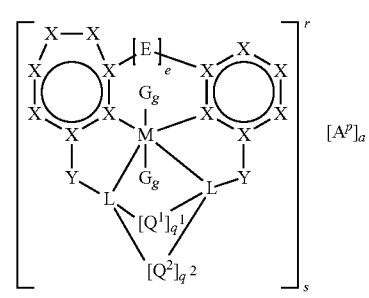
formula (V)

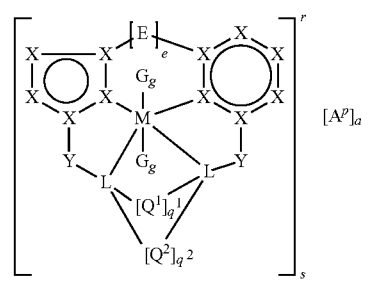
formula (VI)

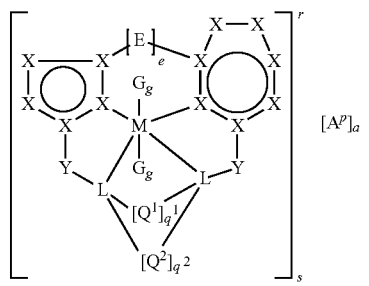
formula (VII)

where the symbols and indices have the meanings mentioned above, the rings depicted have an aromatic or heteroaromatic character, and free bonding sites on the groups X are saturated by substituents $R^C$.

Particular preference is given here to compounds of the formulae (II), (III) and (VI).

For compounds of the formulae (II) to (VII), it is particularly preferred for E, L, $Q^1$, $Q^2$, e, $q^1$ and $q^2$ to be defined as follows and for the other symbols and indices used to have the same meaning as described in connection with formula (I):

E is on each occurrence, identically or differently, $C(R^B)_2$, O or S,

L is on each occurrence, identically or differently, N or P, $Q^1$, $Q^2$ are on each occurrence, identically or differently, $C(R^B)_2$, C=O, C=S, C=C($R^B)_2$, C=$NR^B$, O, S, Se, $CR^B$=$CR^B$, $PR^B$, $P(R^B)$=O, or phenylene, naphthylene or phenanthrenylene, each of which is optionally substituted by one or more radicals $R^B$, where one or more substituents $Q^1$ may be linked to one or more substituents $Q^2$, e is equal to 0, 1, 2 or 3, $q^1$, $q^2$ are on each occurrence, identically or differently, 0, 1, 2, 3 or 4, and the sum of the values of the indices e, $q^1$ and $q^2$ is greater than or equal to one.

Furthermore, the same preferred embodiments of the symbols and indices as for formula (I) apply.

Compounds of the formulae (VIII) to (XVII) represent a further preferred embodiment of the compounds according to the invention,

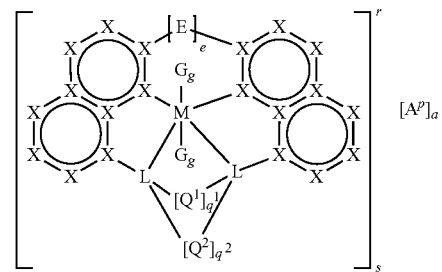
formula (VIII)

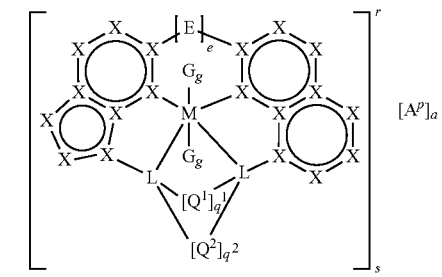
formula (IX)

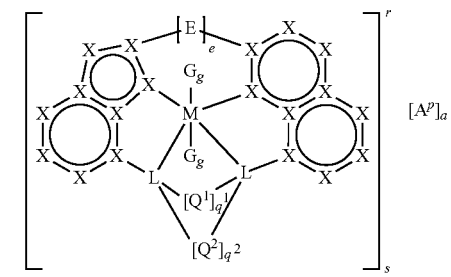
formula (X)

-continued formula (XI)

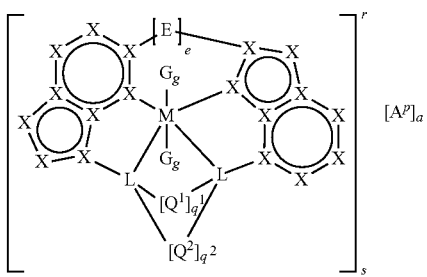

formula (XII)

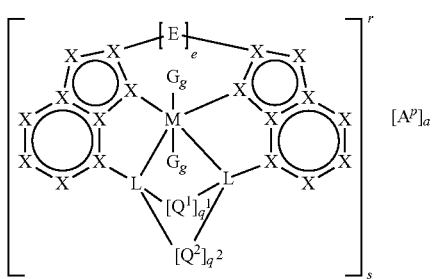

formula (XIII)

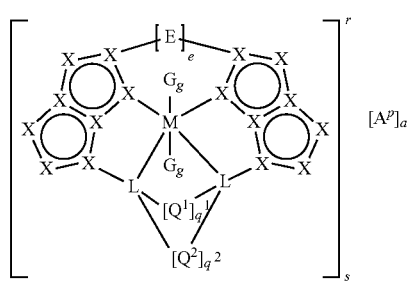

formula (XIV)

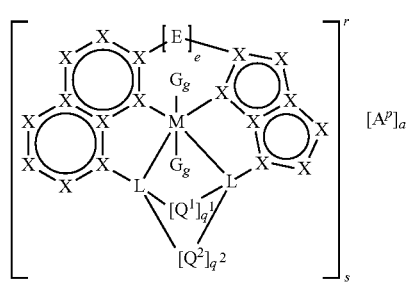

formula (XV)

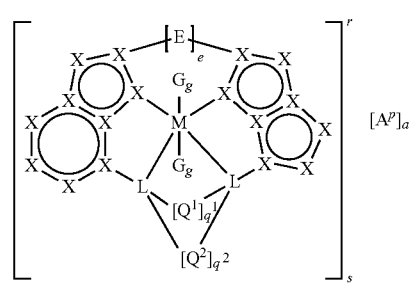

formula (XVI)

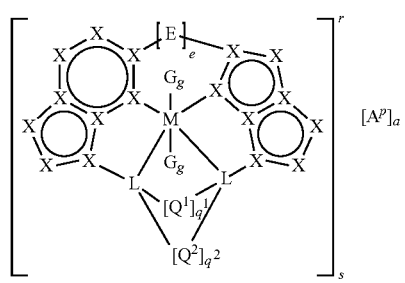

formula (XVII)

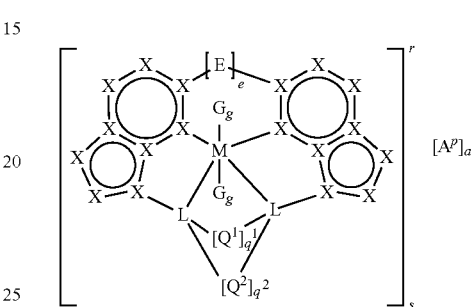

where the symbols occurring have the same meanings as described in connection with formula (I), and in addition the rings depicted have an aromatic or heteroaromatic character, and free bonding sites on the groups X are saturated by substituents $R^C$.

In a particularly preferred embodiment of compounds of the formulae (VIII) to (XVII), $Q^1$, $Q^2$ are on each occurrence, identically or differently, $C(R^B)_2$, C=O, C=S, C=C($R^B)_2$, C=N$R^B$, O, S, Se, —C$R^B$=C$R^B$—, P$R^B$, P($R^B$)=O, or phenylene, naphthylene or phenanthrenylene, each of which is optionally substituted by one or more radicals $R^B$, where one or more substituents $Q^1$ may be linked to one or more substituents $Q^2$.

Examples of compounds of the formula (I) according to the invention are the following compounds having the structural formulae I to 120:

1

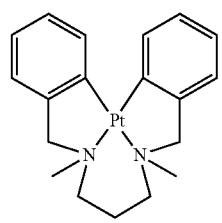

2

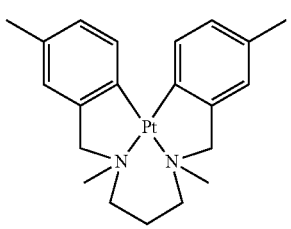

-continued
3
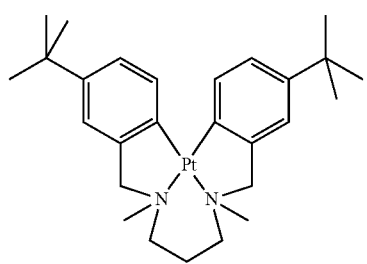
4
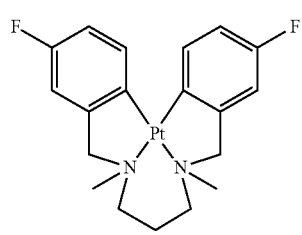
5
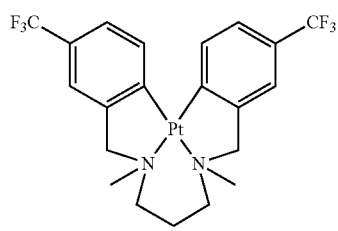
6
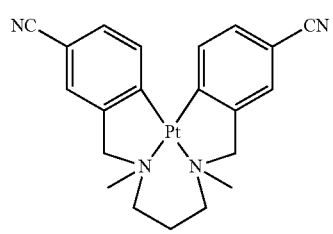
7
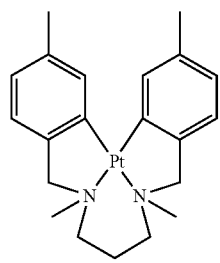
8
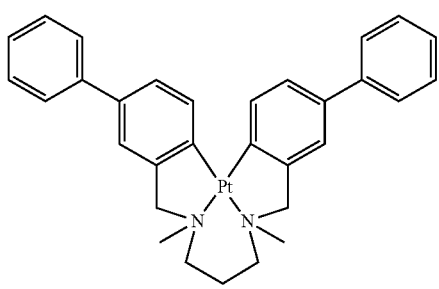
-continued
9
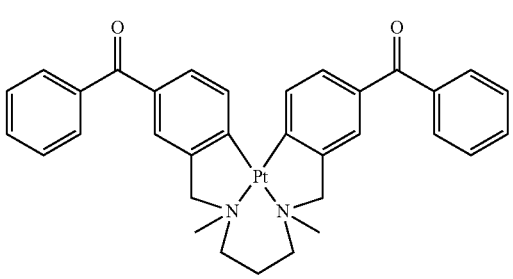
10
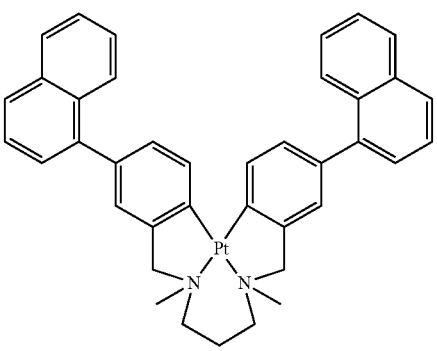
11
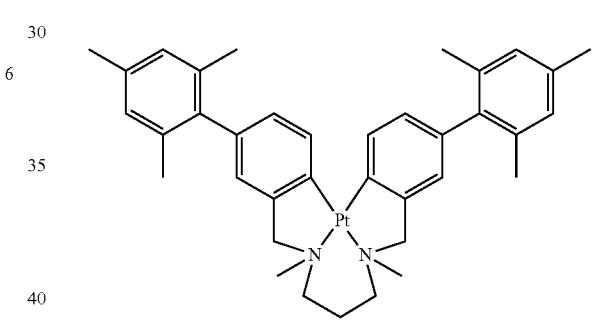
12
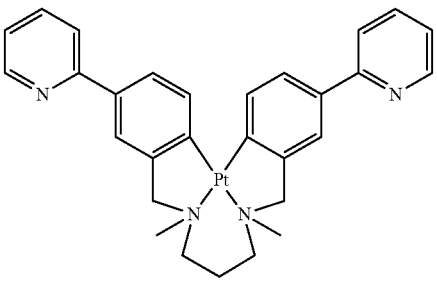
13
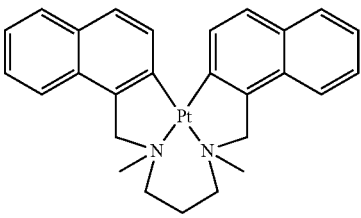

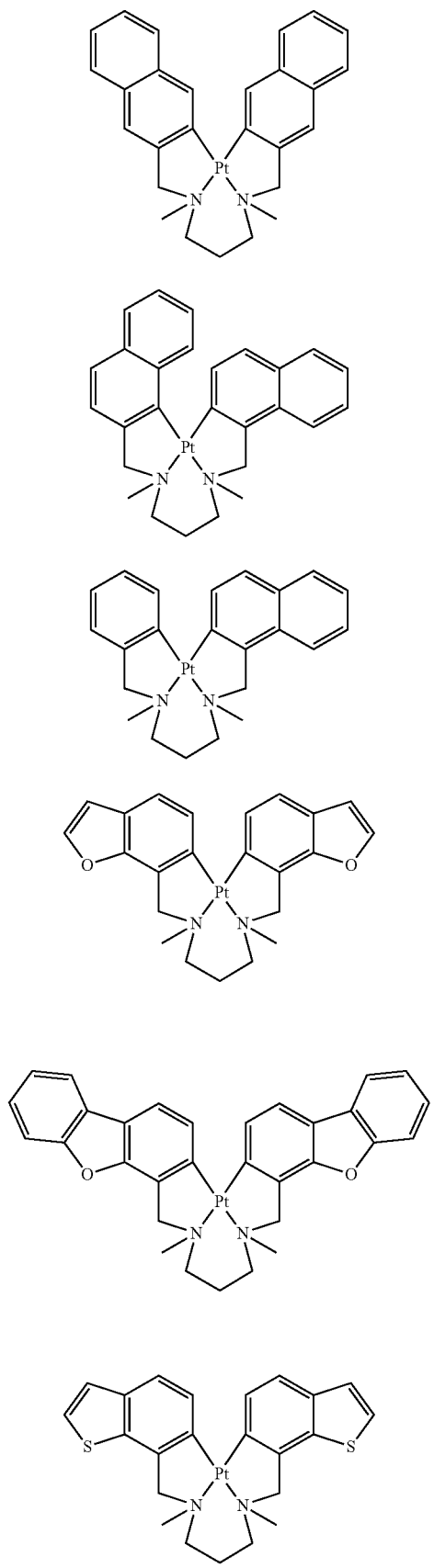
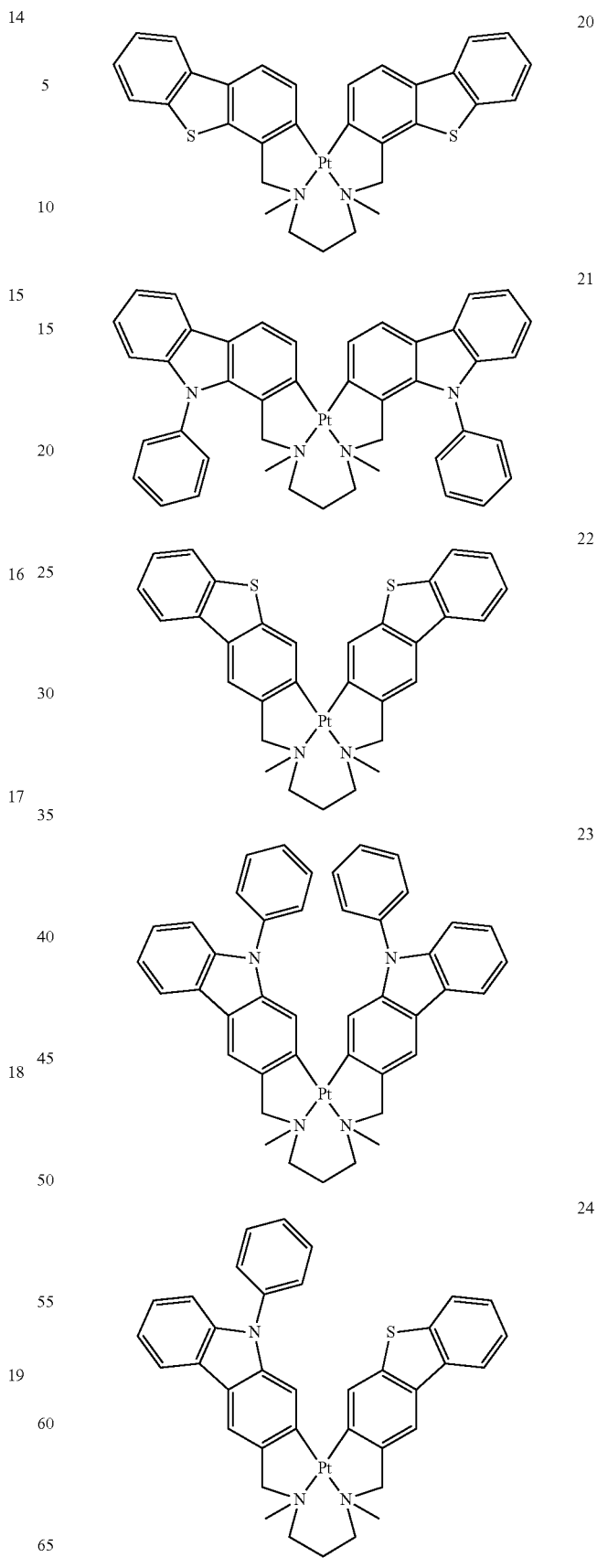

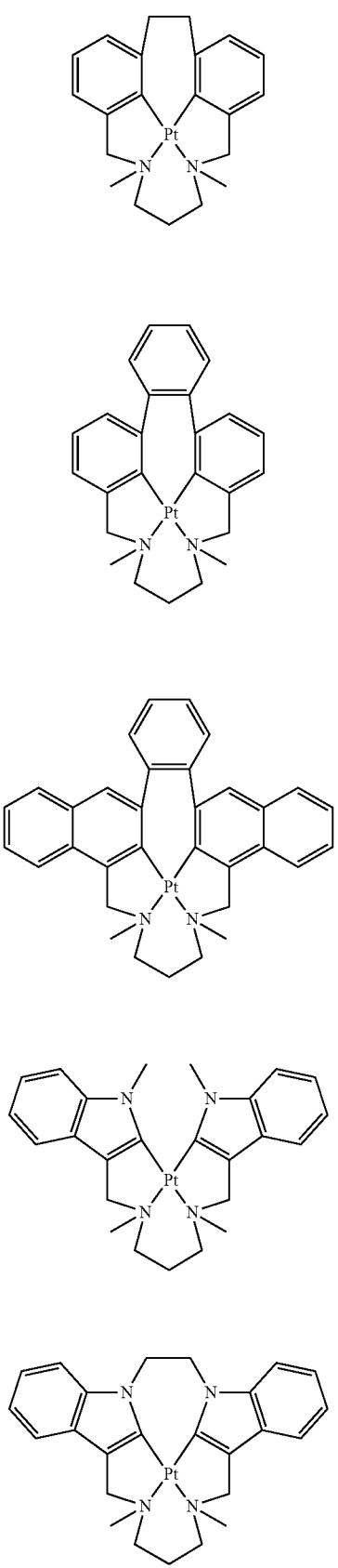

36
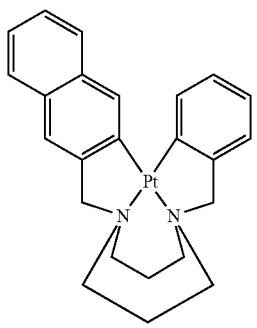
37
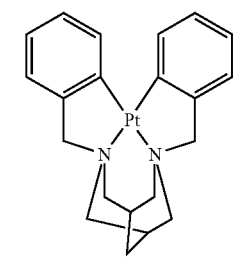
38
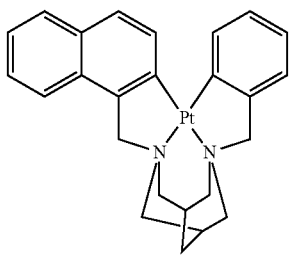
39
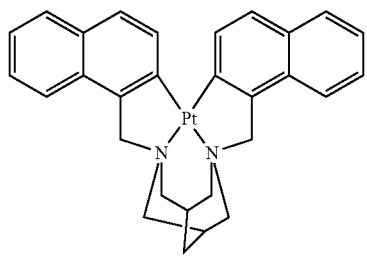
40
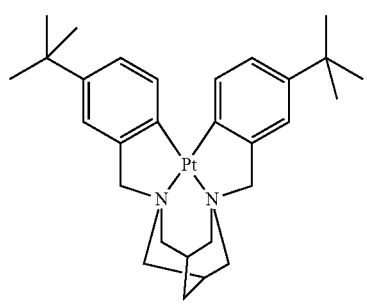
41
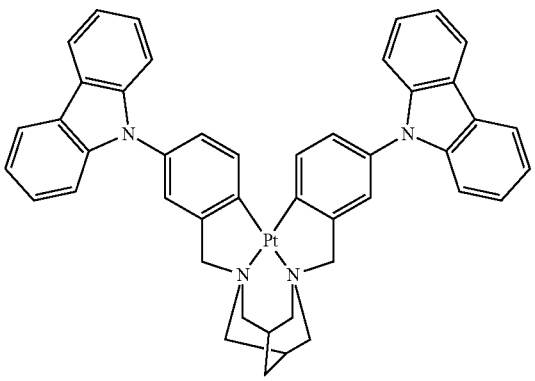
42
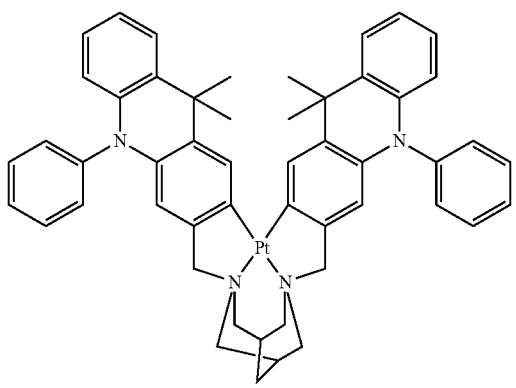
43
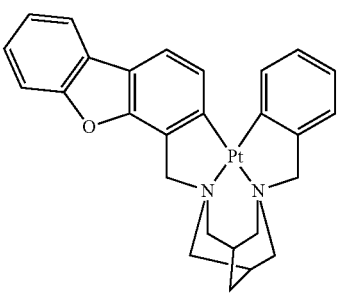
44
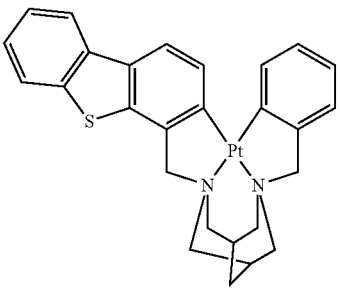

-continued
45
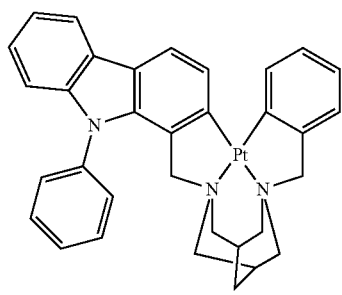
46
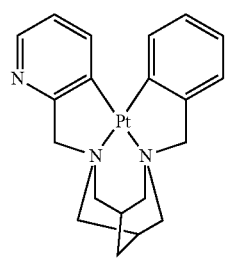
47
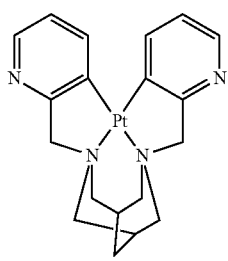
48
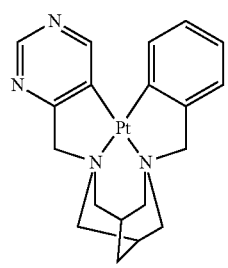
49
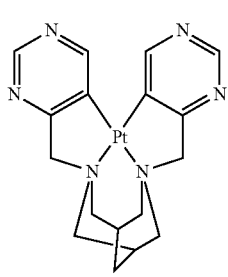
50
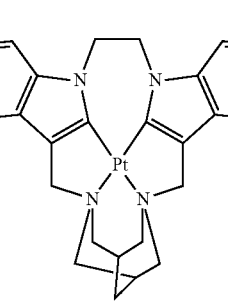
-continued
51
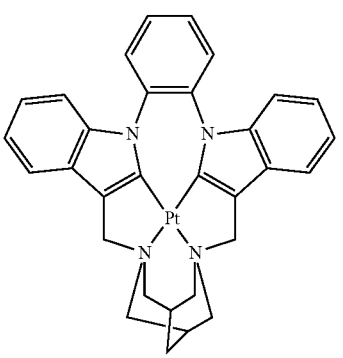
52
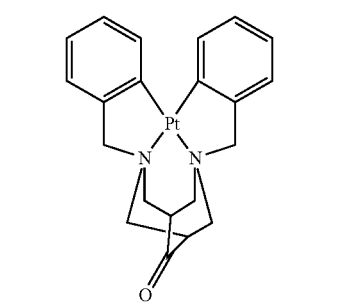
53
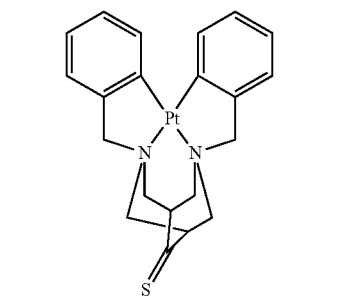
54
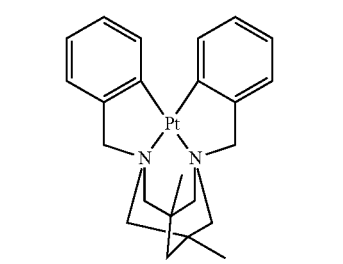
55
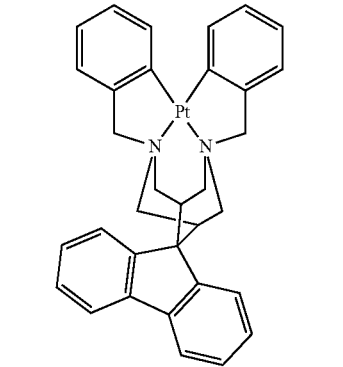

-continued
56
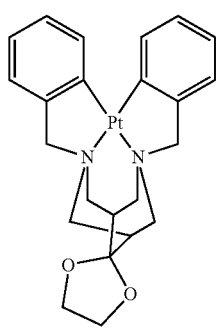
57
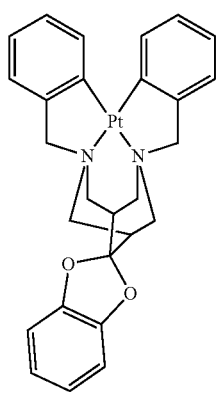
58
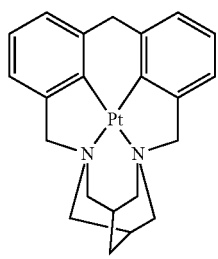
59
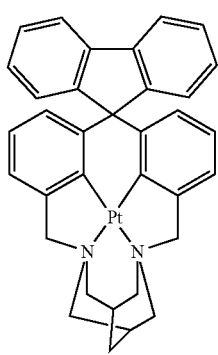
-continued
60
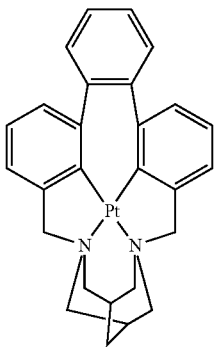
61
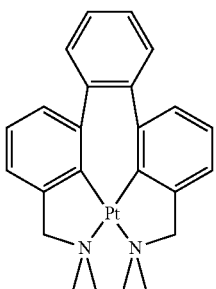
62
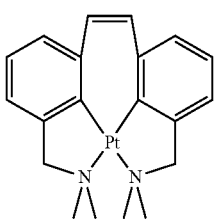
63
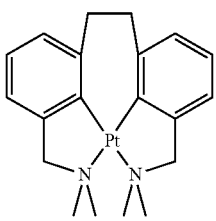
64
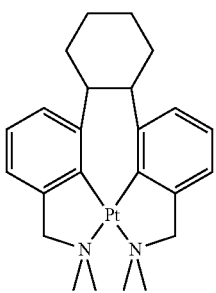

65
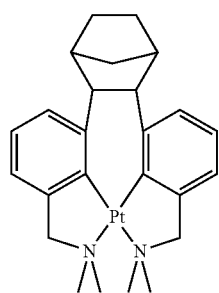
66
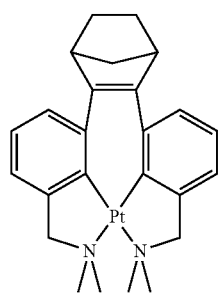
67
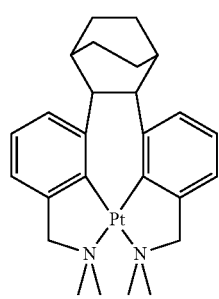
68
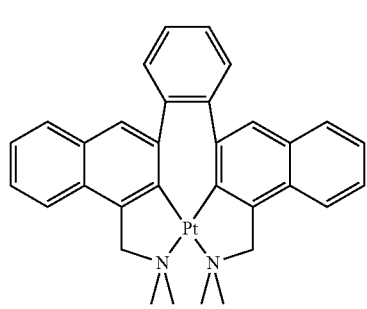
69
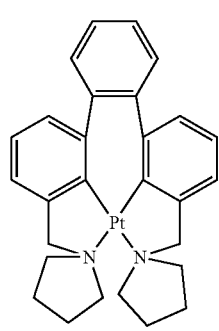
70
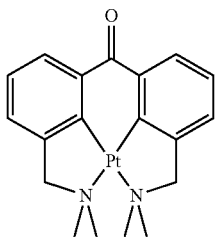
71
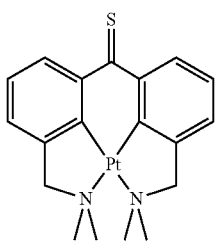
72
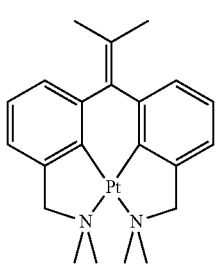
73
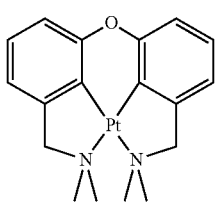
74
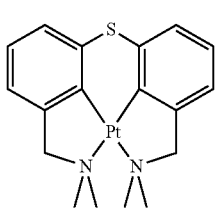
75
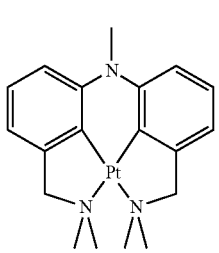

76 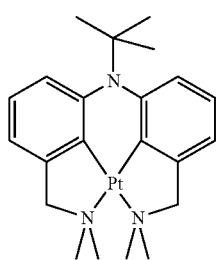
77 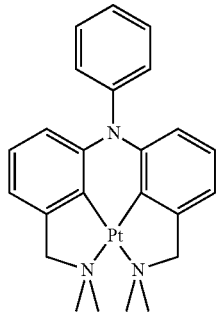
78 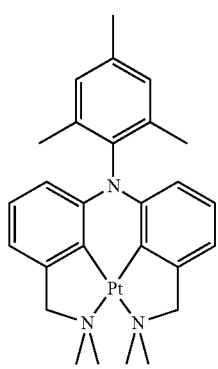
79 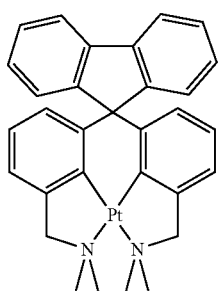
80 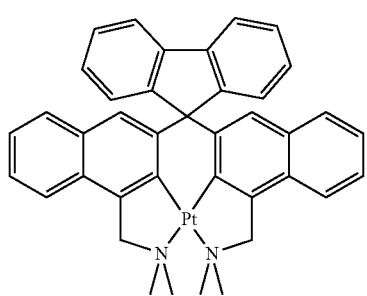
81 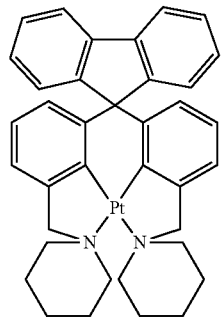
82 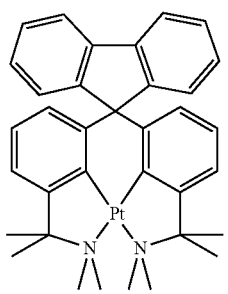
83 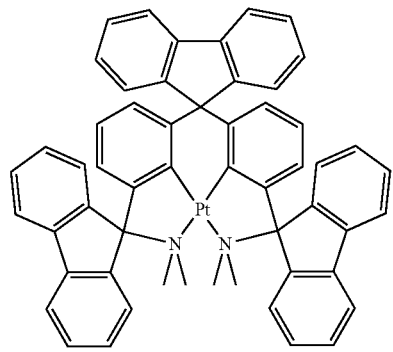
84 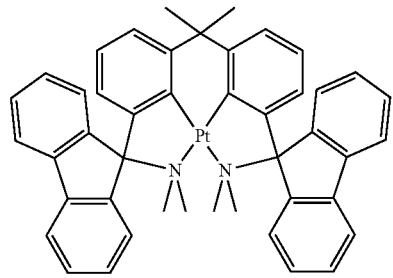
85 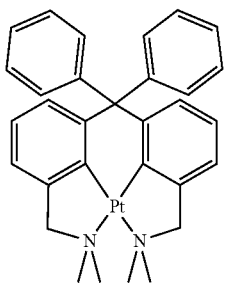

33
-continued
86
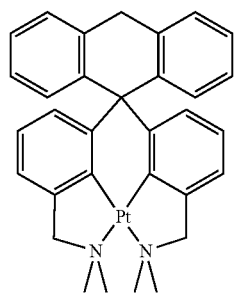
87
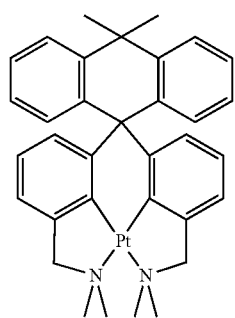
88
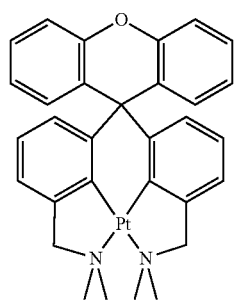
89
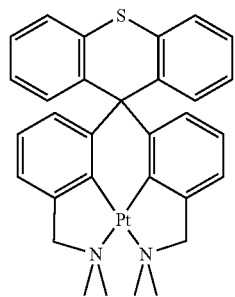
90
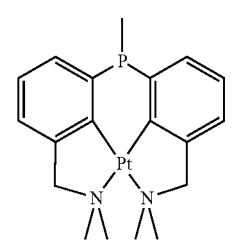
34
-continued
91
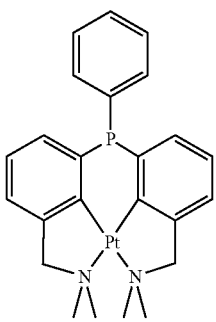
92
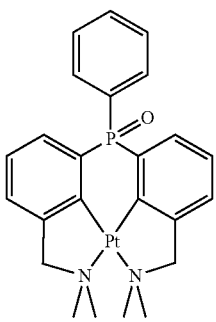
93
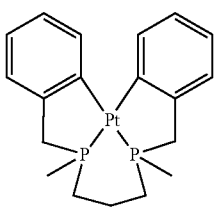
94
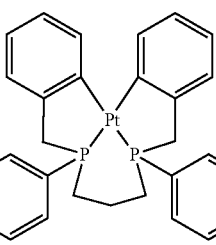
95
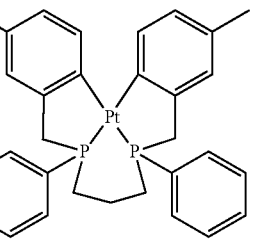
96

-continued
97 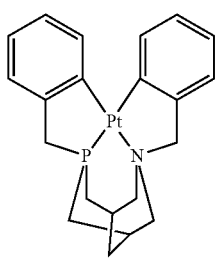
98 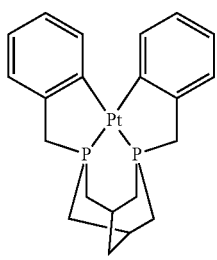
99 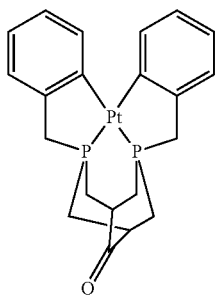
100 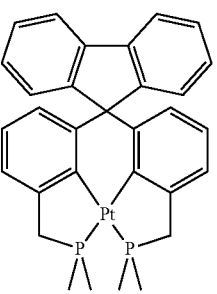
101 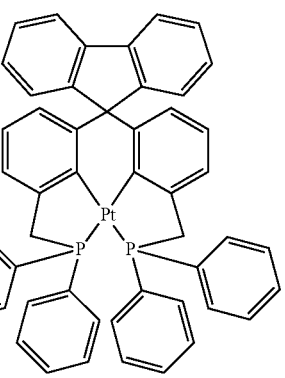
-continued
102 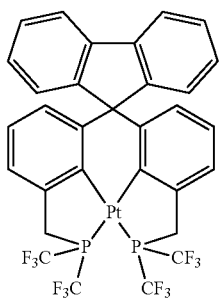
103 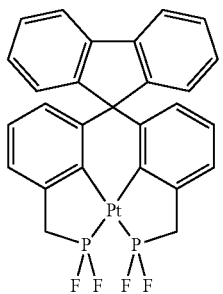
104 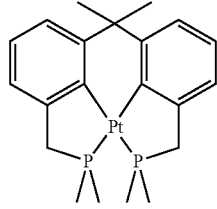
105 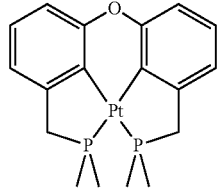
106 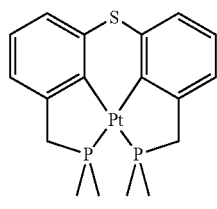
107 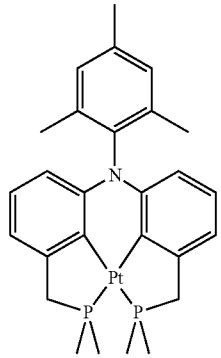

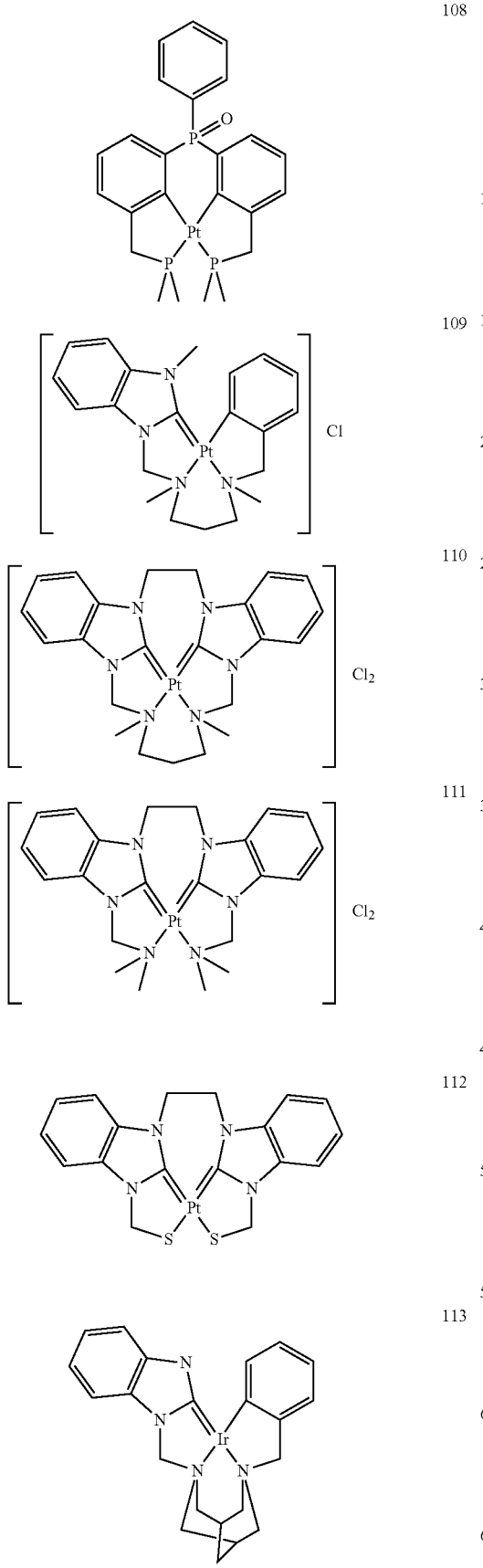

119

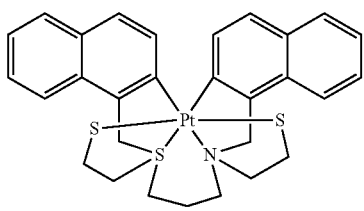

120

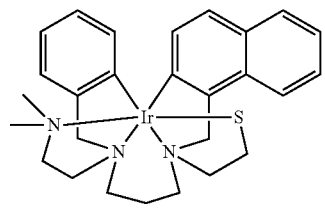

The invention likewise relates to compounds of the formula (Ia), formula (Ia)

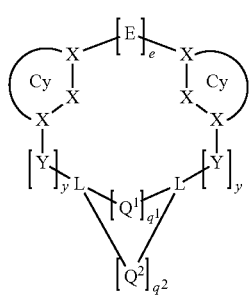

They represent the free ligands of the coordination compounds of the formula (I) and are thus important intermediates in the preparation of the metal complexes according to the invention.

The indices and symbols used are defined here as described for formula (I), and the same preferred embodiments which have already been indicated above in connection with compounds of the formula (I) apply.

The compounds of the formula (Ia) may be positively charged, negatively charged or uncharged, preferably uncharged.

The compounds of the formula (I) according to the invention can in principle be prepared by a number of different processes. However, the processes described below have proven particularly favourable.

The ligand synthesis can be carried out, for example, by reaction of a secondary amine, secondary phosphine, alcohol, thioalcohol or selenoalcohol with arylmethyl-$Y^1$ compounds, where $Y^1$ stands for a suitable leaving group (Scheme 1). Examples of leaving groups $Y^1$ are, inter alia: —OTs, —OMs, —OTf, —Cl, —Br and —I. To this end, condensation reagents, for example acid-binding assistants, or catalysts can be added. The isomers occurring on use of different ligand precursors can be separated by standard methods, such as fractional recrystallisation or chromatography.

Scheme 1:

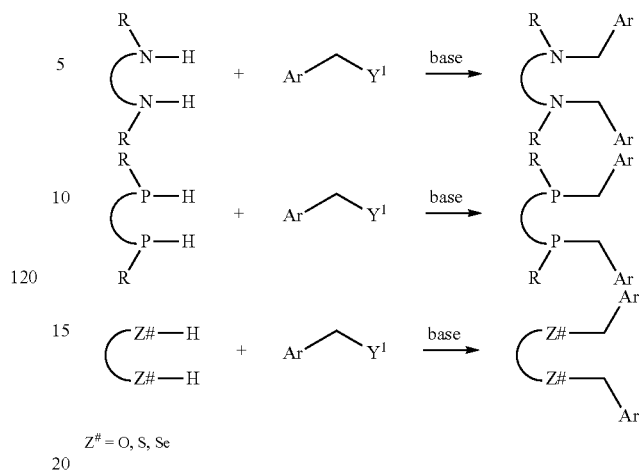

$Z^\# = O, S, Se$

In the case of the bicyclic ligands derived from bispidine, asymmetrical ligands can also be synthesised specifically in addition to symmetrical ligands by a double Mannich reaction (Scheme 2).

Scheme 2:

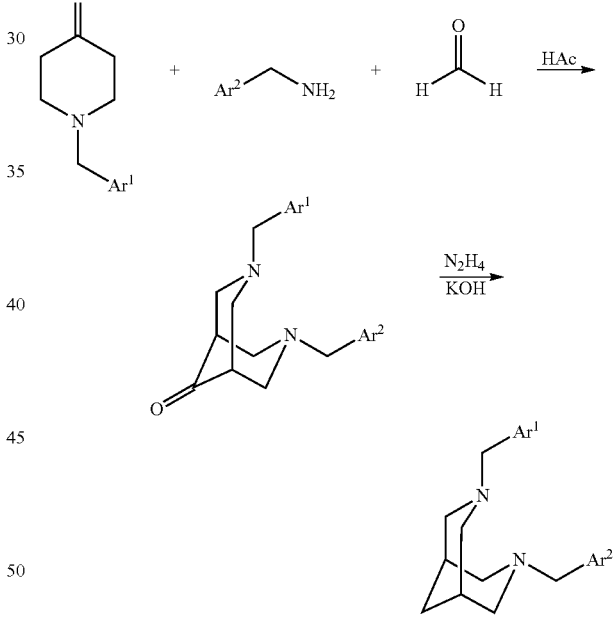

The ligand compounds shown in Scheme 3 can be obtained starting from 3,3'-halogen-substituted diarylmethanes, -amines, ethers, thioethers, etc., by the sequence: lithiation, formylation and reduction to the alcohol and subsequent transformation of the hydroxyl group into a leaving group, such as Cl, Br, I, OMs, OTs, OTf, and substitution of this leaving group by N or P nucleophiles. If the nucleophiles employed in the final step are secondary diamines, secondary aminophosphines or secondary diphosphines instead of secondary monoamines or secondary monophosphines, cyclic tetradentate ligands are obtained. Analogous reactions are possible not only with amines and phosphines, but also with alcohols, thioalcohols or selenoalcohols, where again the open-chain tetradentate ligands are obtained with monofunctional nucleophiles and the cyclic tetradentate ligands are obtained with difunctional nucleophiles.

Scheme 3:

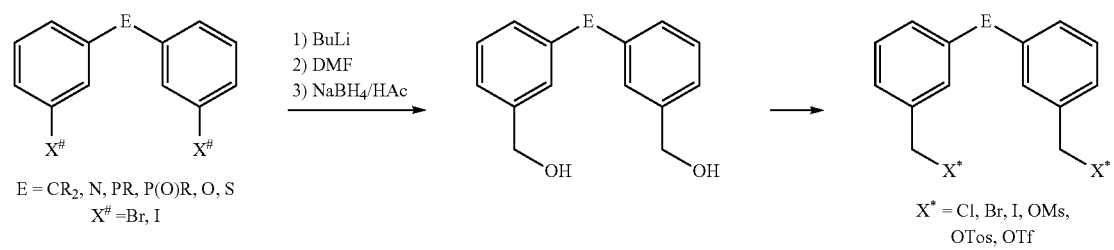

E = CR$_2$, N, PR, P(O)R, O, S
X$^\#$ =Br, I

X* = Cl, Br, I, OMs, OTos, OTf

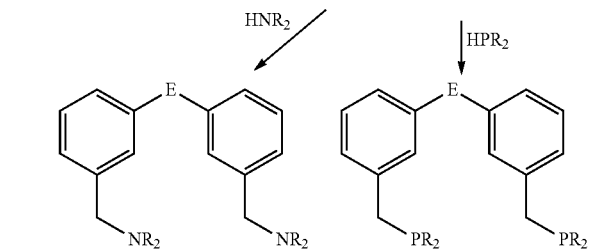

A general synthetic procedure for the preparation of the metal complexes is shown in Schemes 4 and 5.

The reaction of the ligands with a corresponding metal compound, which is usually employed as a solution of a suitable metal salt, for example K$_2$PtCl$_4$, Pt(NCMe)$_2$Cl$_2$, K$_2$PdCl$_4$, Pt(DMSO)$_2$Cl$_2$, IrCl$_3$.x H$_2$O, Na[Ir(acac)$_2$O$_2$], AuCl$_3$, or in the form of an organometallic precursor, for example Pt(CH$_3$)$_2$(DMSO)$_2$, Pt(PPh$_3$)$_4$, Ir(PPh$_3$)$_2$(CO)Cl, [Ir(COD)Cl]$_2$ or Ir(COD)$_2$BF$_4$, results in the compounds of the formula (I) according to the invention. The reaction can be carried out in the presence of acids (for example a hydrohalic acid, phosphoric acid or an organocarboxylic acid) or bases (for example organocarboxylates, carbonates, phosphates, alcoholates, alkoxides). If desired, Lewis acids (for example aluminium halides or silver salts) are added in order to activate the ortho-metallation. If desired, the intermediate compound can also be isolated as such and then converted further into the compound according to the invention. The reaction with formal elimination of HX can also be carried out in a purely thermally induced manner in solution, in the melt or as a solid-state reaction.

The processes can be employed analogously for the O-, S- or Se-containing ligands not shown in Schemes 4 and 5.

Scheme 5:

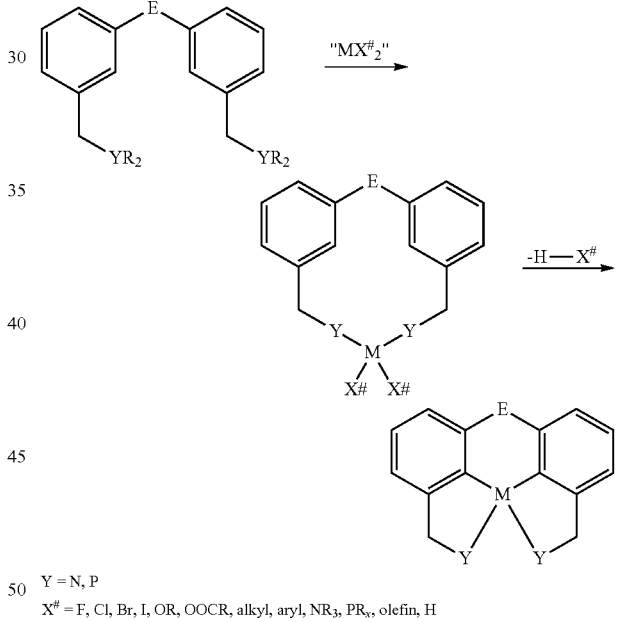

Y = N, P
X$^\#$ = F, Cl, Br, I, OR, OOCR, alkyl, aryl, NR$_3$, PR$_x$, olefin, H The invention thus relates to a process for the preparation of the ligand compounds of the formula (Ia) according to the invention, which preferably follows one of the reaction routes described in Schemes 1 to 3 above.

The invention likewise relates to a process for the preparation of the compounds according to the invention, preferably in accordance with one of the two reaction routes shown in Schemes 4 and 5, characterised in that the free ligands of the formula (Ia) are reacted with metal compounds, preferably the above-mentioned compounds.

It is furthermore possible to use metal compounds, in particular iridium compounds, which may, besides alcoholate, also carry halide and/or hydroxyl and/or ketoketonate radicals. These compounds may also be charged. Iridium compounds which are particularly suitable as starting materials Scheme 4:

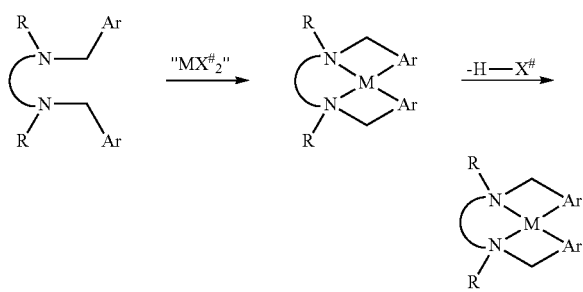

X$^\#$ = F, Cl, Br, I, OR, OOCR, alkyl, aryl, NR$_3$, PR$_x$, olefin, H are disclosed in WO 04/085449. Na[IrCl$_2$(acac)$_2$], for example, is particularly suitable.

These processes enable the compounds of the formula (I) according to the invention to be obtained in high purity, preferably greater than 99% (determined by means of $^1$H-NMR and/or HPLC).

The compounds according to the invention described above, in particular compounds which are substituted or functionalised by reactive groups, can be used as monomers for the preparation of corresponding oligomers, dendrimers or polymers.

An oligomer in the sense of this invention denotes a compound which has three to nine recurring units. A polymer in the sense of the invention is taken to mean a compound which has ten or more recurring units.

The invention therefore furthermore relates to oligomers, polymers or dendrimers comprising one or more compounds of the formula (I), where the compounds according to the invention have one or more bonds to the polymer, oligomer or dendrimer. These bonds to adjacent monomer units in the polymer, oligomer or dendrimer can occur at the site of any desired bond to $R^B$, $R^C$ or $R^1$. Depending on the linking of the compound of the formula (I), the compound is therefore a constituent of a side chain of the oligomer or polymer or a constituent of the main chain. The polymers, oligomers or dendrimers may be conjugated, partially conjugated or non-conjugated. The oligomers or polymers may be linear, branched or dendritic.

For the preparation of the oligomers or polymers, the functionalised compounds of the formula (I) are homopolymerised or copolymerised with further monomers. Preference is given to copolymers, where the compound of the formula (I) is preferably present in a proportion of 0.01 to 50 mol %, particularly preferably in a proportion of 0.1 to 20 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The proportion of these units in total is preferably in the region of at least 50 mol %. The polymers, oligomers and dendrimers may also comprise further units, for example hole-transport units, in particular those based on triarylamines, and/or electron-transport units.

Polymers, oligomers or dendrimers of this type comprising compounds of the formula (I) can be used in electronic devices, in particular in OLEDs, in particular in the emitter layer. A polymeric emitter layer can be produced, for example, by coating from solution (spin coating or printing processes).

The invention furthermore relates to the use of the compounds of the formula (I) or the oligomers, polymers or dendrimers described above in an electronic device, preferably as emitting compound. Preferred embodiments of electronic devices are organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), particularly preferably organic electroluminescent devices (OLEDs).

The invention furthermore relates to the use of the compounds according to the invention as charge-transport material and/or charge-injection material, preferably in a corresponding layer of an electronic device. The layer can be, for example, a hole-transport layer, hole-injection layer, electron-transport layer or electron-injection layer. The use of the compounds according to the invention as charge-blocking material or as matrix material is also possible.

The invention likewise relates to electronic devices, preferably organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), particularly preferably organic electroluminescent devices, comprising one or more compounds of the formula (I). The electronic device here comprises an anode, a cathode and at least one layer which comprises at least one organic or organometallic compound. However, the device may additionally also comprise inorganic materials.

The compounds according to the invention are preferably present in the electronic device within one or more layers.

The invention thus also relates to a layer comprising at least one compound of the formula (I).

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. An interlayer which has, for example, an exciton-blocking function may likewise be introduced between two emitting layers. However, it should be pointed out that each of these layers does not necessarily have to be present. These layers may also comprise, inter alia, compounds of the formula (I).

In a preferred embodiment of the invention, the compounds according to the invention are employed as emitters in an emitting layer or as charge-transport compounds in a charge-transport layer. The organic electroluminescent device may comprise one emitting layer or a plurality of emitting layers, where at least one layer, which may be an emitting layer or another layer, comprises at least one compound of the formula (I). If a plurality of emission layers are present, these preferably have in total a plurality of emission maxima between 380 nm and 750 nm, resulting overall in white emission, where white emission is characterised by CIE colour coordinates in the range from 0.28/0.29 to 0.45/0.41, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013).

If the compound of the formula (I) is employed as emitting compound in an emitting layer, it is preferably employed in combination with one or more matrix materials. However, the compound may also be employed as pure substance in an emitting layer.

The mixture of the emitter material and the matrix material comprises between 1 and 99% by vol., preferably between 2 and 90% by vol., particularly preferably between 3 and 40% by vol., especially preferably between 5 and 15% by vol., of the emitter compound, based on the entire mixture of emitter and matrix material. Correspondingly, the mixture comprises between 99 and 1% by vol., preferably between 98 and 10% by vol., particularly preferably between 97 and 60% by vol., especially preferably between 95 and 85% by vol., of the matrix material, based on the entire mixture of emitter and matrix material.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the emitting layer of the electronic device comprises two or more different, particularly preferably two different, matrix compounds (mixed-matrix system). If the emitting layer comprises two different matrix materials, these are preferably present in a ratio of 1:10 to 1:1, particularly preferably in a ratio of 1:4 to 1:1. The mixed-matrix systems may comprise one or more different dopants. Preferred dopants are the compounds of the formula (I) according to the invention. In accordance with the invention, the dopant compound or the dopant compounds together have a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Preferred matrix materials are carbazole derivatives (for example CBP (N,N-biscarbazolylbiphenyl) or compounds in accordance with WO 05/039246, US 2005/0069729, JP 2004/288381, EP 1205527 or WO 08/086,851), triarylamines, azacarbazoles (for example in accordance with EP 1617710, EP 1617711, EP 1731584, JP 2005/347160), indolocarbazole derivatives, for example in accordance with WO 07/063,754 or WO 08/056,746, ketones (for example in accordance with WO 04/093207 or in accordance with DE 102008033943), phosphine oxides, sulfoxides and sulfones (for example in accordance with WO 05/003253), oligophenylenes, aromatic amines (for example in accordance with US 2005/0069729), bipolar matrix materials (for example in accordance with WO 07/137,725), silanes (for example in accordance with WO 05/111172), azaboroles or boronic esters, for example in accordance with WO 06/117052, triazine derivatives, for example in accordance with DE 102008036982, WO 07/063,754 or WO 08/056,746, zinc complexes (for example in accordance with DE 102007053771), aluminium complexes (for example BAlq), diazasilole and tetraazasilole derivatives, for example in accordance with DE 102008056688, indenocarbazole derivatives, for example in accordance with the unpublished applications DE 102009023155.2 and DE 102009031021.5, or diazaphospholes, for example in accordance with the unpublished application DE 102009022858.6.

The materials preferably employed for the respective functions or in the respective functional layers in the electronic devices according to the invention are shown below.

Preferred fluorescent emitter materials are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An aryl amine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter materials are selected from indenofluorenamines or indenofluorenediamines, for example in accordance with WO 06/122630, benzoindenofluorenamines or benzoindenofluorenediamines, for example in accordance with WO 08/006,449, and dibenzoindenofluorenamines or dibenzoindenofluorenediamines, for example in accordance with WO 07/140,847. Examples of emitter materials from the class of the styrylamines are substituted or unsubstituted tristilbenamines or the emitter materials described in WO 06/000388, WO 06/058737, WO 06/000389, WO 07/065,549 and WO 07/115,610. Preference is furthermore given to the condensed hydrocarbons disclosed in the application DE 102008035413.

Suitable emitter materials are furthermore the structures depicted in the following table, and the derivatives of these structures disclosed in JP 06/001973, WO 04/047499, WO 06/098080, WO 07/065,678, US 2005/0260442 and WO 04/092111.

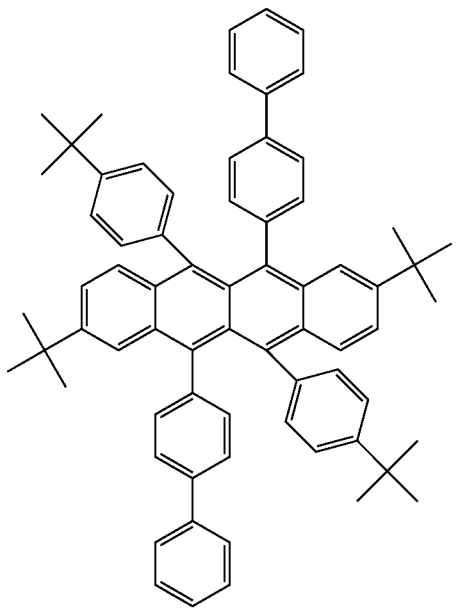 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]
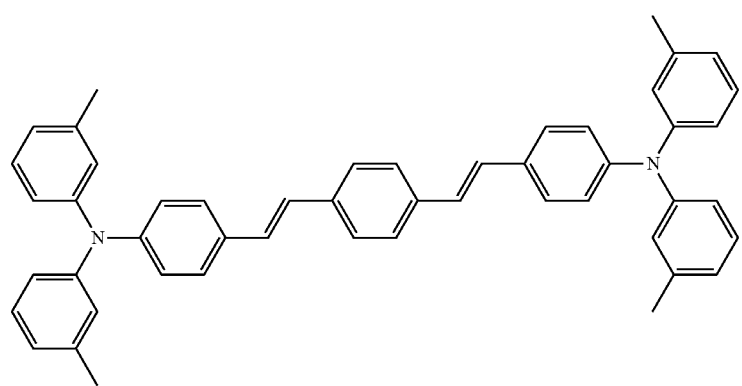 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]
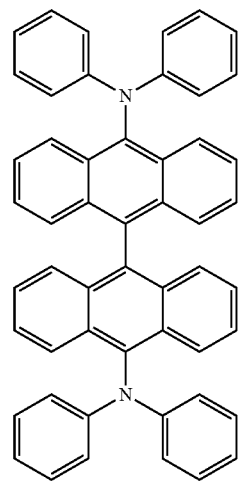 [SMILES: c1ccc(N(c2ccccc2)c2c3ccccc3c(-c3c4ccccc4c(N(c4ccccc4)c4ccccc4)c4ccccc34)c3ccccc23)cc1]

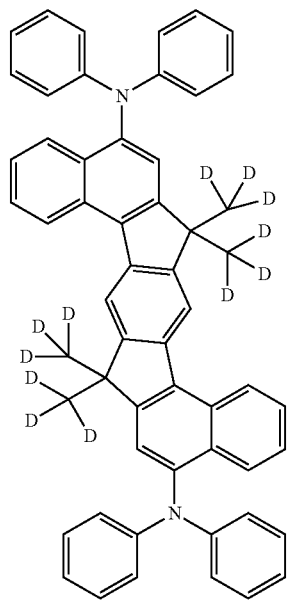 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]
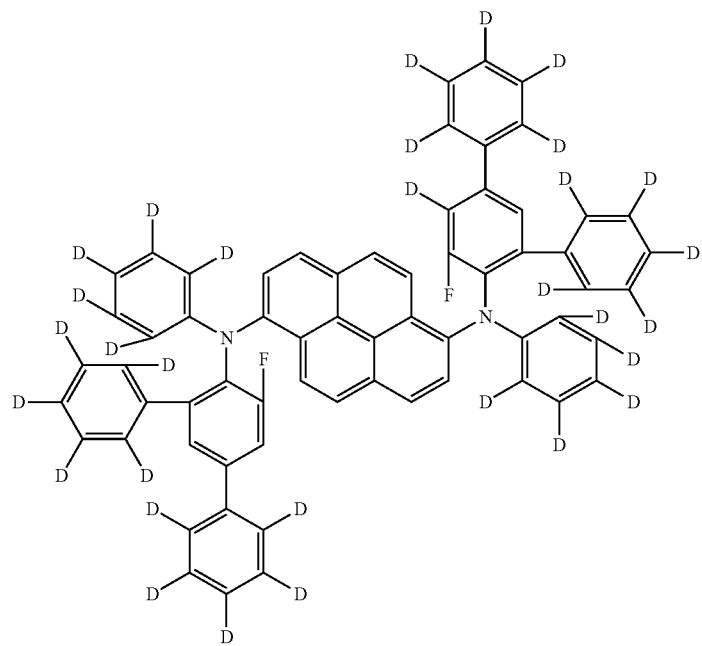 [SMILES: [2H]c1c([2H])c([2H])c(-c2cc(F)c(N(c3c([2H])c([2H])c([2H])c([2H])c3[2H])c3ccc4ccc5c(N(c6c([2H])c([2H])c([2H])c([2H])c6[2H])c6c(-c7c([2H])c([2H])c([2H])c([2H])c7[2H])cc(-c7c([2H])c([2H])c([2H])c([2H])c7[2H])c([2H])c6F)ccc6ccc3c4c65)c(-c3c([2H])c([2H])c([2H])c([2H])c3[2H])c2)c([2H])c1[2H]]
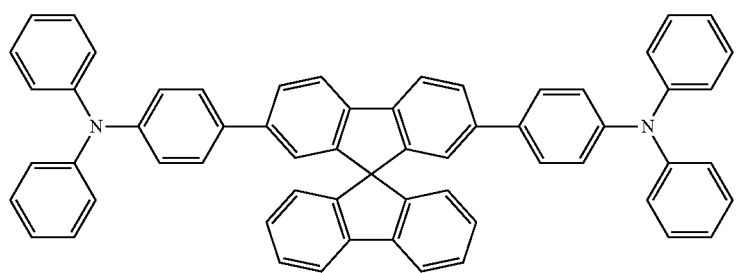 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]

-continued
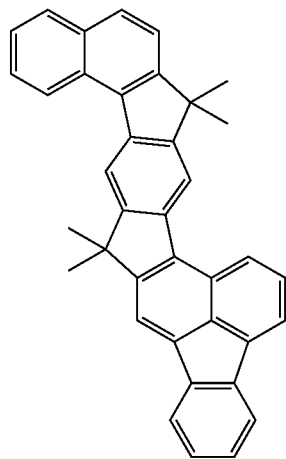 [SMILES: CC1(C)c2cc3c(cc2-c2c1ccc1ccccc21)C(C)(C)c1cc2c4c(cccc4c1-3)-c1ccccc1-2]
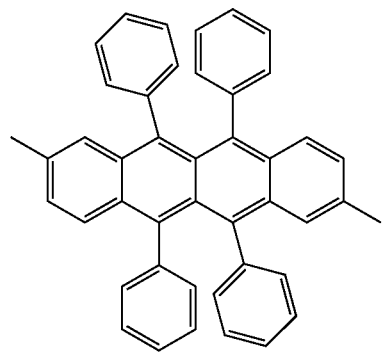
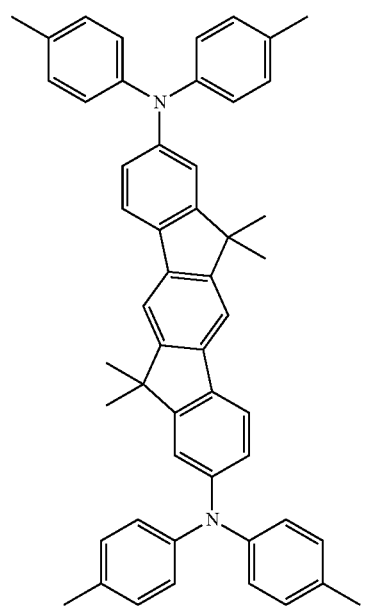

-continued
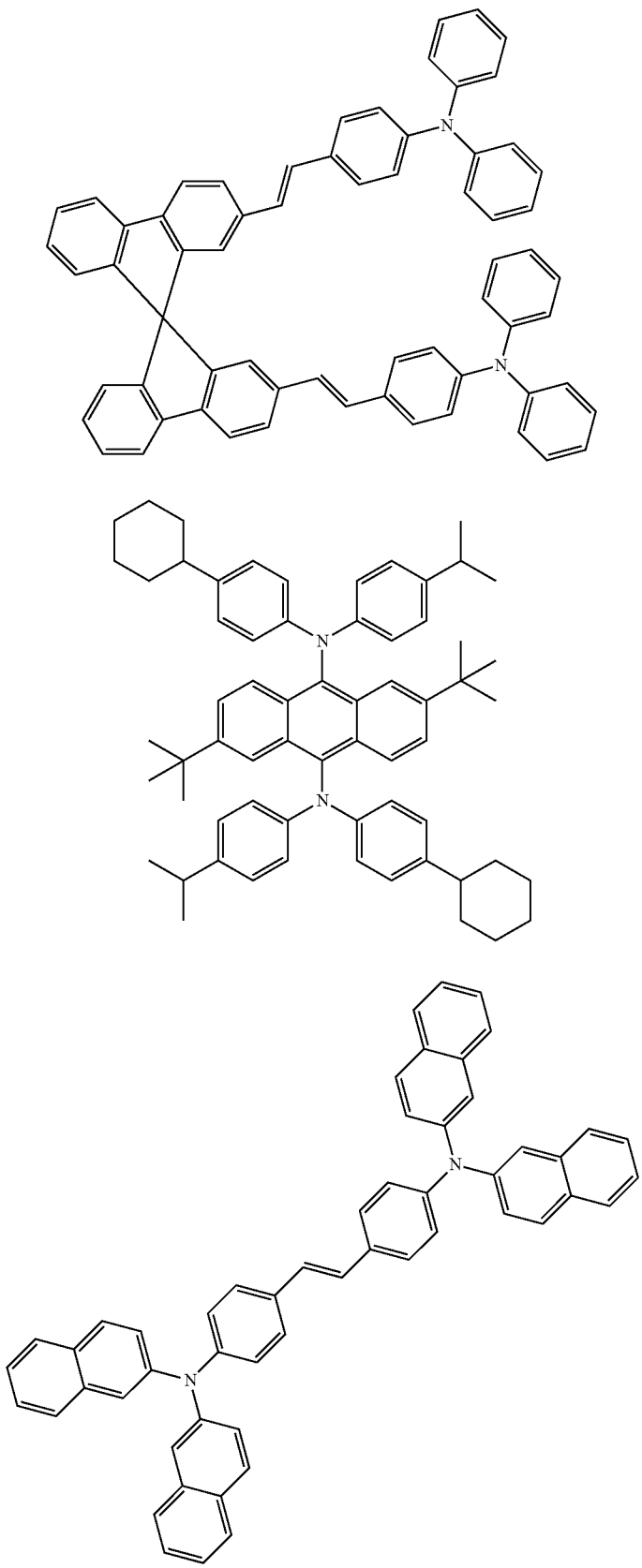

-continued
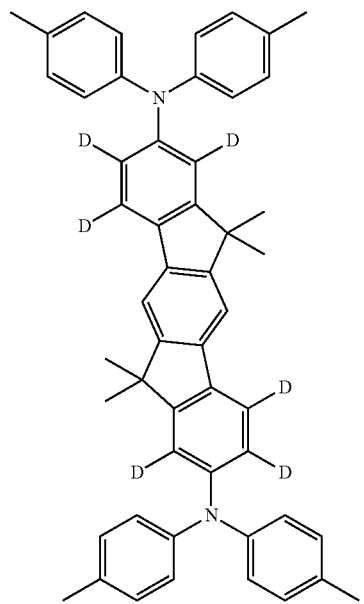
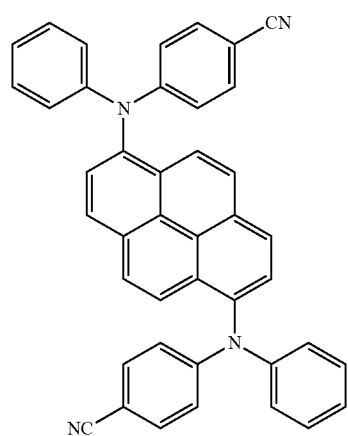 [SMILES: N#Cc1ccc(N(c2ccccc2)c2ccc3ccc4c(N(c5ccccc5)c5ccc(C#N)cc5)ccc5ccc2c3c54)cc1]

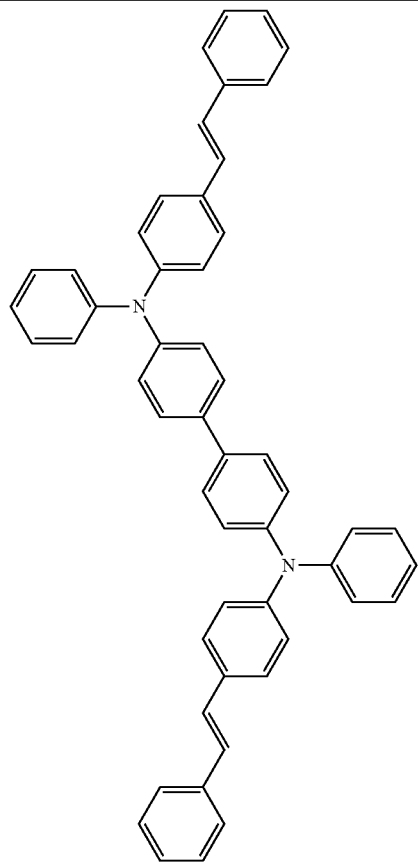
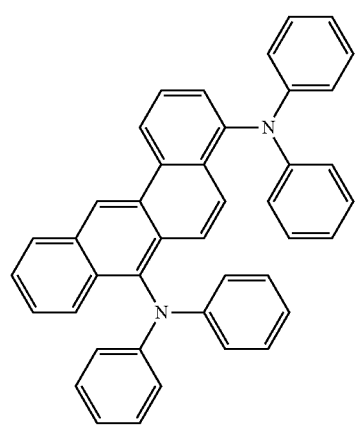 [SMILES: c1ccc(N(c2ccccc2)c2cccc3c2ccc2c(N(c4ccccc4)c4ccccc4)c4ccccc4cc23)cc1]

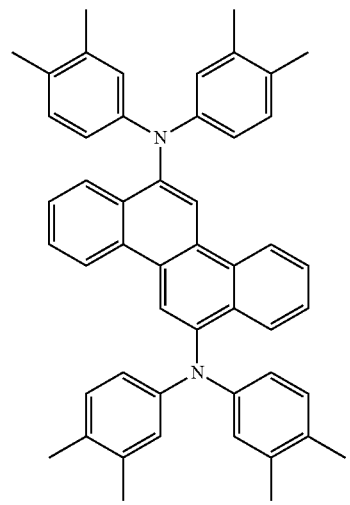
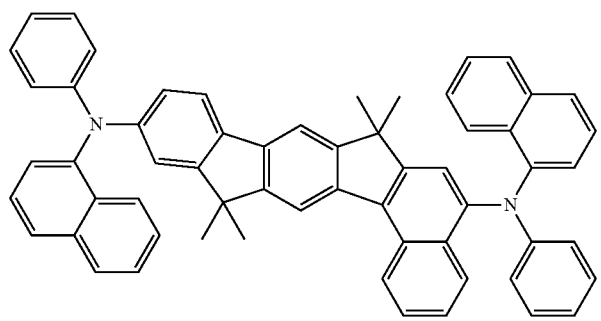 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
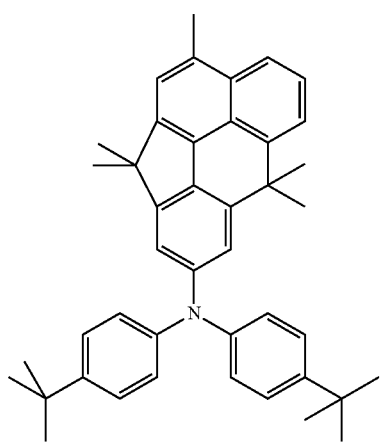 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]

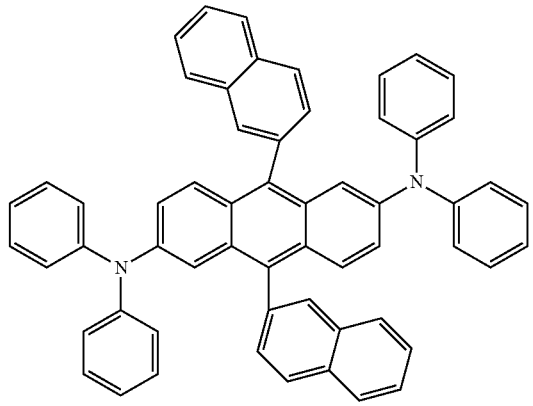 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
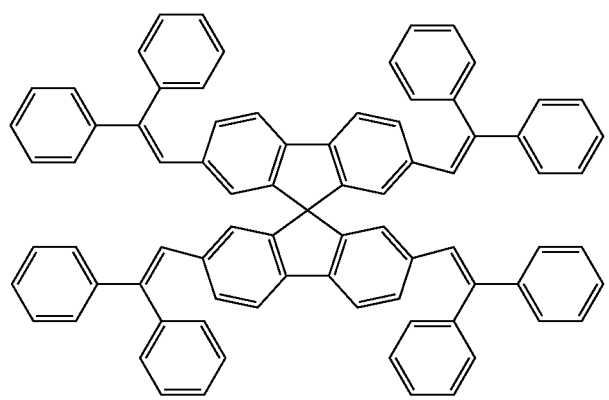 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]
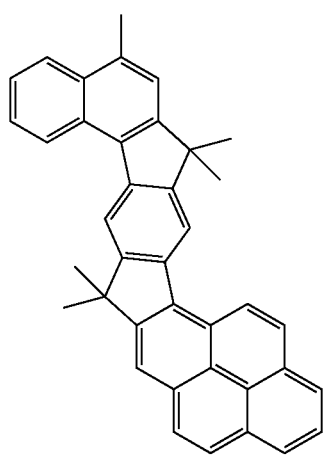 [SMILES: Cc1cc2c(c3ccccc13)-c1cc3c(cc1C2(C)C)-c1c(cc2ccc4cccc5ccc1c2c45)C3(C)C]

-continued
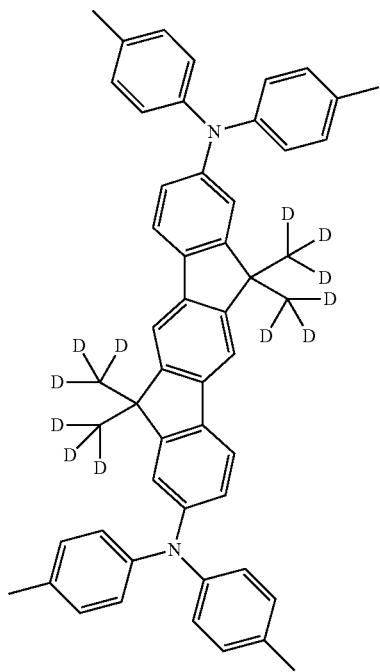
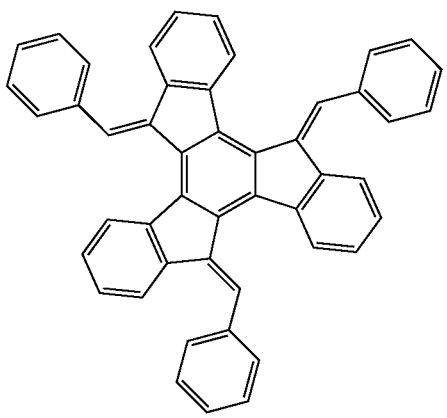 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]
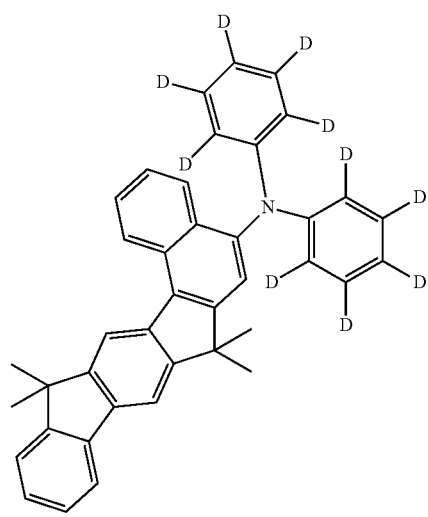 [SMILES: [2H]c1c([2H])c([2H])c(N(c2c([2H])c([2H])c([2H])c([2H])c2[2H])c2cc3c(c4ccccc24)-c2cc4c(cc2C3(C)C)-c2ccccc2C4(C)C)c([2H])c1[2H]]

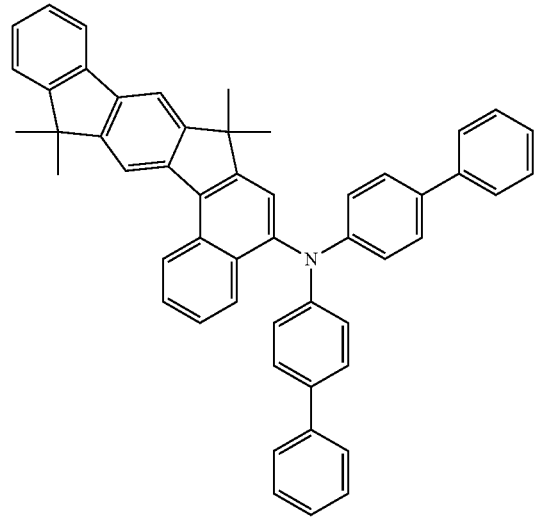 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]
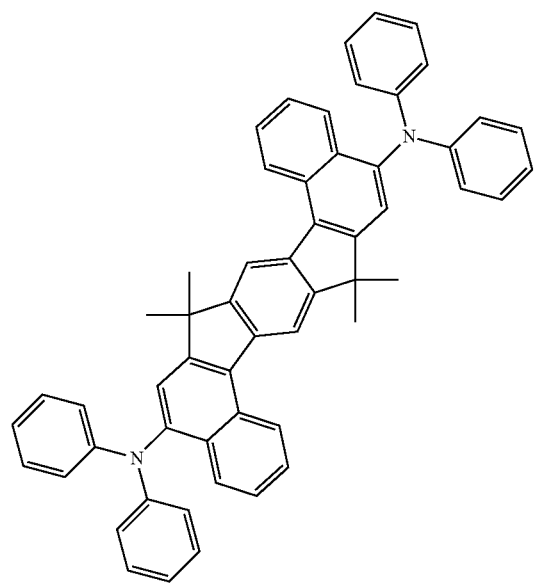 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]
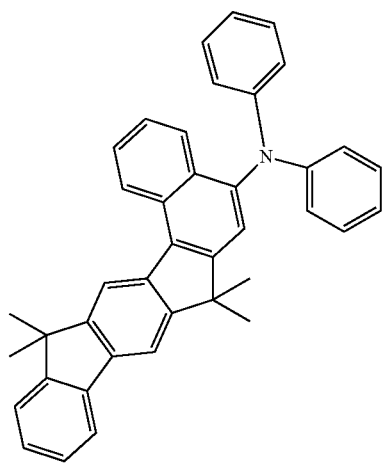 [SMILES: CC1(C)c2ccccc2-c2cc3c(cc21)-c1c(cc(N(c2ccccc2)c2ccccc2)c2ccccc12)C3(C)C]

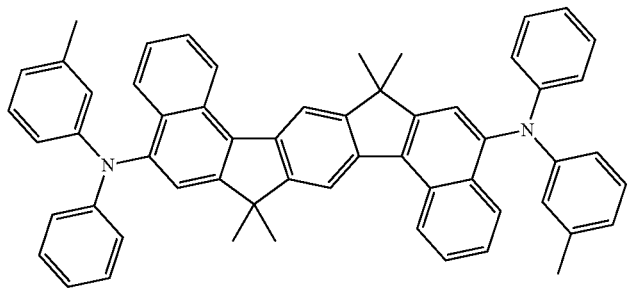 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
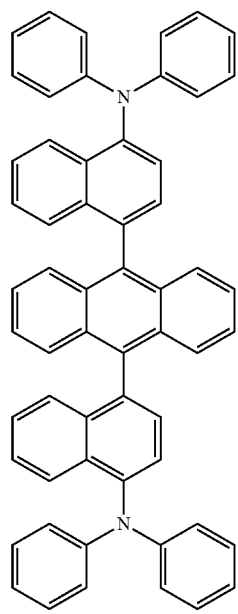 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]
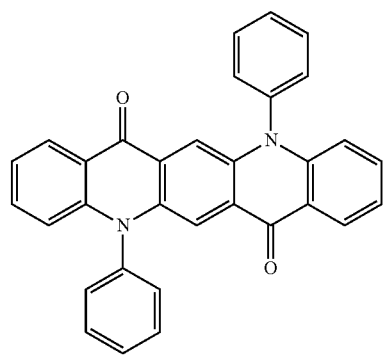 [SMILES: O=c1c2ccccc2n(-c2ccccc2)c2cc3c(=O)c4ccccc4n(-c4ccccc4)c3cc12]

-continued
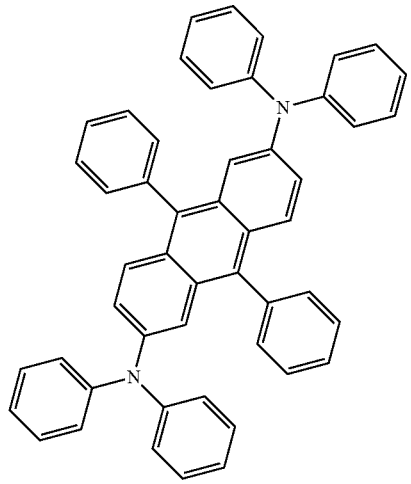 [SMILES: c1ccc(-c2c3ccc(N(c4ccccc4)c4ccccc4)cc3c(-c3ccccc3)c3ccc(N(c4ccccc4)c4ccccc4)cc23)cc1]
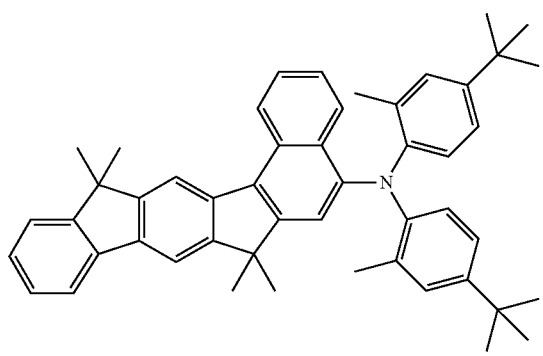 [SMILES: Cc1cc(C(C)(C)C)ccc1N(c1ccc(C(C)(C)C)cc1C)c1cc2c(c3ccccc13)-c1cc3c(cc1C2(C)C)-c1ccccc1C3(C)C]
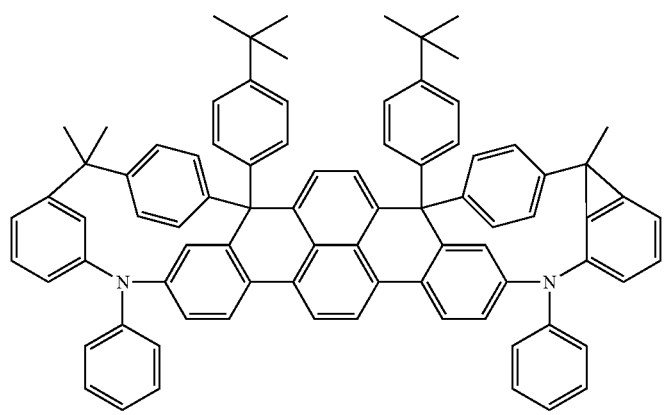 [SMILES: CC(C)(C)c1ccc(C23c4ccc(cc4)C(C)(C)c4cccc(c4)N(c4ccccc4)c4ccc(c2c4)-c2ccc4c5c(ccc3c25)C2(c3ccc(C(C)(C)C)cc3)c3ccc(cc3)C3(C)c5cccc(c53)N(c3ccccc3)c3ccc-4c2c3)cc1]

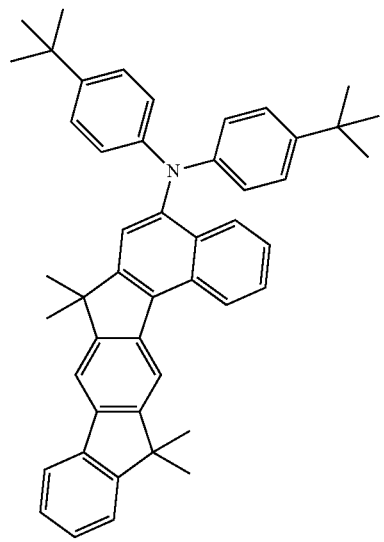 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
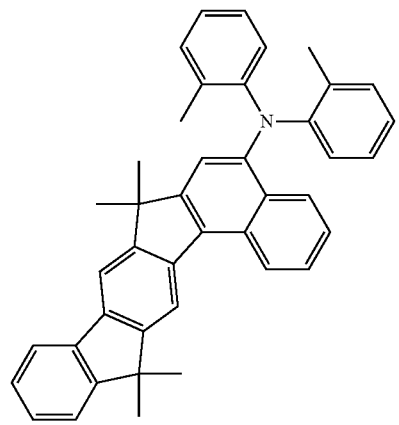 [SMILES: Cc1ccccc1N(c1ccccc1C)c1cc2c(c3ccccc13)-c1cc3c(cc1C2(C)C)-c1ccccc1C3(C)C]
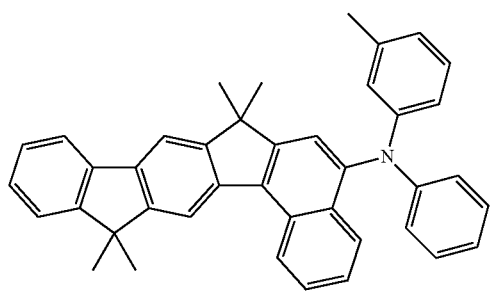 [SMILES: Cc1cccc(N(c2ccccc2)c2cc3c(c4ccccc24)-c2cc4c(cc2C3(C)C)-c2ccccc2C4(C)C)c1]
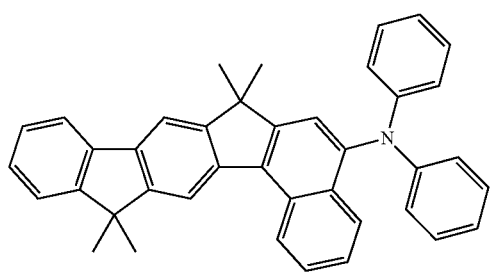 [SMILES: CC1(C)c2ccccc2-c2cc3c(cc21)-c1c(cc(N(c2ccccc2)c2ccccc2)c2ccccc12)C3(C)C]

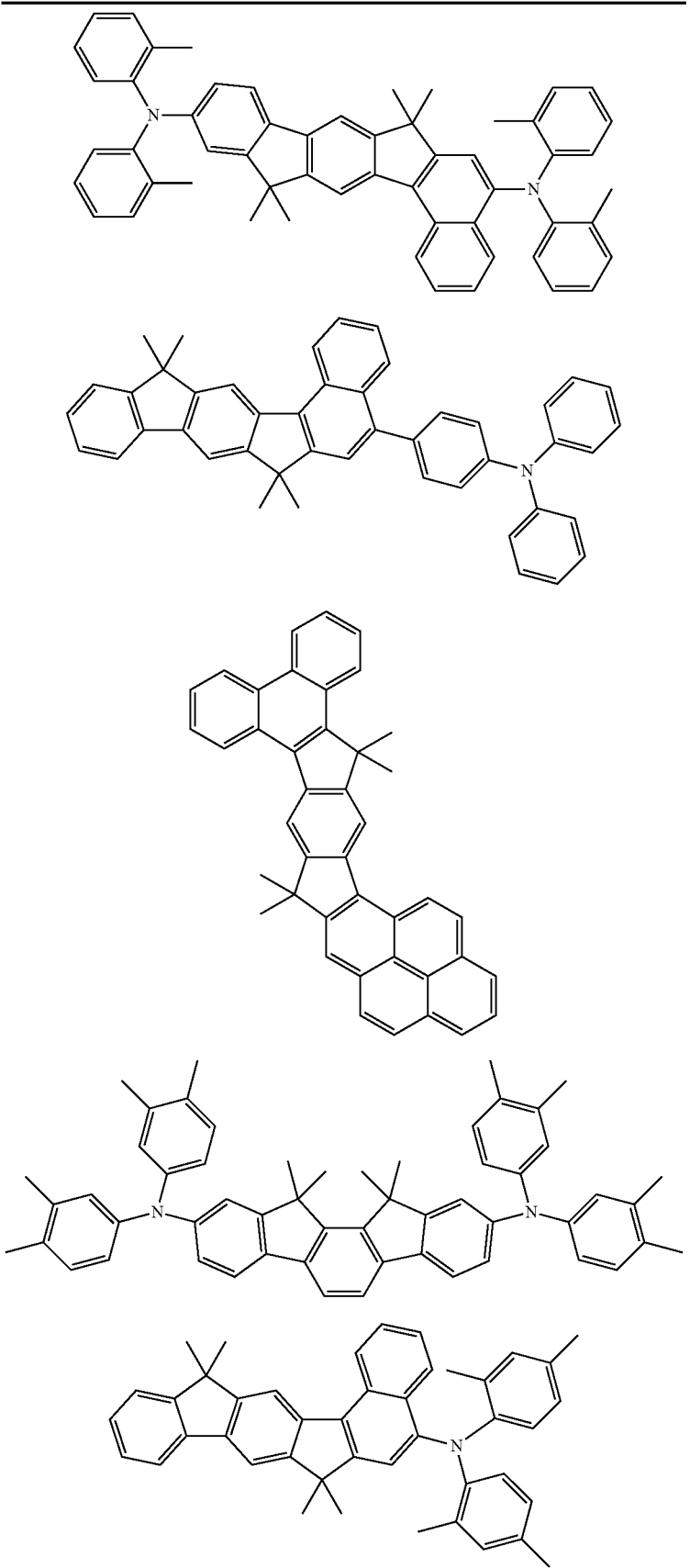

-continued
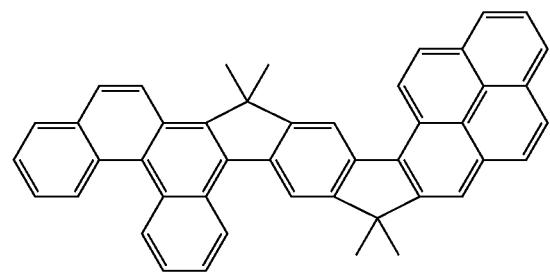 [SMILES: CC1(C)c2cc3c(cc2-c2c1cc1ccc4cccc5ccc2c1c45)C(C)(C)c1c-3c2ccccc2c2c1ccc1ccccc12]
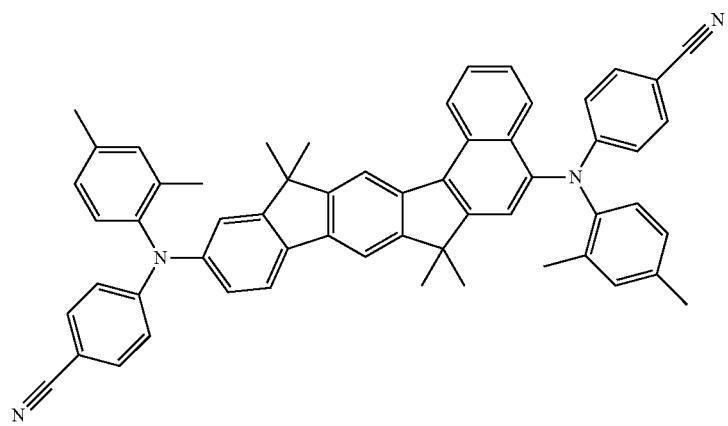 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]
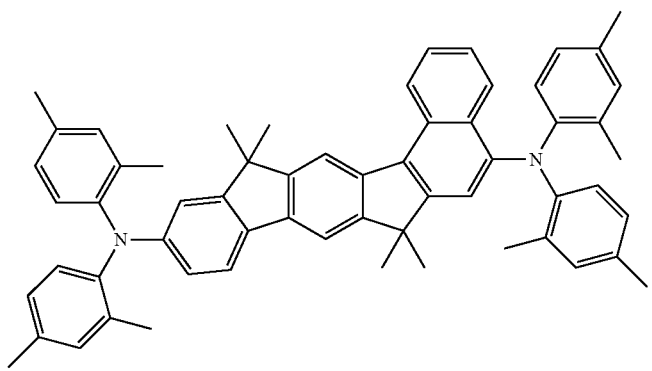
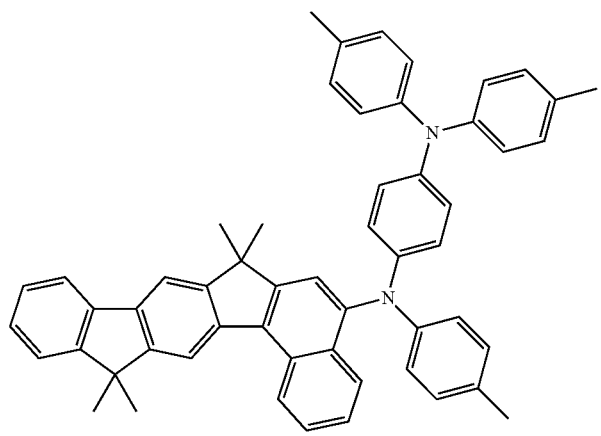 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]

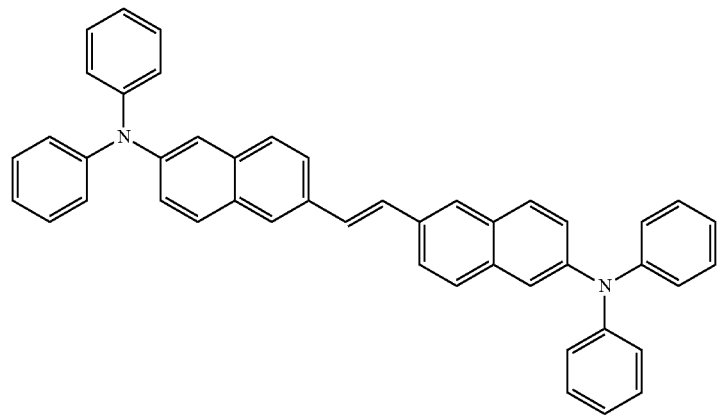 [SMILES: C(=C\c1ccc2cc(N(c3ccccc3)c3ccccc3)ccc2c1)/c1ccc2cc(N(c3ccccc3)c3ccccc3)ccc2c1]

Matrix materials which can be used, preferably for fluorescent dopants, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-transport compounds (for example in accordance with WO 04/058911), the electron-transport compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145,239). Suitable matrix materials are furthermore preferably the compounds according to the invention. Apart from the compounds according to the invention, particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 04/018587, WO 08/006,449, U.S. Pat. No. 5,935,721, US 2005/0181232, JP 2000/273056, EP 681019, US 2004/0247937 and US 2005/0211958.

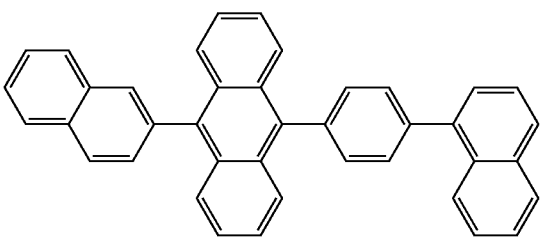 [SMILES: c1ccc2cc(-c3c4ccccc4c(-c4ccc(-c5cccc6ccccc56)cc4)c4ccccc34)ccc2c1]

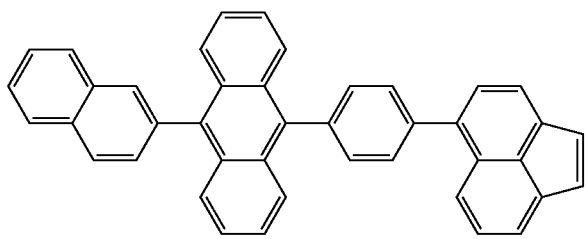 [SMILES: C1=Cc2ccc(-c3ccc(-c4c5ccccc5c(-c5ccc6ccccc6c5)c5ccccc45)cc3)c3cccc1c23]

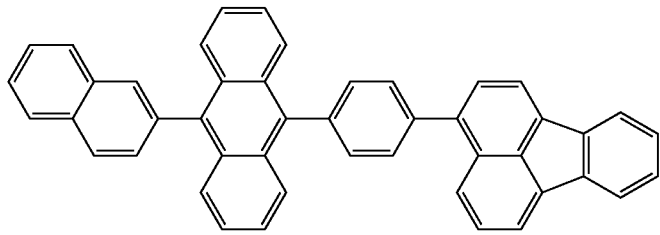 [SMILES: c1ccc2c(c1)-c1cccc3c(-c4ccc(-c5c6ccccc6c(-c6ccc7ccccc7c6)c6ccccc56)cc4)ccc-2c13]
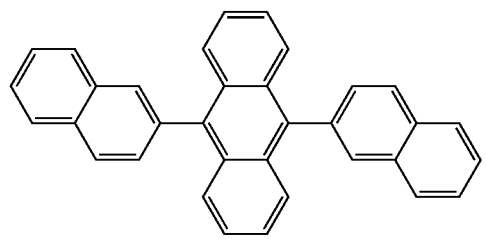 [SMILES: c1ccc2cc(-c3c4ccccc4c(-c4ccc5ccccc5c4)c4ccccc34)ccc2c1]
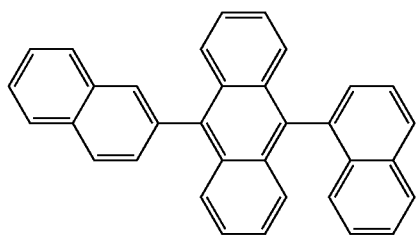 [SMILES: c1ccc2cc(-c3c4ccccc4c(-c4cccc5ccccc45)c4ccccc34)ccc2c1]
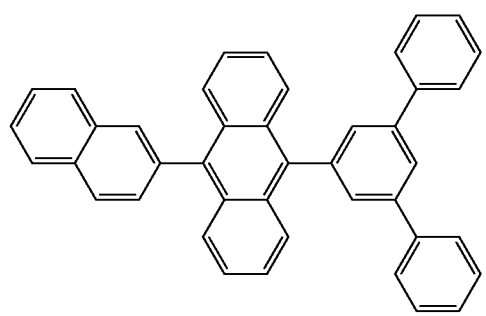 [SMILES: c1ccc(-c2cc(-c3ccccc3)cc(-c3c4ccccc4c(-c4ccc5ccccc5c4)c4ccccc34)c2)cc1]
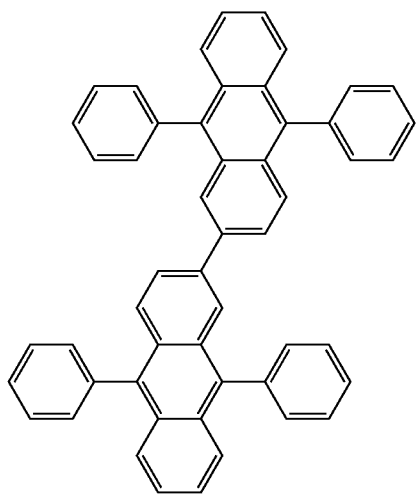 [SMILES: c1ccc(-c2c3ccccc3c(-c3ccccc3)c3cc(-c4ccc5c(-c6ccccc6)c6ccccc6c(-c6ccccc6)c5c4)ccc23)cc1]

-continued
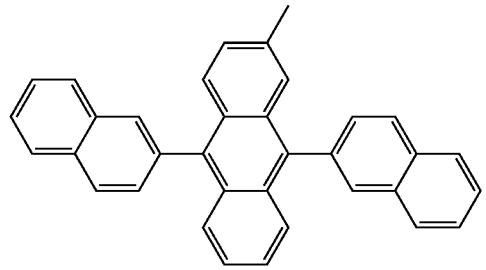 [SMILES: Cc1ccc2c(-c3ccc4ccccc4c3)c3ccccc3c(-c3ccc4ccccc4c3)c2c1]
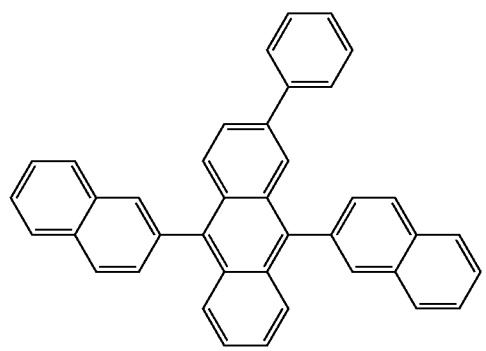 [SMILES: c1ccc(-c2ccc3c(-c4ccc5ccccc5c4)c4ccccc4c(-c4ccc5ccccc5c4)c3c2)cc1]
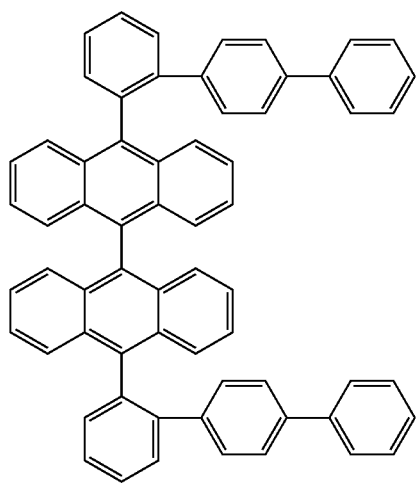 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
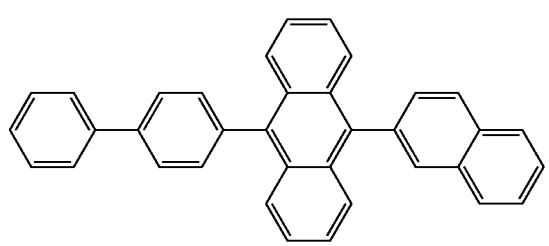 [SMILES: c1ccc(-c2ccc(-c3c4ccccc4c(-c4ccc5ccccc5c4)c4ccccc34)cc2)cc1]

-continued
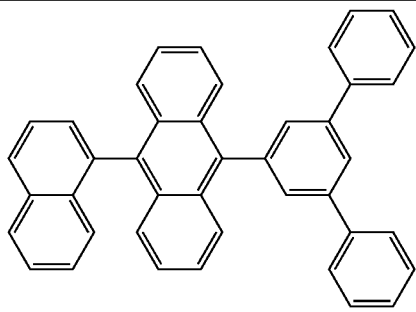
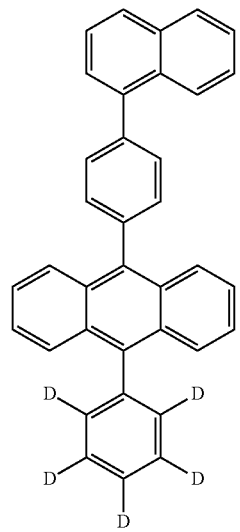 [SMILES: [2H]c1c([2H])c([2H])c(-c2c3ccccc3c(-c3ccc(-c4cccc5ccccc45)cc3)c3ccccc23)c([2H])c1[2H]]
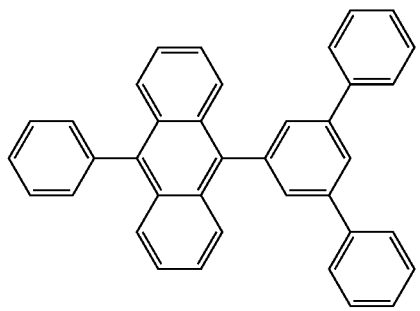 [SMILES: c1ccc(-c2cc(-c3ccccc3)cc(-c3c4ccccc4c(-c4ccccc4)c4ccccc34)c2)cc1]
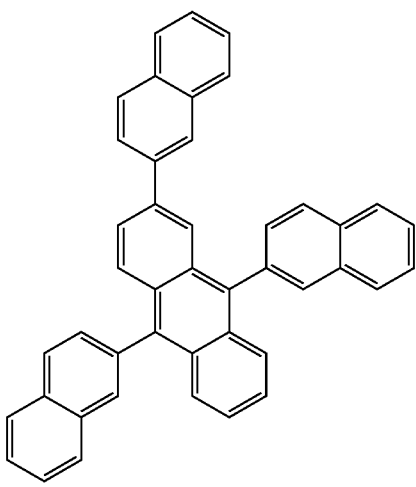 [SMILES: c1ccc2cc(-c3ccc4c(-c5ccc6ccccc6c5)c5ccccc5c(-c5ccc6ccccc6c5)c4c3)ccc2c1]

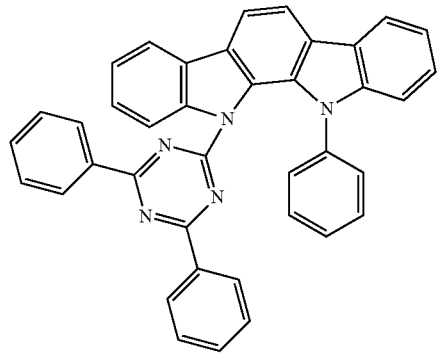 [SMILES: c1ccc(-c2nc(-c3ccccc3)nc(-n3c4ccccc4c4ccc5c6ccccc6n(-c6ccccc6)c5c43)n2)cc1]
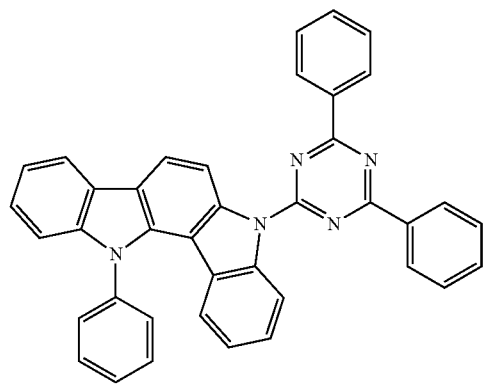 [SMILES: c1ccc(-c2nc(-c3ccccc3)nc(-n3c4ccccc4c4c3ccc3c5ccccc5n(-c5ccccc5)c34)n2)cc1]
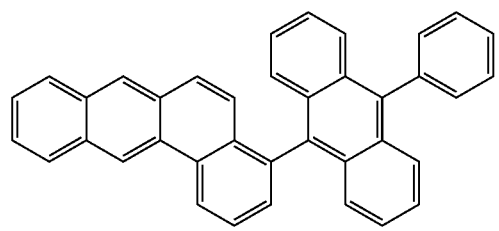 [SMILES: c1ccc(-c2c3ccccc3c(-c3cccc4c3ccc3cc5ccccc5cc34)c3ccccc23)cc1]
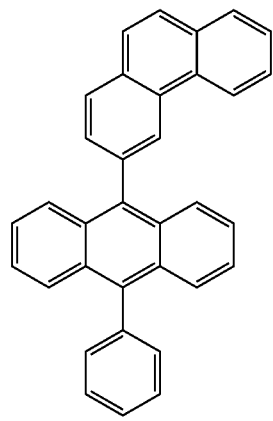 [SMILES: c1ccc(-c2c3ccccc3c(-c3ccc4ccc5ccccc5c4c3)c3ccccc23)cc1]

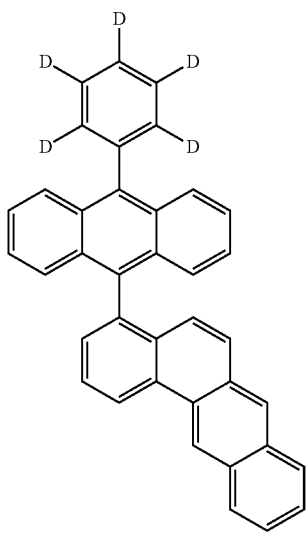 [SMILES: [2H]c1c([2H])c([2H])c(-c2c3ccccc3c(-c3cccc4c3ccc3cc5ccccc5cc34)c3ccccc23)c([2H])c1[2H]]
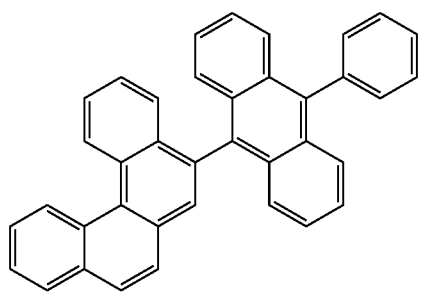 [SMILES: c1ccc(-c2c3ccccc3c(-c3cc4ccc5ccccc5c4c4ccccc34)c3ccccc23)cc1]
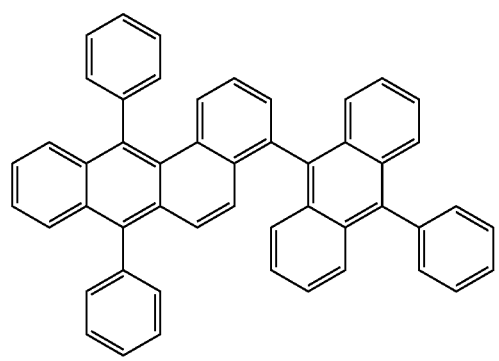 [SMILES: c1ccc(-c2c3ccccc3c(-c3cccc4c3ccc3c(-c5ccccc5)c5ccccc5c(-c5ccccc5)c34)c3ccccc23)cc1]
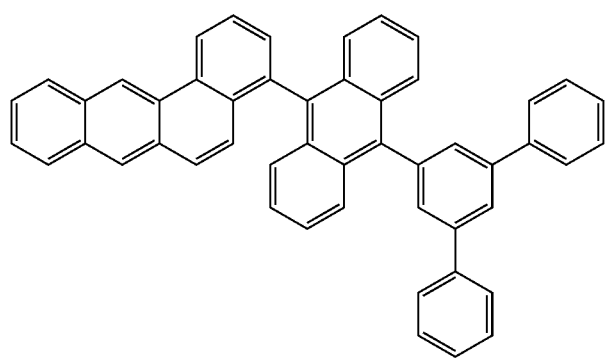 [SMILES: c1ccc(-c2cc(-c3ccccc3)cc(-c3c4ccccc4c(-c4cccc5c4ccc4cc6ccccc6cc45)c4ccccc34)c2)cc1]

-continued
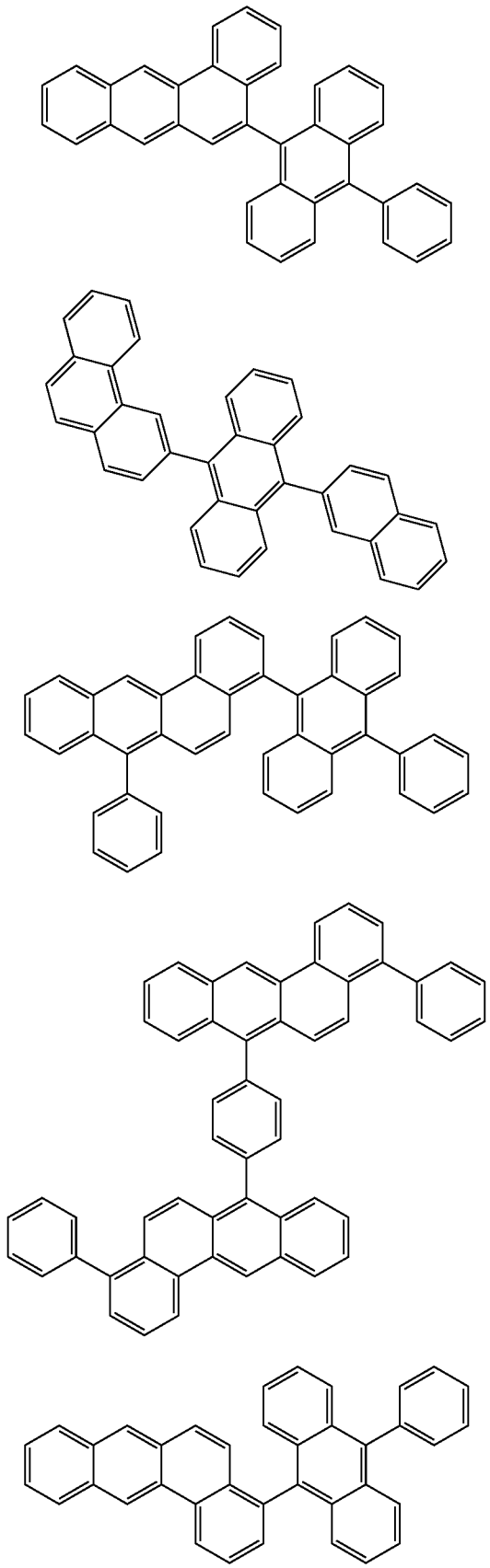

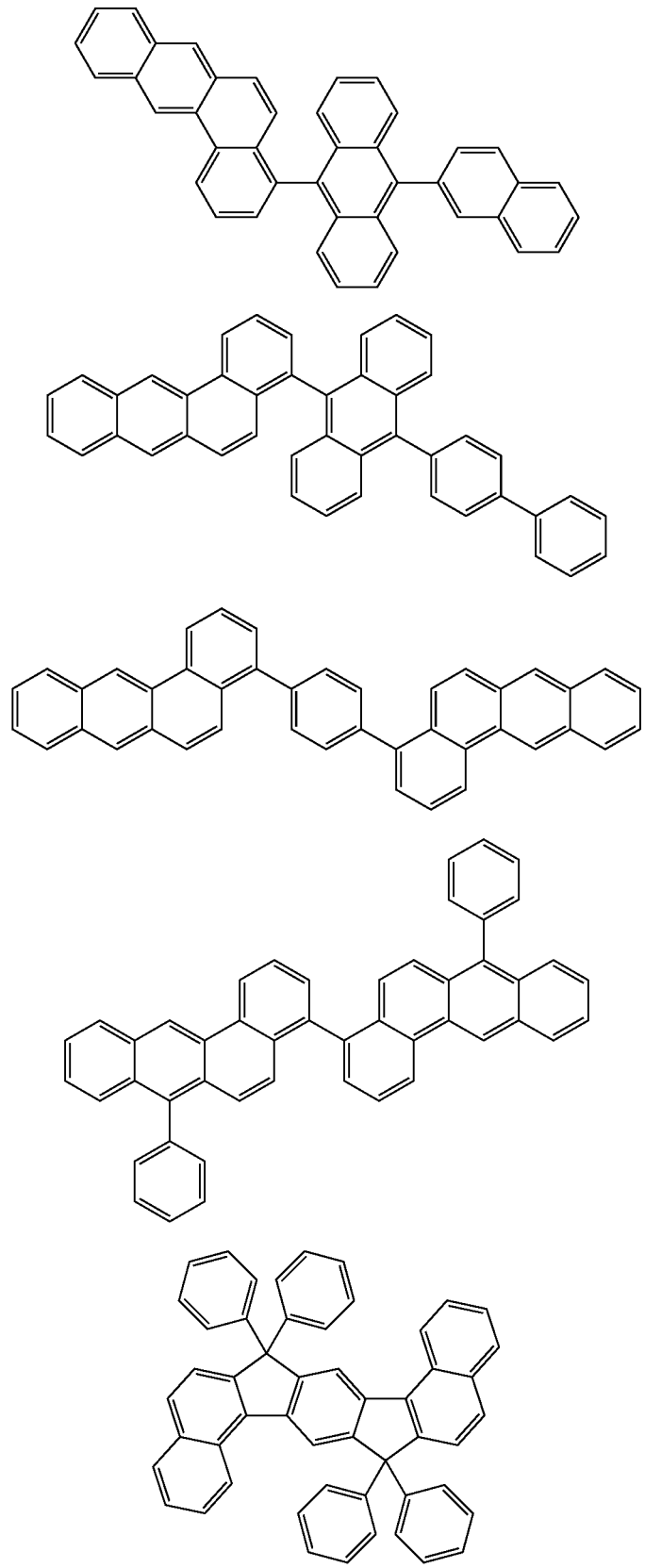

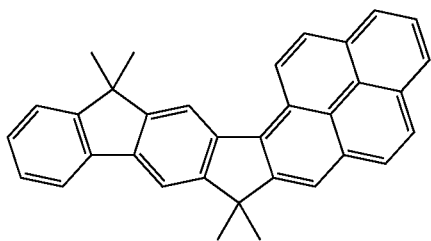 [SMILES: CC1(C)c2ccccc2-c2cc3c(cc21)-c1c(cc2ccc4cccc5ccc1c2c45)C3(C)C]
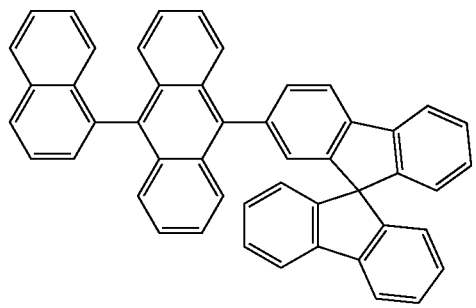 [SMILES: c1ccc2c(c1)-c1ccccc1C21c2ccccc2-c2ccc(-c3c4ccccc4c(-c4cccc5ccccc45)c4ccccc34)cc21]
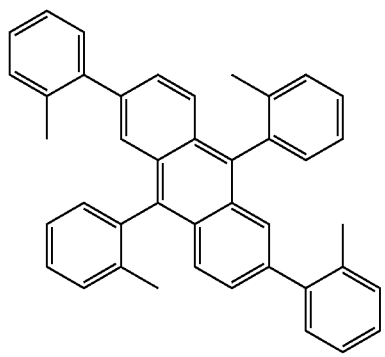 [SMILES: Cc1ccccc1-c1ccc2c(-c3ccccc3C)c3cc(-c4ccccc4C)ccc3c(-c3ccccc3C)c2c1]
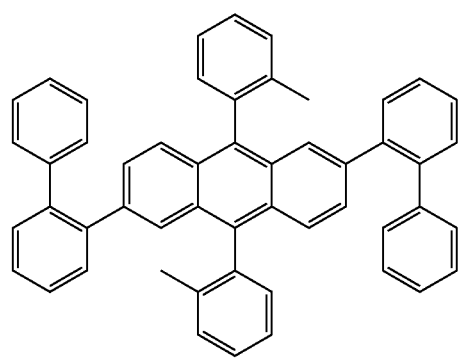 [SMILES: Cc1ccccc1-c1c2ccc(-c3ccccc3-c3ccccc3)cc2c(-c2ccccc2C)c2ccc(-c3ccccc3-c3ccccc3)cc12]

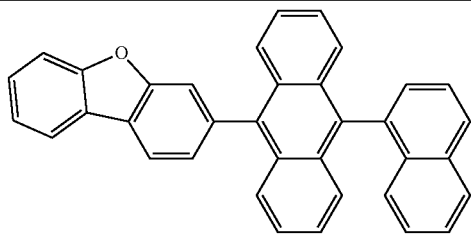

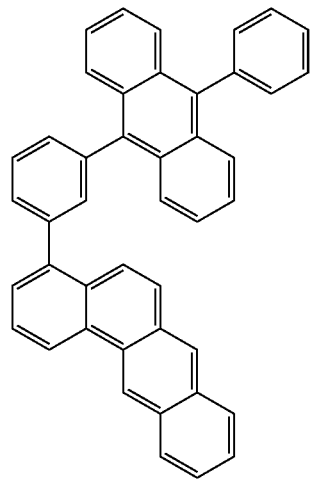 [SMILES: c1ccc(-c2c3ccccc3c(-c3cccc(-c4cccc5c4ccc4cc6ccccc6cc45)c3)c3ccccc23)cc1]

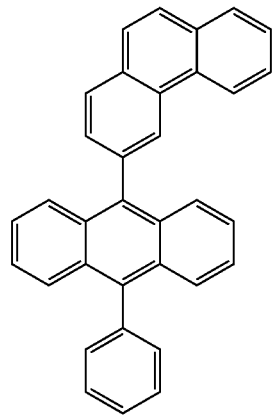 [SMILES: c1ccc(-c2c3ccccc3c(-c3ccc4ccc5ccccc5c4c3)c3ccccc23)cc1]

Suitable charge-transport materials, as can be used in the hole-injection or hole-transport layer or in the electron-transport layer of the organic electroluminescent device according to the invention, are, besides the compounds according to the invention, for example, the compounds disclosed in Y. Shirota et al., Chem. Rev. 2007, 107(4), 953-1010, or other materials, as employed in accordance with the prior art in these layers.

Examples of preferred hole-transport materials which can be used in a hole-transport or hole-injection layer in the electroluminescent device according to the invention are indenofluorenamines and derivatives (for example in accordance with WO 06/122630 or WO 06/100896), the amine derivatives disclosed in EP 1661888, hexaazatriphenylene derivatives (for example in accordance with WO 01/049806), amine derivatives with condensed aromatic compounds (for example in accordance with U.S. Pat. No. 5,061,569), the amine derivatives disclosed in WO 95/09147, monobenzoindenofluorenamines (for example in accordance with WO 08/006,449) or dibenzoindenofluorenamines (for example in accordance with WO 07/140,847). Other suitable hole-transport and hole-injection materials are derivatives of the compounds depicted above, as disclosed in JP 2001/226331, EP 676461, EP 650955, WO 01/049806, U.S. Pat. No. 4,780, 536, WO 98/30071, EP 891121, EP 1661888, JP 2006/253445, EP 650955, WO 06/073054 and U.S. Pat. No. 5,061, 569.

Suitable hole-transport or hole-injection materials are furthermore, for example, the materials shown in the following table.

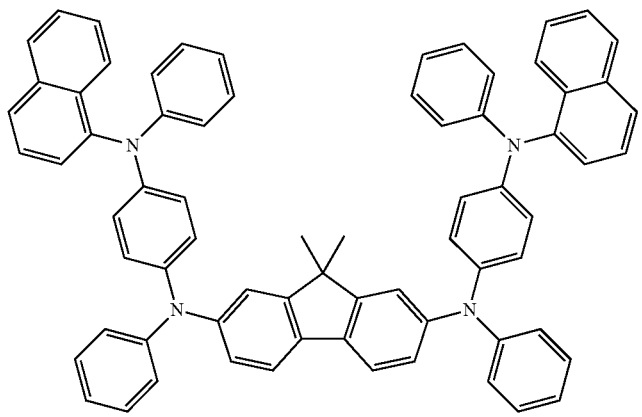 [SMILES: CC1(C)c2cc(N(c3ccccc3)c3ccc(N(c4ccccc4)c4cccc5ccccc45)cc3)ccc2-c2ccc(N(c3ccccc3)c3ccc(N(c4ccccc4)c4cccc5ccccc45)cc3)cc21]
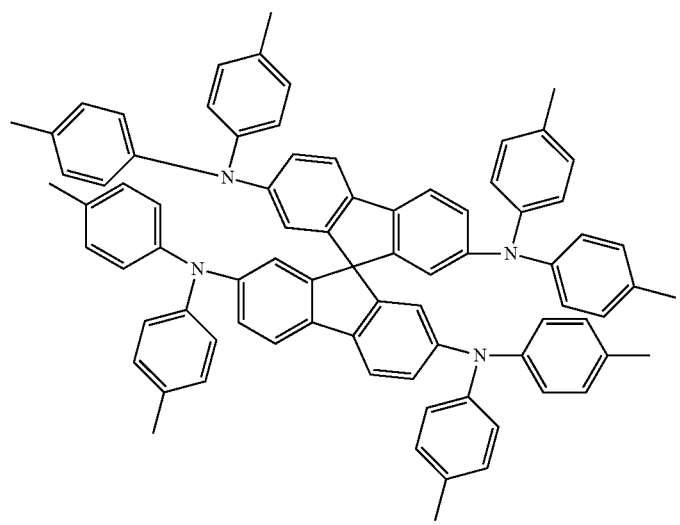
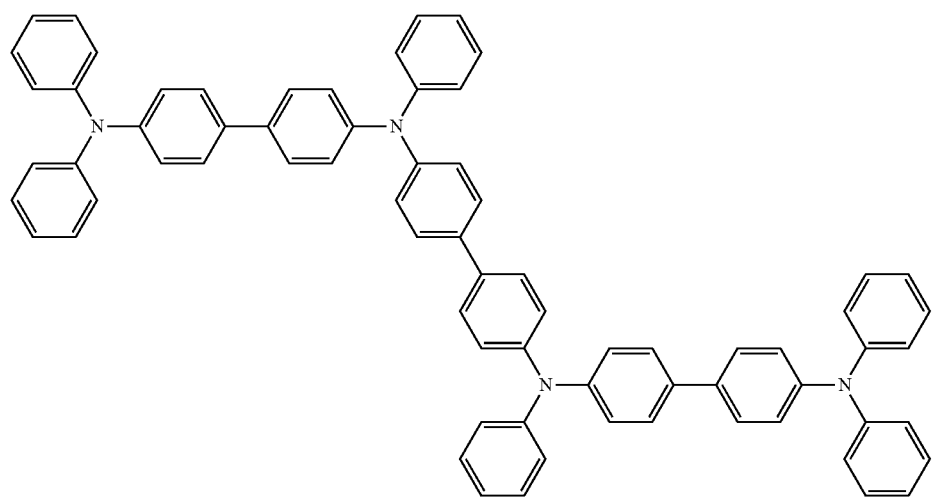 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1]

-continued
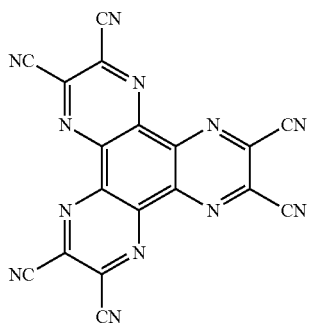 [SMILES: N#Cc1nc2c3nc(C#N)c(C#N)nc3c3nc(C#N)c(C#N)nc3c2nc1C#N]
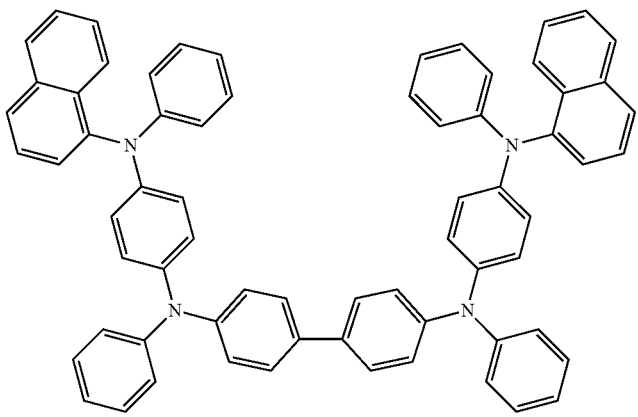 [SMILES: c1ccc(N(c2ccc(-c3ccc(N(c4ccccc4)c4ccc(N(c5ccccc5)c5cccc6ccccc56)cc4)cc3)cc2)c2ccc(N(c3ccccc3)c3cccc4ccccc34)cc2)cc1]
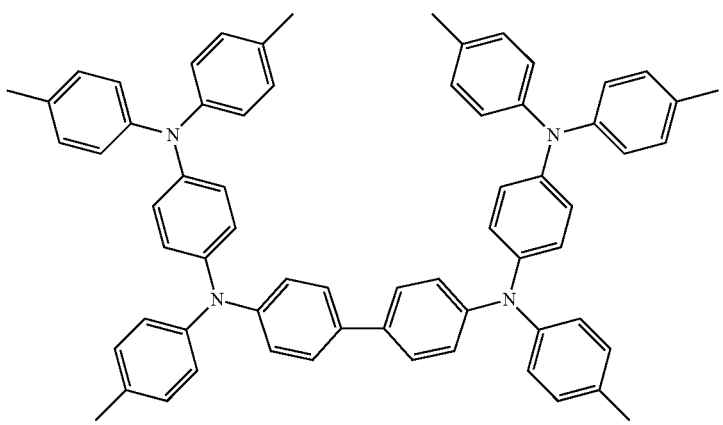
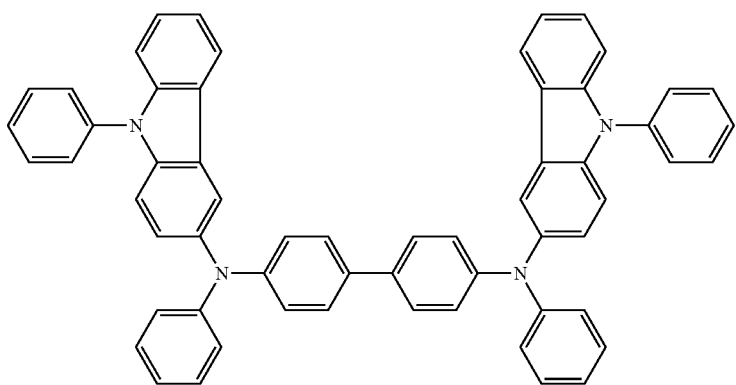 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]

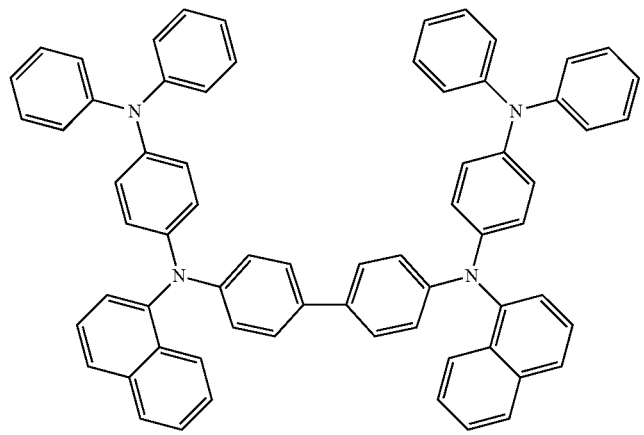 [SMILES: c1ccc(N(c2ccccc2)c2ccc(N(c3ccc(-c4ccc(N(c5ccc(N(c6ccccc6)c6ccccc6)cc5)c5cccc6ccccc56)cc4)cc3)c3cccc4ccccc34)cc2)cc1]
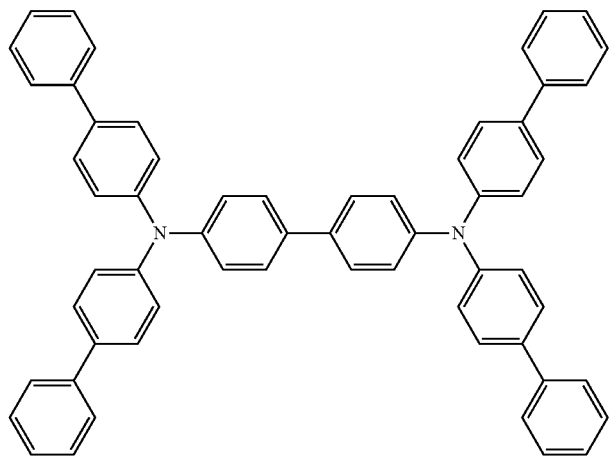 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
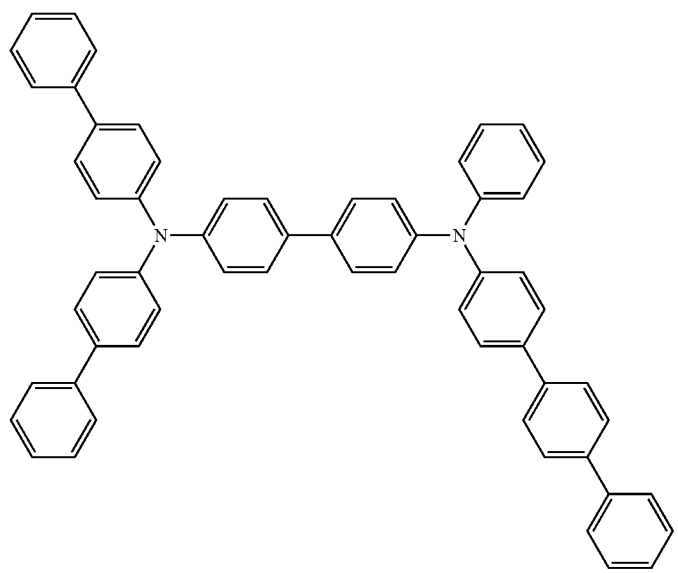 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]

-continued
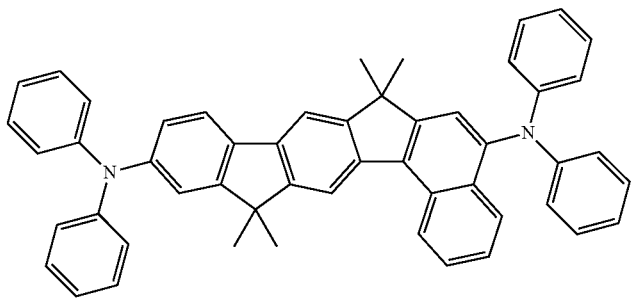 [SMILES: CC1(C)c2cc(N(c3ccccc3)c3ccccc3)ccc2-c2cc3c(cc21)-c1c(cc(N(c2ccccc2)c2ccccc2)c2ccccc12)C3(C)C]
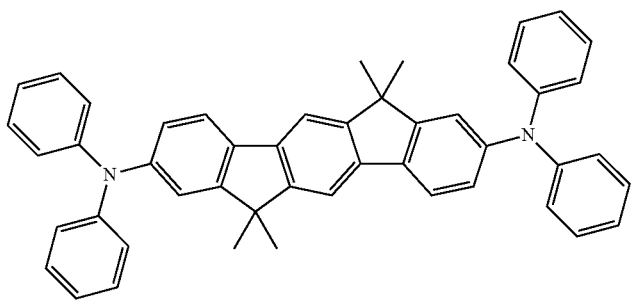 [SMILES: CC1(C)c2cc(N(c3ccccc3)c3ccccc3)ccc2-c2cc3c(cc21)-c1ccc(N(c2ccccc2)c2ccccc2)cc1C3(C)C]
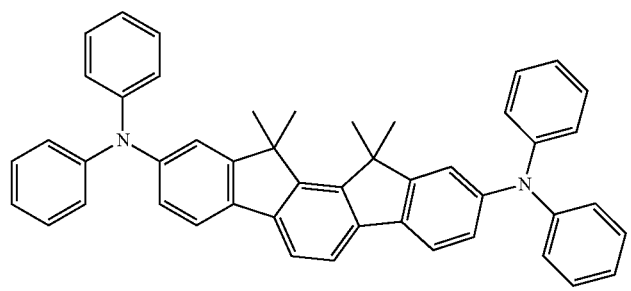 [SMILES: CC1(C)c2cc(N(c3ccccc3)c3ccccc3)ccc2-c2ccc3c(c21)C(C)(C)c1cc(N(c2ccccc2)c2ccccc2)ccc1-3]
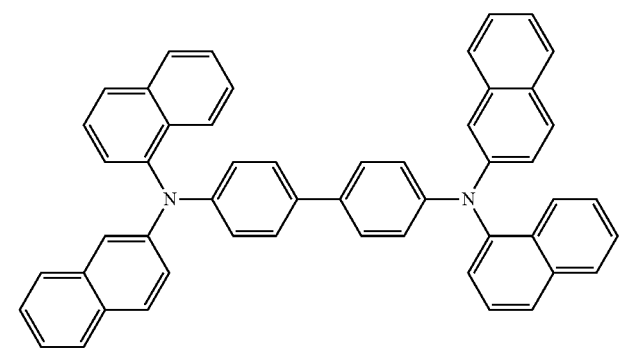 [SMILES: c1ccc2cc(N(c3ccc(-c4ccc(N(c5ccc6ccccc6c5)c5cccc6ccccc56)cc4)cc3)c3cccc4ccccc34)ccc2c1]
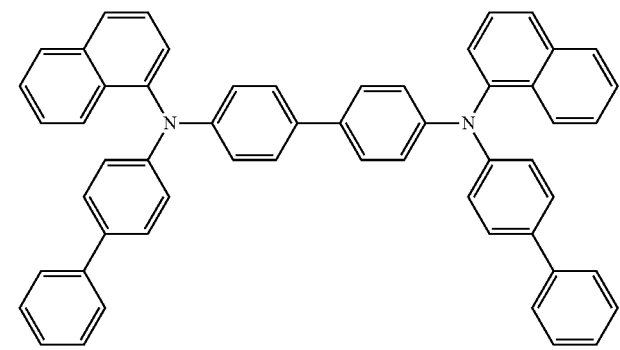 [SMILES: c1ccc(-c2ccc(N(c3ccc(-c4ccc(N(c5ccc(-c6ccccc6)cc5)c5cccc6ccccc56)cc4)cc3)c3cccc4ccccc34)cc2)cc1]

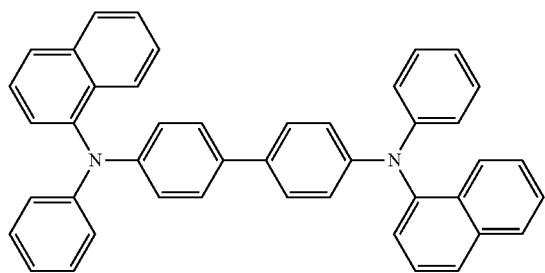 [SMILES: c1ccc(N(c2ccc(-c3ccc(N(c4ccccc4)c4cccc5ccccc45)cc3)cc2)c2cccc3ccccc23)cc1]
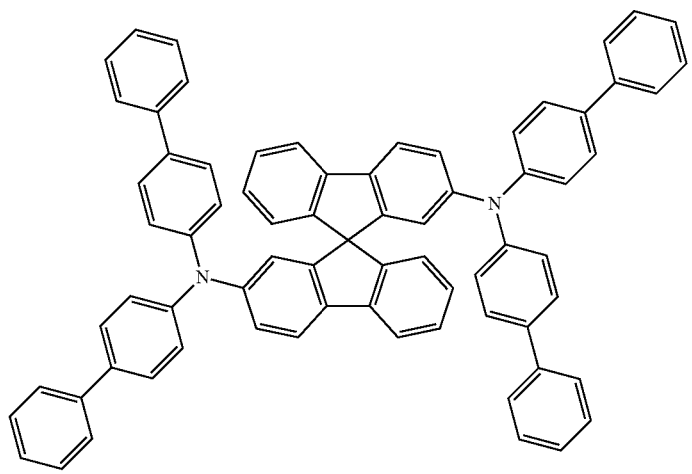 [SMILES: c1ccc(-c2ccc(N(c3ccc(-c4ccccc4)cc3)c3ccc4c(c3)C3(c5ccccc5-4)c4ccccc4-c4ccc(N(c5ccc(-c6ccccc6)cc5)c5ccc(-c6ccccc6)cc5)cc43)cc2)cc1]
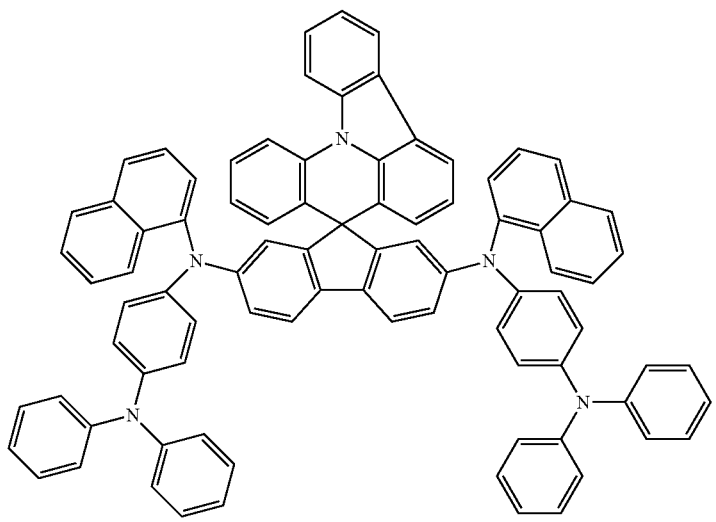 [SMILES: c1ccc(N(c2ccccc2)c2ccc(N(c3ccc4c(c3)C3(c5cc(N(c6ccc(N(c7ccccc7)c7ccccc7)cc6)c6cccc7ccccc67)ccc5-4)c4ccccc4-n4c5ccccc5c5cccc3c54)c3cccc4ccccc34)cc2)cc1]
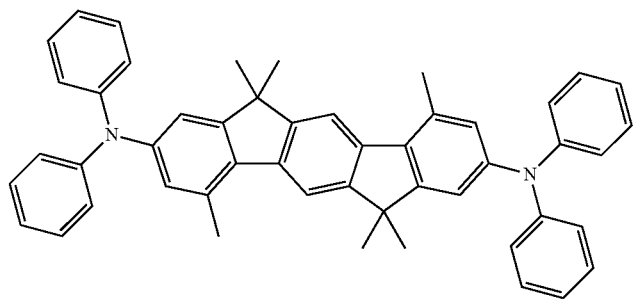 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]

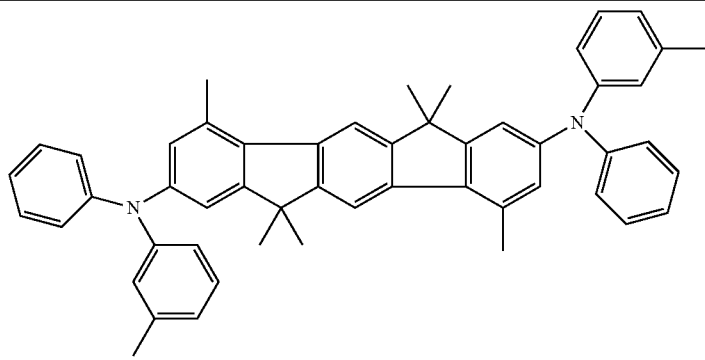

Suitable electron-transport or electron-injection materials which can be used in the electroluminescent device according to the invention are, besides the compounds according to the invention, for example, the materials shown in the following table. Other suitable electron-transport and electron-injection materials are, for example, $AlQ_3$, $BAlQ$, $LiQ$ and $LiF$.

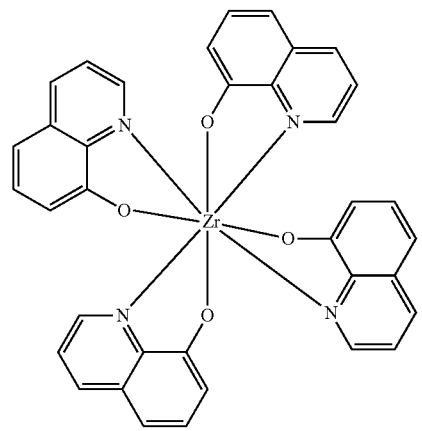

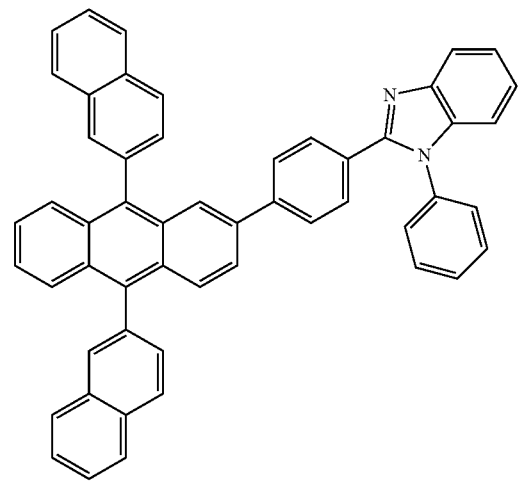 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

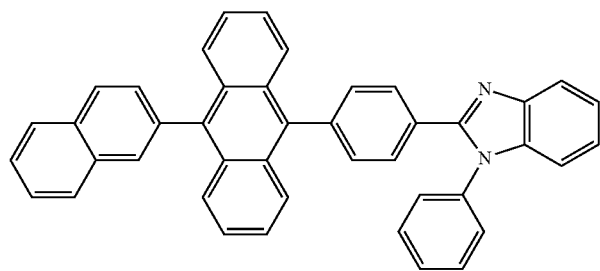 [SMILES: c1ccc(-n2c(-c3ccc(-c4c5ccccc5c(-c5ccc6ccccc6c5)c5ccccc45)cc3)nc3ccccc32)cc1]
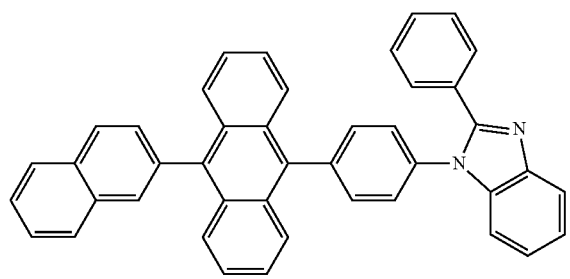 [SMILES: c1ccc(-c2nc3ccccc3n2-c2ccc(-c3c4ccccc4c(-c4ccc5ccccc5c4)c4ccccc34)cc2)cc1]
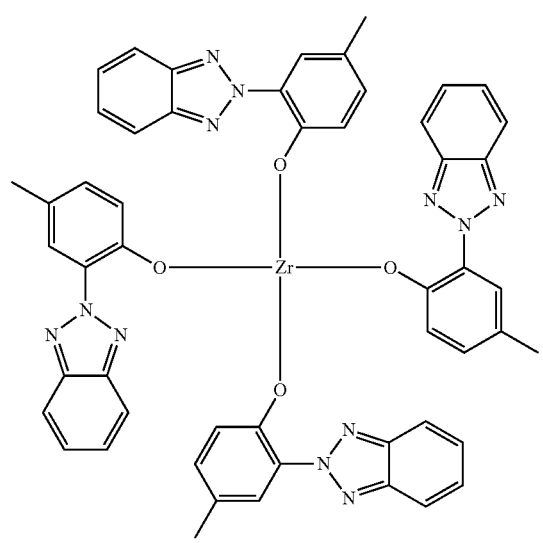
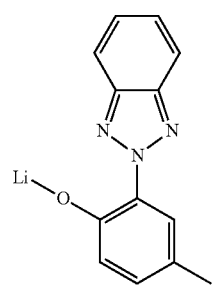

-continued
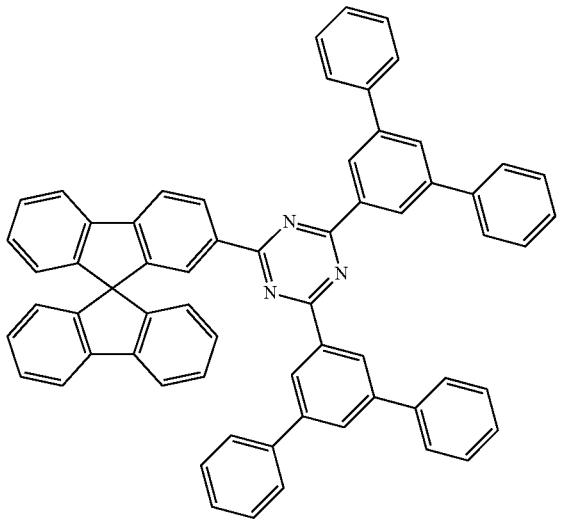 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
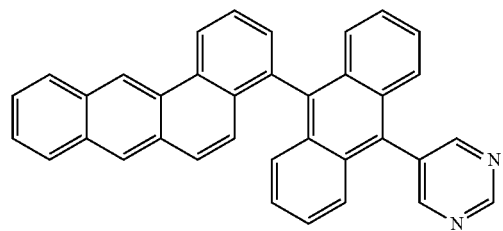 [SMILES: c1ccc2cc3c(ccc4c(-c5c6ccccc6c(-c6cncnc6)c6ccccc56)cccc43)cc2c1]
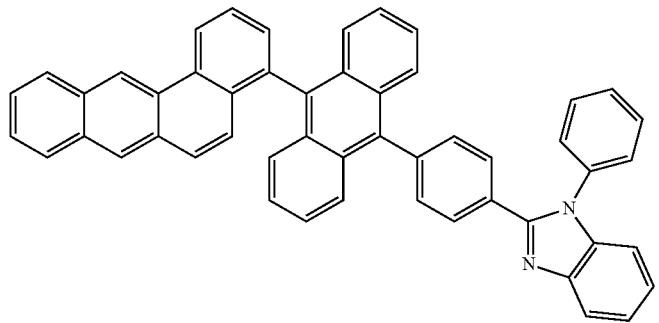 [SMILES: c1ccc(-n2c(-c3ccc(-c4c5ccccc5c(-c5cccc6c5ccc5cc7ccccc7cc56)c5ccccc45)cc3)nc3ccccc32)cc1]
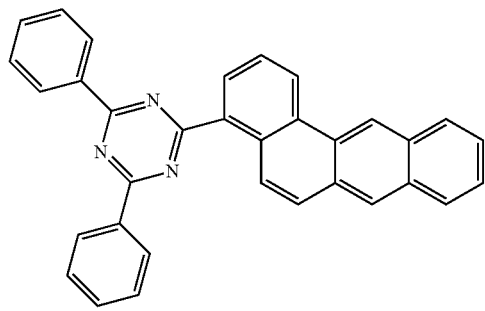 [SMILES: c1ccc(-c2nc(-c3ccccc3)nc(-c3cccc4c3ccc3cc5ccccc5cc34)n2)cc1]

-continued
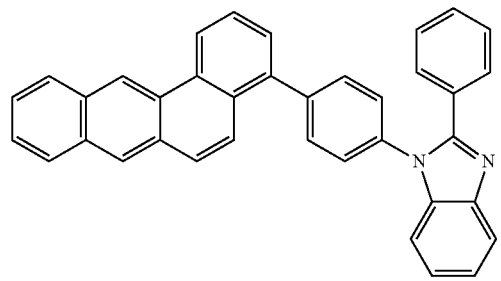 [SMILES: c1ccc(-c2nc3ccccc3n2-c2ccc(-c3cccc4c3ccc3cc5ccccc5cc34)cc2)cc1]
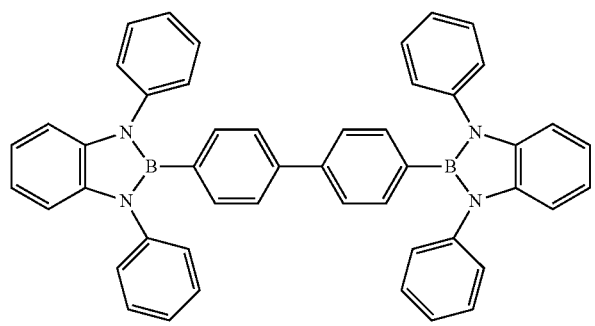 [SMILES: c1ccc(N2B(c3ccc(-c4ccc(B5N(c6ccccc6)c6ccccc6N5c5ccccc5)cc4)cc3)N(c3ccccc3)c3ccccc32)cc1]
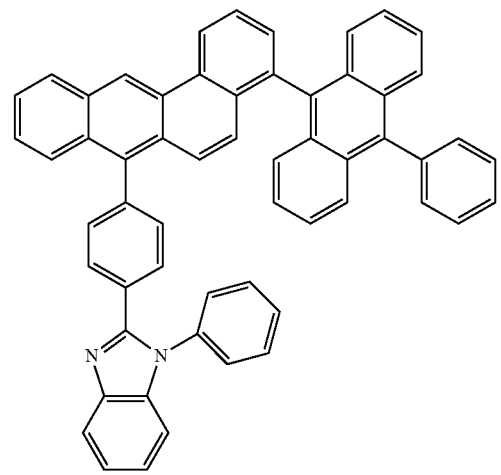 [SMILES: c1ccc(-c2c3ccccc3c(-c3cccc4c3ccc3c(-c5ccc(-c6nc7ccccc7n6-c6ccccc6)cc5)c5ccccc5cc34)c3ccccc23)cc1]
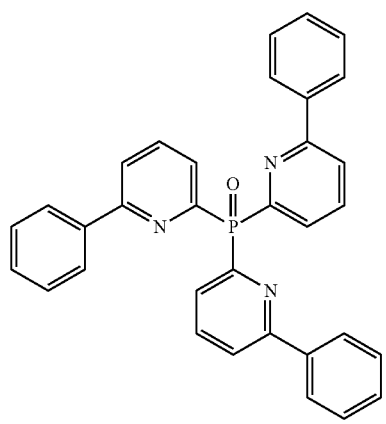 [SMILES: O=P(c1cccc(-c2ccccc2)n1)(c1cccc(-c2ccccc2)n1)c1cccc(-c2ccccc2)n1]

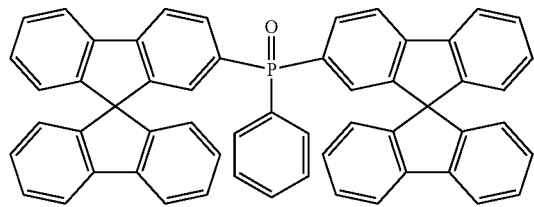 [SMILES: O=P(c1ccccc1)(c1ccc2c(c1)C1(c3ccccc3-c3ccccc31)c1ccccc1-2)c1ccc2c(c1)C1(c3ccccc3-c3ccccc31)c1ccccc1-2]
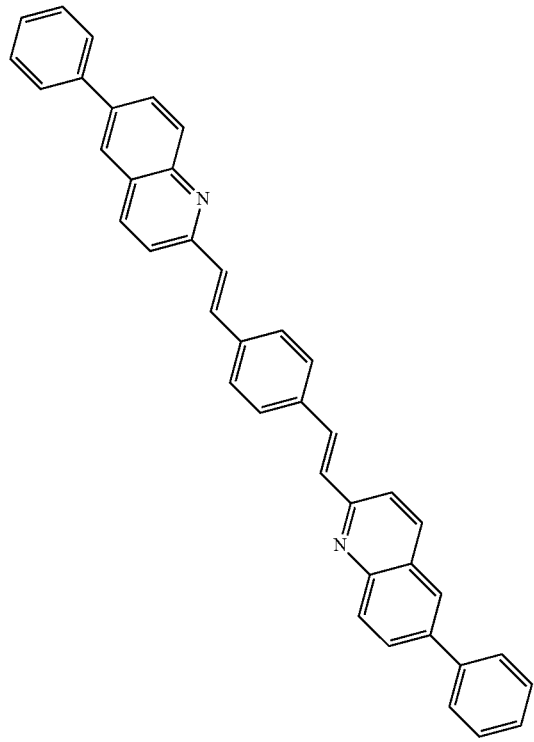 [SMILES: C(=C\c1ccc2cc(-c3ccccc3)ccc2n1)/c1ccc(/C=C/c2ccc3cc(-c4ccccc4)ccc3n2)cc1]
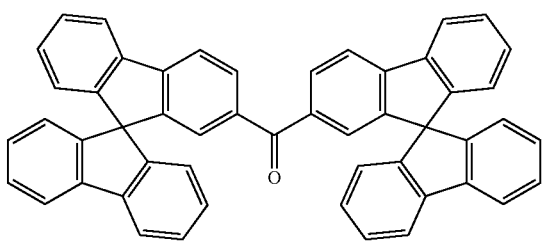 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2]
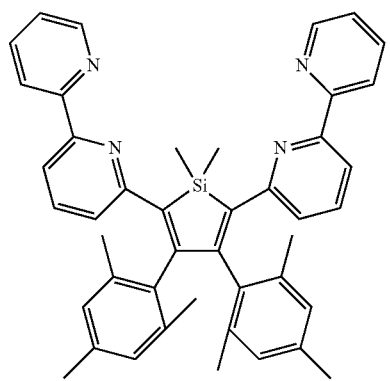 [SMILES: Cc1cc(C)c(C2=C(c3cccc(-c4ccccn4)n3)[Si](C)(C)C(c3cccc(-c4ccccn4)n3)=C2c2c(C)cc(C)cc2C)c(C)c1]

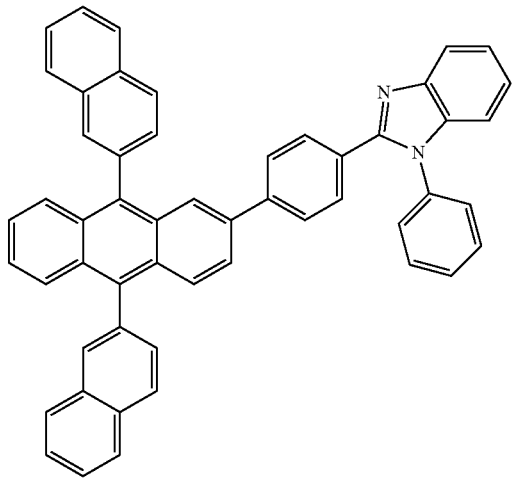 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
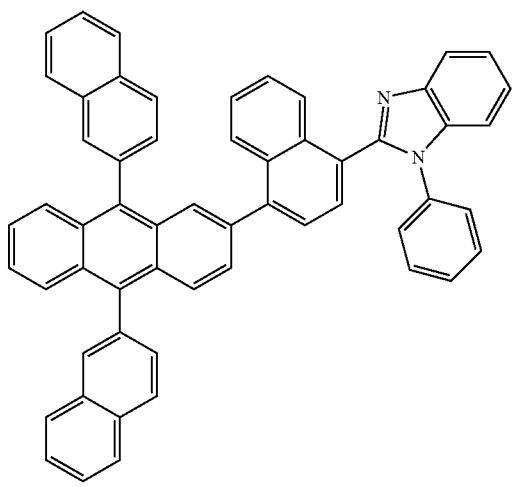 [SMILES: c1ccc(-n2c(-c3ccc(-c4ccc5c(-c6ccc7ccccc7c6)c6ccccc6c(-c6ccc7ccccc7c6)c5c4)c4ccccc34)nc3ccccc32)cc1]
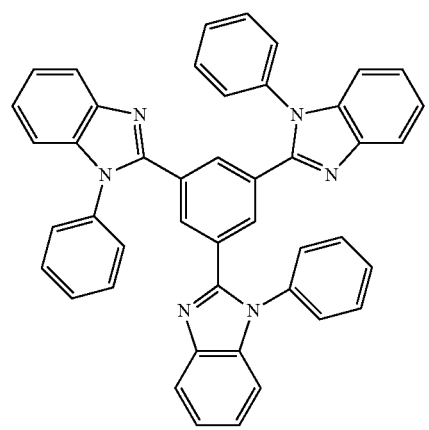 [SMILES: c1ccc(-n2c(-c3cc(-c4nc5ccccc5n4-c4ccccc4)cc(-c4nc5ccccc5n4-c4ccccc4)c3)nc3ccccc32)cc1]

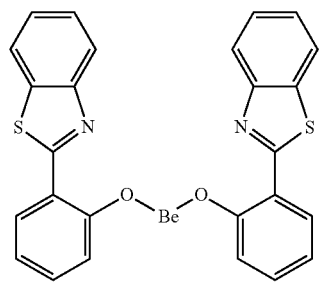
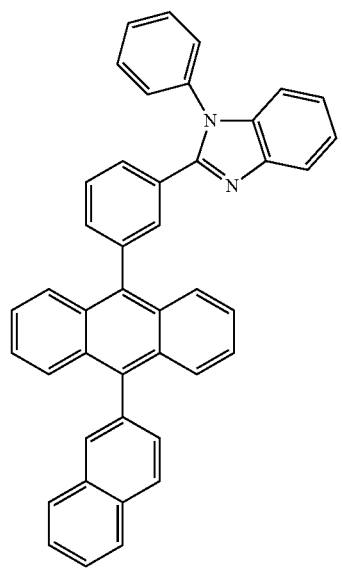 [SMILES: c1ccc(-n2c(-c3cccc(-c4c5ccccc5c(-c5ccc6ccccc6c5)c5ccccc45)c3)nc3ccccc32)cc1]
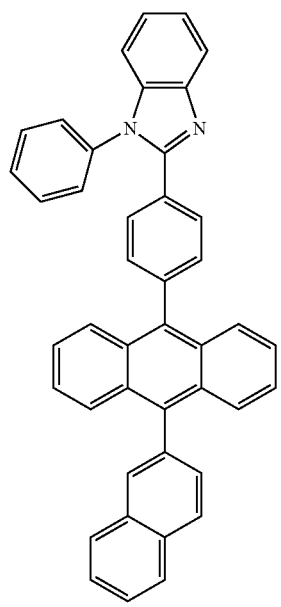 [SMILES: c1ccc(-n2c(-c3ccc(-c4c5ccccc5c(-c5ccc6ccccc6c5)c5ccccc45)cc3)nc3ccccc32)cc1]

-continued

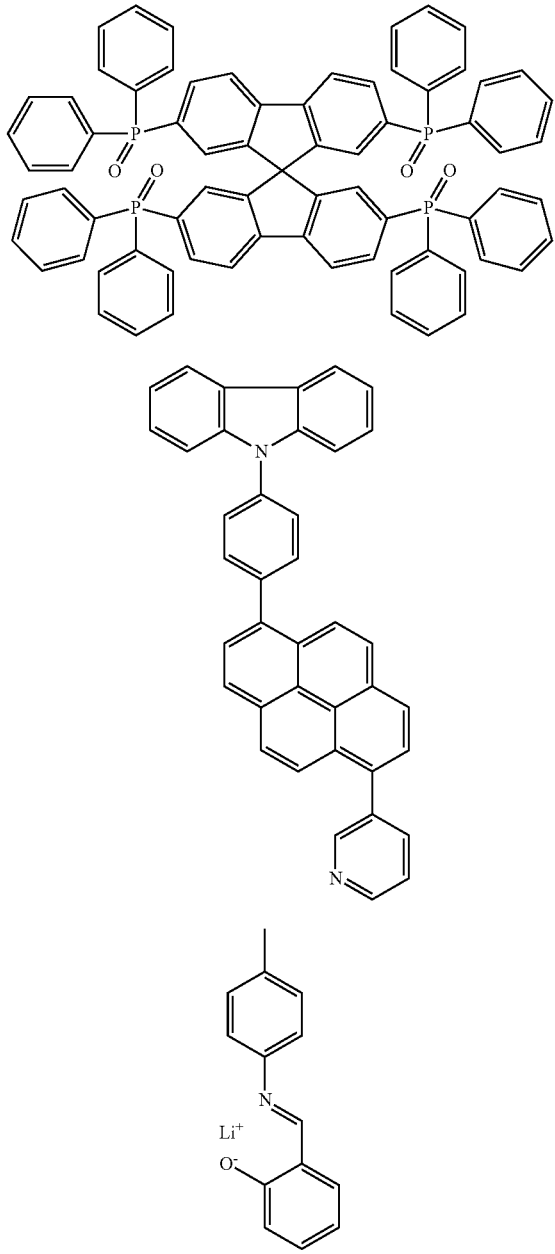

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

Preference is furthermore given to an organic electroluminescent device in which one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, for example, by suitable substitution, are necessary for this purpose.

These processes are generally known to the person skilled in the art and can be applied by him without major experimental effort to organic electroluminescent devices comprising at least one compound of the formula (I).

Finally, it should be noted that all preferred features of the above-mentioned compounds according to the invention and all features thereof which are not explicitly mentioned as preferred, the use thereof in electronic devices and the electronic devices themselves can be combined with one another as desired. All resultant combinations are likewise part of this invention.

The compounds according to the invention are distinguished over the prior art by one or more of the following advantages:

- In contrast to many metal complexes in accordance with the prior art, which undergo partial or complete pyrolytic decomposition on sublimation, the compounds according to the invention have high thermal stability.
- Organic electroluminescent devices comprising the compounds according to the invention as emitting materials have a long lifetime.
- Blue-, red- and green-phosphorescent complexes which have a deep-blue, efficient red or also green emission colour and have a long lifetime on use in organic electroluminescent devices are accessible. In particular in the case of blue-phosphorescent devices, there is still a need for improvement over the prior art, especially with respect to the colour coordinates and the lifetime.

The following examples are intended to explain the invention in greater detail without restricting it. The person skilled in the art will be able to synthesise further compounds according to the invention without inventive step and employ these in electronic devices.

In particular, the features, properties and advantages of the compounds on which the relevant example is based can also be applied to other compounds which are not indicated in detail, but fall within the scope of protection of the claims, unless mentioned otherwise elsewhere.

WORKING EXAMPLES

The following syntheses are, unless indicated otherwise, carried out under a protective-gas atmosphere in dried solvents. The solvents and reagents can be purchased from ALDRICH or ABCR.

Example 1

Pt Complex 1

A) N,N'-Dimethyl-N,N'-bisnaphthylen-1-ylmethyl-propane-1,3-diamine

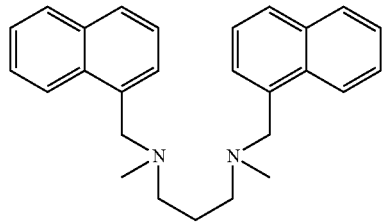 [SMILES: CN(CCCN(C)Cc1cccc2ccccc12)Cc1cccc2ccccc12]

3.5 g (147 mmol) of sodium hydride are suspended in 100 ml of DMF. A mixture of 5.0 g (49 mmol) of N,N'-dimethyl-1,3-propanediamine and 50 ml of DMF is added dropwise to this suspension. When the addition is complete, 18.7 g (106 mmol) of 1-chloromethylnaphthalene are slowly added dropwise, the mixture is heated stepwise to 100° C., stirred at 100° C. for a further 4 h and then allowed to cool, the batch is poured into 1 l of aqueous 2 N NaOH, the aqueous phase is extracted three times with 300 ml of DCM, the combined org. phases are washed twice with 500 ml of water, and the org. phase is dried over magnesium sulfate and then evaporated in vacuo. Yield: 17.3 g (45 mmol), 92.3%, 95% pure according to $^1$H-NMR.

B) N,N'-Dimethyl-N,N'-bisnaphthylen-1-ylmethyl-propane-1,3-diaminobisiodoplatinum(II)

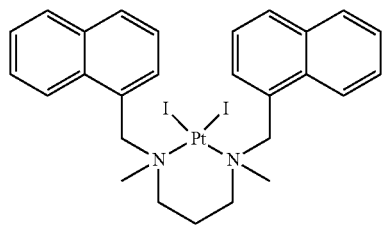

3.2 g (7.7 mmol) of potassium tetrachloroplatinate are dissolved in 120 ml of water, and 6.9 g of a 57% by weight aqueous hydrogen iodide solution are added with stirring.

After the mixture has been stirred for 2 h, 120 ml of methanol are added, a solution of 950 mg (14.4 mmol) of potassium hydroxide pellets (85%) in 30 ml of water is then added to the solution, the mixture is stirred for a further 5 min., and a solution of 3.0 g (7.7 mmol) of N,N-dimethyl-N,N'-bisnaphthylen-1-ylmethylpropane-1,3-diamine in 100 ml of methanol is then added dropwise over the course of 30 min., and the mixture is then heated under reflux for 4 h. After cooling, the olive-coloured solid is filtered off with suction, washed three times with 100 ml of a mixture of methanol/water (1:1, v/v) each time and three times with 100 ml of methanol each time and then dried in vacuo. Yield: 5.6 g (6.8 mmol), 88.3%, 99% pure according to $^1$H-NMR.

C) Pt Complex 1

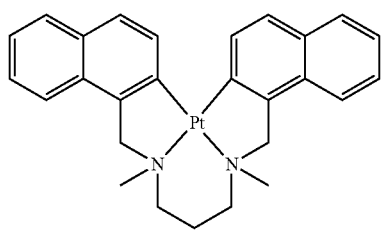

A suspension of 1.67 g (2.0 mmol) of N,N-dimethyl-N,N'-bisnaphthylen-1-ylmethylpropane-1,3-diaminobisiodoplatinum(II) and 254 mg (2.1 mmol) of silver(I) fluoride in 10 ml of sulfolane is stirred at 50° C. for 24 h. The mixture is subsequently chromatographed on silica gel with THF, and the solid obtained is sublimed at 330° C. in vacuo ($10^{-5}$ mbar). Yield: 208 mg (0.36 mmol), 18.1%, mixture of the configurational isomers, δ9.5% pure according to $^1$H-NMR.

Example 2

Pt Complex 2

A) 1,4-Bisnaphthalen-1-ylmethyldiazepan

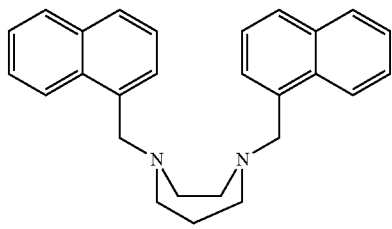 [SMILES: c1ccc2c(CN3CCCN(Cc4cccc5ccccc45)CC3)cccc2c1]

A mixture of 25.0 g (250 mmol) of homopiperazine, 63.6 g (600 mmol) of sodium carbonate, 91.9 g (520 mmol) of 1-chloromethylnaphthalene and 1000 ml of ethanol is heated under reflux for 16 h. After cooling, the reaction mixture is freed from solvent in vacuo, 500 ml of DCM and 300 ml of 0.5 N sodium hydroxide solution are added to the residue, and the org. phase is separated off, washed once with 300 ml of water, dried over magnesium sulfate and then evaporated in vacuo. Yield: 86.4 g (227 mmol), 90.8%, 95% pure according to $^1$H-NMR.

B) 1,4-Bisnaphthalen-1-ylmethyldiazepanobisiodoplatinum(II)

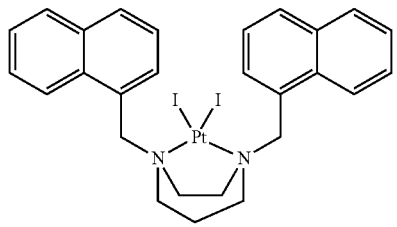

Procedure analogous to Ex. 1 B), using 2.9 g (7.7 mmol) of 1,4-bisnaphthalen-1-ylmethyldiazepan instead of 3.0 g (7.7 mmol) of N,N-dimethyl-N,N'-bisnaphthylen-1-ylmethylpropane-1,3-diamine. Yield: 5.3 g (6.4 mmol), 83.1%, 99% pure according to $^1$H-NMR.

C) Pt Complex 2

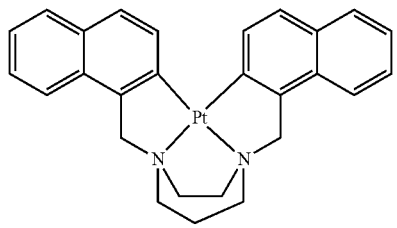

Procedure analogous to Ex. 1 C), using 1.66 g (2.0 mmol) of 1,4-bisnaphthalen-1-ylmethyldiazepanobisiodoplatinum(II) instead of 1.67 g (2.0 mmol) of N,N-dimethyl-N,N'-bisnaphthylen-1-ylmethylpropane-1,3-diaminobisiodoplatinum(II). Sublimation: $p=10^{-5}$ mbar, T=325° C. Yield: 251 mg (0.44 mmol), 21.8%, 99.5% pure according to $^1$H-NMR.

Example 3

Pt Complex 3

A) 1,4-Bisphenylen-1-ylmethylbispidinobisiodoplatinum(II)

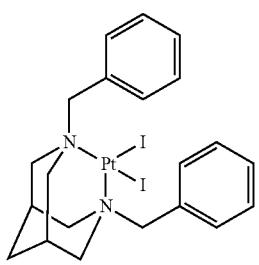

Procedure analogous to Ex. 1 B), using 2.4 g (7.7 mmol) of N,N'-dibenzylbispidine [59009-71-9] instead of 3.0 g (7.7 mmol) of N,N-dimethyl-N,N'-10 bisnaphthylen-1-ylmethyl-propane-1,3-diamine. Yield: 5.5 g (7.3 mmol), 94.8%, 99.5% pure according to $^1$H-NMR.

B) Pt Complex 3

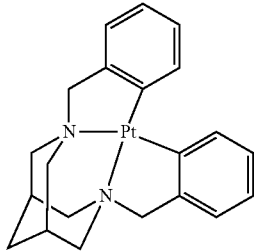

Procedure analogous to Ex. 1 C), using 1.51 g (2.0 mmol) of 1,4-bisphenylen-1-ylmethylbispidinobisiodoplatinum(II) instead of 1.67 g (2.0 mmol) of N,N-dimethyl-N,N'-bisnaph-thylen-1-ylmethylpropane-1,3-diaminobisiodoplatinum(II). Sublimation: p=$10^{-5}$ mbar, T=335° C. Yield: 370 mg (0.74 mmol), 37.0%, 99.5% pure according to $^1$H-NMR.

Example 4

Pt Complex 4

A) 9,9-Bis(3-bromophenyl)-9H-fluorene

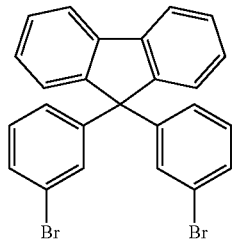 [SMILES: Brc1cccc(C2(c3cccc(Br)c3)c3ccccc3-c3ccccc32)c1]

62.9 g (270 mmol) of 2-bromobiphenyl mixed with 400 ml of THF, 550 ml of toluene, 45 ml of 1,2-dimethoxyethane and 2.6 ml of 1,2-dibromoethane are reacted with 6.6 g (250 mmol) of magnesium to give the corresponding Grignard compound. A solution of 60.0 g (176 mmol) of bis(3-bro-mophenyl) ketone in 600 ml of THF is added dropwise to the cooled Grignard solution. When the addition is complete, the reaction mixture is heated under reflux for 4 h, the solvent is then removed in vacuo, the residue is dissolved in 700 ml of glacial acetic acid, 10 ml of hydrogen bromide in 30% glacial acetic acid are added, and the mixture is heated under reflux for 6 h. After cooling with stirring, the precipitated solid is filtered off with suction, washed twice with 200 ml of glacial acetic acid each time and three times with 300 ml of ethanol each time and then dried in vacuo. Yield: 69.0 g (145 mmol), 82.1%, 99% pure according to $^1$H-NMR.

B) 9,9-Bis-(3-hydroxymethylphenyl)-9H-fluorene

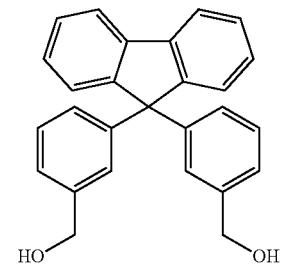 [SMILES: OCc1cccc(C2(c3cccc(CO)c3)c3ccccc3-c3ccccc32)c1]

48.0 ml (120 mmol) of n-BuLi, 2.5 M in hexane, are added dropwise to a solution, cooled to −78° C., of 26.0 g (54.6 mmol) of 9,9-bis-(3-bromophenyl)-9H-fluorene. After the mixture has been stirred at −78° C. for 1 h, a mixture of 13.2 ml of DMF and 20 ml of THF is added rapidly, the mixture is stirred for a further 15 min., 100 ml of methanol, 6.5 ml of acetic acid and 4.5 g of sodium borohydride are then added, and the mixture is then allowed to warm slowly to room temperature. After the mixture has been stirred at room temperature for 16 h, 500 ml of sat. aqueous ammonium chloride solution are added, the org. phase is separated off, and the aqueous phase is extracted once with 300 ml of ethyl acetate. The combined org. phases are washed once with 500 ml of sat. sodium chloride solution and then dried over magnesium sulfate. Finally, the solvent is removed in vacuo. The viscous oil obtained in this way is reacted further without purification. Yield: 20.0 g (52.9 mmol), 97.1%, about 90% pure according to $^1$H-NMR.

C) 9,9-Bis(3-chloromethylphenyl)-9H-fluorene

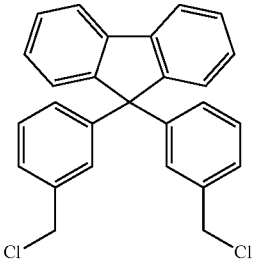 [SMILES: ClCc1cccc(C2(c3cccc(CCl)c3)c3ccccc3-c3ccccc32)c1]

20.0 g (52.9 mmol) of 9,9-bis-(3-hydroxymethylphenyl)-9H-fluorene are dissolved in 300 ml of DCM. A mixture of 16.0 ml of thionyl chloride in 100 ml of dichloromethane is added dropwise to the solution, and the mixture is subsequently stirred at room temperature until the evolution of gas is complete. The solution is washed three times with 200 ml of sat. sodium hydrogencarbonate solution each time and twice with 200 ml of water each time and then dried over magnesium sulfate. The oily residue obtained after removal of the solvent in vacuo is recrystallised twice from ethanol with addition of a little acetone. Yield: 16.0 g (38.5 mmol), 72.8%, about 97% pure according to ¹H-NMR.

D) 9,9-Bis(3-diphenylphosphinophenyl)-9H-fluorene

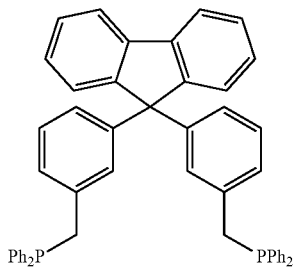

19.2 ml (50 mmol) of n-BuLi, 2.5 M in hexane, are added dropwise with stirring to a mixture, cooled to −40° C., of 9.3 g (50 mmol) of diphenylphosphine and 300 ml of THF. When the addition is complete, the mixture is stirred for 15 min., and a solution of 10.4 g (25 mmol) of 9,9-bis-(3-chloromethylphenyl)-9H-fluorene in THF is then added dropwise. After warming to room temperature, the THF is removed in vacuo, and the residue is recrystallised three times from methanol/toluene. Yield: 12.2 g (17 mmol), 68.2%, about 97% pure according to ¹H-NMR.

E) Pt Complex 4

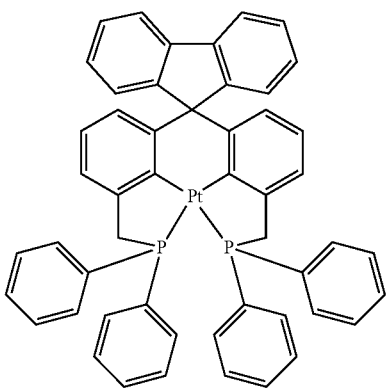

2.9 g (4.0 mmol) of 9,9-bis(3-diphenylphosphinophenyl)-9H-fluorene are added to a solution of 1.39 g (4.0 mmol) of bisacetonitrileplatinum(II) chloride in a mixture of 5 ml of acetonitrile and 100 ml of toluene, and the mixture is then heated under reflux for 6 h. After cooling, the solvent is removed in vacuo, and the residue is chromatographed on silica gel with DCM and then recrystallised from DCM/MeOH. The fine crystal powder is heated at 280° C. in vacuo for 4 h and then sublimed while increasing the temperature to 390° C. Yield: 2.6 g (2.9 mmol), 65.8%, 99.5% pure according to ¹H-NMR.

Examples 5 to 7

Production and Characterisation of Organic Electroluminescent Devices Comprising the Compounds According to the Invention Electroluminescent devices according to the invention can be produced as described, for example, in WO 05/003253.

The results for various OLEDs are compared here. The basic structure, the materials used, the degree of doping and the layer thicknesses thereof are identical for better comparability.

The following device structure is used:

hole-injection layer (HIL) 20 nm of 2,2',7,7'-tetrakis(di-para-tolylamino)spiro-9,9'-bifluorene hole-transport layer (HTL) 5 nm of NPB (N-naphthyl-N-phenyl-4,4'-diaminobiphenyl)

electron-blocking layer (EBL) 15 nm of 9,9-bis-(3,5-diphenylaminophenyl)fluorene (EBL)

emission layer (EML) 40 nm of matrix material: 3,6-bis-N-carbazolyldibenzofuran (M) dopant/emitter: 8% by vol. doping; example compounds 1, 2 and 4 electron conductor (ETL) 20 nm of BAlq cathode 1 nm of LiF, 100 nm of Al on top.

The structures of compounds EBL and M are depicted below for clarity.

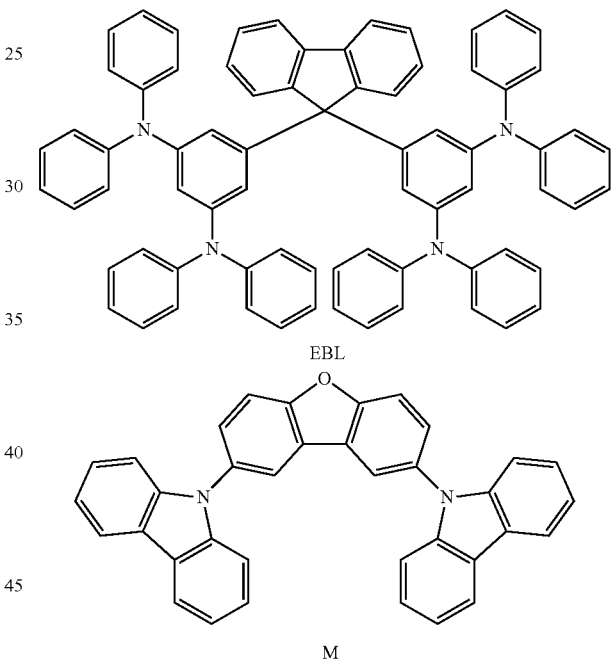

EBL

M

The as yet unoptimised OLEDs described above are characterised by standard methods; for this purpose, the electroluminescence spectra and the external quantum efficiency (measured in %) are determined as a function of the luminance, calculated from current/voltage/luminance characteristic lines (IUL characteristic lines).

TABLE 1

Device results

| Ex. | Dopant | EQE at 100 cd/m² [%] | Voltage at 100 cd/m² [V] | CIE x/y |
|---|---|---|---|---|
| 5 | Pt complex 1 | 5.2 | 5.5 | 0.36/0.59 |
| 6 | Pt complex 2 | 9.4 | 5.7 | 0.36/0.59 |
| 7 | Pt complex 4 | 4.8 | 6.7 | 0.14/0.09 |

The invention claimed is:

1. An electronic device comprising one or more compounds of formulae (II) to (VII),

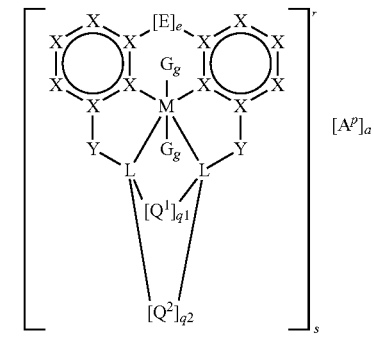

formula (II)

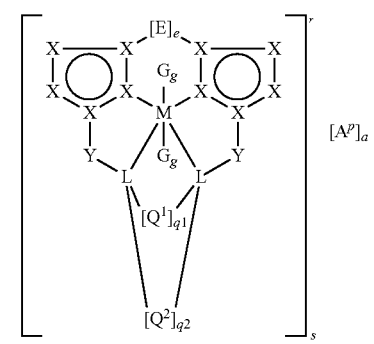

formula (III)

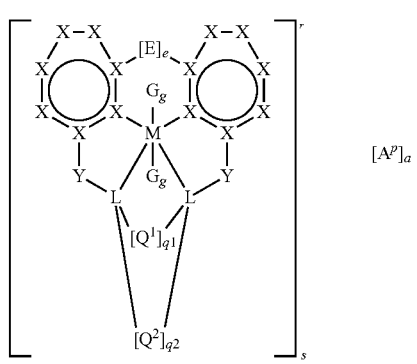

formula (IV)

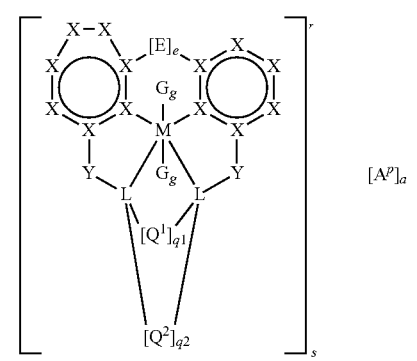

formula (V)

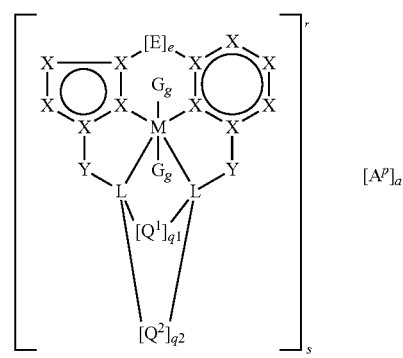

formula (VI)

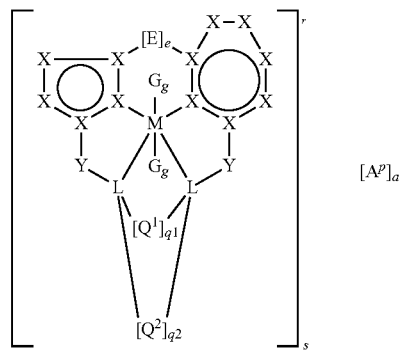

formula (VII)

where the following applies to the symbols and indices occurring:

M is a metal selected from Ir or Pt,

E is on each occurrence, identically or differently, $C(R^B)_2$, O or S,

G is on each occurrence, identically or differently, a neutral, cationic or anionic ligand, $Q^1$ and $Q^2$ are on each occurrence, identically or differently, $C(R^B)_2$, C=O, C=S, $C=C(R^B)_2$, $C=NR^B$, O, S, Se, $CR^B=CR^B$, $PR^B$, $P(R^B)=O$, or phenylene, naphthylene or phenanthrenylene, each of which is optionally substituted by one or more radicals $R^B$, where one or more substituents $Q^1$ is optionally linked to one or more substituents $Q^2$, X is on each occurrence, identically or differently, C, N, or S, where the groups X bonded to Y or E are selected on each occurrence, identically or differently, from C and N and where at least one of the two groups X bonded to M represents a carbon atom, and free bonding sites on the groups X are saturated by substituents $R^C$, Y is on each occurrence, identically or differently, $C(R^B)_2$, L is on each occurrence, identically or differently, N or P, A is on each occurrence, identically or differently, a counterion, e is 0, 1, 2, or 3, where, for e=0, the respective free bonding site on X is saturated by a substituent $R^C$, and where the sum of the values of the indices e, $q^1$ and $q^2$ is greater than or equal to one, g is on each occurrence, identically or differently, 0 or 1, $q^1$ and $q^2$ are on each occurrence, identically or differently, 0, 1, 2, 3 or 4, where the substituents $Q^1$ and $Q^2$ may only occur to the extent of the free bonding sites on L, and, in the case of $q^1$=0 or $q^2$=0, free bonding sites occurring on L is optionally saturated by substituents $R^B$ and where the sum of the values of the indices e, $q^1$, and $q^2$ is greater than or equal to one, a is 0, 1, 2, 3 or 4, p is −4, −3, −2, −1, 0, 1, 2, 3 or 4 and represents the charge number of the group A, r is −4, −3, −2, −1, 0, 1, 2, 3 or 4 and represents the charge number of the complex in square brackets in formula (I), s is 1, 2, 3 or 4, $R^B$ and $R^C$ are on each occurrence, identically or differently, H, D, F, Cl, Br, I, CHO, $N(R^1)_2$, $C(=O)R^1$, $P(=O)(R^1)_2$, $S(=O)R^1$, $S(=O)_2R^1$, $CR^1=C(R^1)_2$, CN, $NO_2$, $Si(R^1)_3$, $B(OR^1)_2$, $OSO_2R^1$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals $R^1$ and where furthermore one or more non-adjacent $CH_2$ groups is optionally replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms is optionally replaced by D, F, Cl, Br, I, CN or $NO_2$, or a mono- or polycyclic aromatic or heteroaromatic ring system having 5 to 60 aromatic ring atoms, which may in each case be substituted by one or more non-aromatic radicals $R^1$, or an aryloxy or heteroaryloxy group having 5 to 60 aromatic ring atoms, which is optionally substituted by one or more non-aromatic radicals $R^1$, or a combination of these systems; in addition, two or more identical or different radicals $R^B$ and $R^C$ is optionally linked to one another and form a mono- or polycyclic, aliphatic or aromatic ring system, $R^1$ is on each occurrence, identically or differently, H, D, F, Cl, Br, I, CHO, $N(R^2)_2$, $C(=O)R^2$, $P(=O)(R^2)_2$, $S(=O)R^2$, $S(=O)_2R^2$, $CR^2=C(R^2)_2$, CN, $NO_2$, $Si(R^2)_3$, $B(OR^2)_2$, $OSO_2R^2$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, or a mono- or polycyclic aromatic or heteroaromatic ring system having 5 to 60 aromatic ring atoms, which may in each case be substituted by one or more non-aromatic radicals $R^2$, or an aryloxy or heteroaryloxy group having 5 to 60 aromatic ring atoms, which is optionally substituted by one or more non-aromatic radicals $R^2$, or a combination of these systems, where two or more radicals $R^1$ is optionally linked to one another and may form a mono- or polycyclic, aliphatic or aromatic ring system, $R^2$ is on each occurrence, identically or differently, H, D, F or an aliphatic, aromatic and/or heteroaromatic organic radical having 1 to 20 C atoms, in which, in addition, one or more H atoms is optionally replaced by F; two or more identical or different substituents $R^2$ here may also be linked to one another and form a mono- or polycyclic, aliphatic or aromatic ring system, and the stoichiometric indices s and a are selected, depending on the charge numbers r and p present in the complex in square brackets in formula (I) or in the counterion A, in such a way that overall a charge-neutral compound results, and, for r=0, a=0, (no counterion A is present).

2. The electronic device according to claim 1, wherein the value of the index e is at least equal to 1 or in that the sum of the values of the indices q1 and q2 is at least equal to 1 or in that both the value of the index e is at least equal to 1 and the sum of the values of the indices q1 and q2 is at least equal to 1.

3. The electronic device according to claim 1, wherein q1 and q2 adopt, identically or differently, the values 1, 2, 3 or 4, and one or more of the substituents Q1 are linked to one or more of the substituents Q2.

4. The electronic device according to claim 1, wherein the ligand G is, identically or differently on each occurrence, a carbon monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, the halides F—, Cl—, Br— and I—, alkyl acetylides, aryl acetylides, cyanide, cyanate, isocyanate, thiocyanate, isothiocyanate, aliphatic or aromatic alcoholates, aliphatic or aromatic thioalcoholates, amides, carboxylates, aryl groups, anionic, nitrogen-containing heterocycles, O2-, S2-, carbides, nitrenes, N3-, diamines, imines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, dithiolates derived from dithiols, borates of nitrogen-containing heterocycles, η5-cyclopentadienyl, η5-pentamethylcyclopentadienyl, η6-benzene or η7-cycloheptatrienyl, each of which is optionally substituted by one or more radicals $R^B$, where the ligand G may also be bonded to the groups E, Y, L, Q1 or Q2.

5. The electronic device according to claim 1, wherein both of the groups X bonded to M represent carbon atoms.

6. The electronic device according to claim 1, wherein the device is an organic electroluminescent device (OLED), an organic integrated circuit (O-IC), an organic field-effect transistor (O-FET), an organic thin-film transistor (O-TFT), an organic light-emitting transistor (O-LET), organic solar cell (O-SC), organic optical detector, organic photoreceptor, organic field-quench device (O-FQD), light-emitting electrochemical cell (LEC) or an organic laser diode (O-laser).

7. The electroluminescent device according to claim 1 where the one or more compounds of formulae (II) to (VII) are used as emitting compound in an emitting layer or as charge-transport compound in a charge-transport layer or charge-injection layer.

* * * * *